(12) United States Patent
Hariton et al.

(10) Patent No.: US 10,856,975 B2
(45) Date of Patent: Dec. 8, 2020

(54) PROSTHETIC VALVE WITH CONCENTRIC FRAMES

(71) Applicant: CARDIOVALVE LTD., Or Yehuda (IL)

(72) Inventors: Ilia Hariton, Zichron Yaackov (IL); Boaz Harari, Ganey Tikva (IL); Meni Iamberger, Kfar Saba (IL); Aviram Baum, Tel Aviv (IL)

(73) Assignee: CARDIOVALVE LTD., Or Yehuda (IL)

( * ) Notice: Subject to any disclaimer, the term of this patent is extended or adjusted under 35 U.S.C. 154(b) by 86 days.

(21) Appl. No.: 16/324,339

(22) PCT Filed: Aug. 8, 2017

(86) PCT No.: PCT/IL2017/050873
§ 371 (c)(1),
(2) Date: Feb. 8, 2019

(87) PCT Pub. No.: WO2018/029680
PCT Pub. Date: Feb. 15, 2018

(65) Prior Publication Data
US 2019/0175342 A1    Jun. 13, 2019

Related U.S. Application Data

(60) Provisional application No. 62/372,861, filed on Aug. 10, 2016.

(51) Int. Cl.
*A61F 2/24* (2006.01)
*B23P 15/00* (2006.01)

(52) U.S. Cl.
CPC .......... *A61F 2/2418* (2013.01); *A61F 2/2412* (2013.01); *A61F 2/2415* (2013.01);
(Continued)

(58) Field of Classification Search
CPC .......... A61F 2/24; A61F 2/2412; A61F 2/2418
(Continued)

(56) References Cited

U.S. PATENT DOCUMENTS

| 4,261,342 A | 4/1981 | Aranguren |
| 4,275,469 A | 6/1981 | Gabbay |

(Continued)

FOREIGN PATENT DOCUMENTS

| CN | 103974674 A | 8/2014 |
| EP | 1264532 | 12/2002 |

(Continued)

OTHER PUBLICATIONS

An office action dated Nov. 23, 2012 in connection with U.S. Appl. No. 13/033,852.

(Continued)

*Primary Examiner* — Suzette J Gherbi
(74) *Attorney, Agent, or Firm* — Sughrue Mion, PLLC

(57) ABSTRACT

Apparatus is provided for use with a heart of a subject, the apparatus including an inner stent frame defining a tubular portion, and an outer stent frame. The apparatus has a relaxed expanded state in which an outer-stent-frame relaxed expanded diameter defined by the outer slept frame is smaller than an inner-stent-frame expanded diameter defined by the tubular portion. Together, the inner stent frame and the outer stent frame define a frame assembly in which outer-frame coupling elements are fixed to inner-frame coupling elements. The frame assembly is expandable into an expanded state in which the tubular portion defines an inner-stent-frame constrained expanded diameter that is smaller than the inner-stent-frame relaxed expanded diameter. The frame assembly includes prosthetic leaflets secured to, and disposed within, the tubular portion, and has a compressed state in which the frame assembly is translumi- (Continued)

nally advanceable to the heart. Other embodiments are also described.

4 Claims, 26 Drawing Sheets

(52) U.S. Cl.
CPC .......... *B23P 15/001* (2013.01); *A61F 2/2436* (2013.01); *A61F 2210/0014* (2013.01); *A61F 2220/0025* (2013.01); *A61F 2220/0075* (2013.01); *A61F 2230/0069* (2013.01); *A61F 2230/0093* (2013.01); *A61F 2240/001* (2013.01); *A61F 2250/0039* (2013.01); *A61F 2250/0063* (2013.01)

(58) Field of Classification Search
USPC .................................................. 623/2.1–2.19
See application file for complete search history.

(56) References Cited

U.S. PATENT DOCUMENTS

| | | |
|---|---|---|
| 4,423,525 A | 1/1984 | Vallana et al. |
| 4,853,986 A | 8/1989 | Allen |
| 4,892,541 A | 1/1990 | Alonso |
| 4,994,077 A | 2/1991 | Dobben |
| 5,078,739 A | 1/1992 | Martin |
| 5,108,420 A | 4/1992 | Marks |
| 5,314,473 A | 5/1994 | Godin |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,473,812 A | 12/1995 | Morris et al. |
| 5,607,444 A | 3/1997 | Lam |
| 5,607,470 A | 3/1997 | Milo |
| 5,647,857 A | 7/1997 | Anderson et al. |
| 5,702,397 A | 12/1997 | Goble et al. |
| 5,765,682 A | 6/1998 | Bley et al. |
| 5,776,140 A | 7/1998 | Cottone |
| 5,868,777 A | 2/1999 | Lam |
| 5,873,906 A | 2/1999 | Lau et al. |
| 5,954,766 A | 9/1999 | Zadno-Azizi et al. |
| 5,957,949 A | 9/1999 | Leonhardt et al. |
| 5,980,565 A | 11/1999 | Jayararnan |
| 6,010,530 A | 1/2000 | Goicoechea |
| 6,019,787 A | 2/2000 | Richard et al. |
| 6,042,607 A | 3/2000 | Williamson, IV |
| 6,059,827 A | 5/2000 | Fenton |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vasquez et al. |
| 6,312,465 B1 | 11/2001 | Griffin et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,391,036 B1 | 5/2002 | Berg |
| 6,402,780 B2 | 6/2002 | Williamson, IV |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,454,799 B1 | 9/2002 | Schreck |
| 6,458,153 B1 | 10/2002 | Bailey et al. |
| 6,482,228 B1 | 11/2002 | Norred |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,719,788 B2 | 4/2004 | Cox |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,893,460 B2 | 5/2005 | Spenser et al. |
| 6,951,571 B1 | 10/2005 | Srivastava |
| 6,960,217 B2 | 11/2005 | Bolduc |
| 6,964,684 B2 | 11/2005 | Ortiz |
| 6,974,476 B2 | 12/2005 | McGuckin et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,137,184 B2 | 11/2006 | Schreck |
| 7,172,625 B2 | 2/2007 | Shu et al. |
| 7,175,656 B2 | 2/2007 | Khairkhahan |
| 7,198,646 B2 | 4/2007 | Figulla et al. |
| 7,201,772 B2 | 4/2007 | Schwammenthal |
| 7,226,477 B2 | 6/2007 | Cox |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal |
| 7,442,204 B2 | 10/2008 | Schwammenthal |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,556,646 B2 | 7/2009 | Yang et al. |
| 7,582,111 B2 | 9/2009 | Krolik et al. |
| 7,585,321 B2 | 9/2009 | Cribier |
| 7,597,711 B2 | 10/2009 | Drews et al. |
| 7,611,534 B2 | 11/2009 | Kapadia |
| 7,621,948 B2 | 11/2009 | Hermann et al. |
| 7,625,403 B2 | 12/2009 | Krivoruchko |
| 7,632,302 B2 | 12/2009 | Vreeman et al. |
| 7,648,528 B2 | 1/2010 | Styrc |
| 7,666,204 B2 | 2/2010 | Thornton et al. |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |

(56) References Cited

U.S. PATENT DOCUMENTS

| | | |
|---|---|---|
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,075,611 B2 | 12/2011 | Millwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |

(56) References Cited

U.S. PATENT DOCUMENTS

| | | |
|---|---|---|
| 8,591,460 B2 | 11/2013 | Wilson et al. |
| 8,591,570 B2 | 11/2013 | Revuelta et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,072,603 B2 | 7/2015 | Tuval et al. |
| 9,084,676 B2 | 7/2015 | Chau et al. |
| 9,095,434 B2 | 8/2015 | Rowe |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,738 B2 | 11/2015 | Murray et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,474,599 B2 | 10/2016 | Keranen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| D800,908 S | 10/2017 | Hariton et al. |
| 9,788,941 B2 | 10/2017 | Hacohen |
| 9,974,651 B2 | 5/2018 | Hariton et al. |
| 9,987,132 B1 * | 6/2018 | Hariton ............... B23P 15/001 |
| 10,010,414 B2 | 7/2018 | Cooper et al. |
| 10,045,845 B2 | 8/2018 | Hacohen et al. |
| 10,098,732 B1 * | 10/2018 | Hariton ............... B23P 15/001 |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,327,895 B2 | 6/2019 | Lozonschi et al. |
| 10,376,361 B2 | 8/2019 | Gross et al. |
| 10,449,047 B2 * | 10/2019 | Hariton ............... A61F 2/243 |
| 10,531,872 B2 | 1/2020 | Hacohen et al. |
| 10,548,731 B2 | 2/2020 | Lashinski et al. |
| 10,667,908 B2 * | 6/2020 | Hariton ............... A61F 2/2436 |
| 10,682,227 B2 * | 6/2020 | Hariton ............... A61F 2/243 |
| 10,695,177 B2 * | 6/2020 | Hariton ............... A61F 2/243 |
| 2001/0002445 A1 | 5/2001 | Vesely |
| 2001/0021672 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0009236 A1 | 1/2003 | Godin |
| 2003/0036791 A1 | 2/2003 | Bonhoeffer et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |

(56) References Cited

U.S. PATENT DOCUMENTS

| | | |
|---|---|---|
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182483 A1 | 8/2005 | Osborne et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256566 A1 | 11/2005 | Gabbay |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Herbert et al. |
| 2006/0135964 A1 | 6/2006 | Vesely |
| 2006/0155357 A1 | 7/2006 | Melsheimer |
| 2006/0161250 A1 | 7/2006 | Shaw |
| 2006/0047297 A1 | 8/2006 | Case |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | VonSegesser et al. |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe et al. |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |

(56) References Cited

U.S. PATENT DOCUMENTS

| | | |
|---|---|---|
| 2009/0299449 A1 | 12/2009 | Styrc |
| 2009/0306768 A1 | 12/2009 | Quardi et al. |
| 2009/0319037 A1 | 12/2009 | Rowe et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben-Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |

(56) References Cited

U.S. PATENT DOCUMENTS

| | | |
|---|---|---|
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0000112 A1 | 1/2014 | Braido et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Salahieh et al. |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277409 A1 | 9/2014 | Bortlein et al. |
| 2014/0277411 A1 | 9/2014 | Börtlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connor et al. |
| 2015/0045880 A1 | 2/2015 | Hacohen |
| 2015/0045881 A1 | 2/2015 | Lim |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0164646 A1 | 6/2015 | McLean et al. |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0282964 A1 | 10/2015 | Beard et al. |
| 2015/0351904 A1 | 10/2015 | Cooper et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0095700 A1 | 4/2016 | Righini |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |

(56) References Cited

U.S. PATENT DOCUMENTS

| | | |
|---|---|---|
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0252159 A1 | 9/2017 | Hacohen et al. |
| 2017/0266003 A1 | 9/2017 | Hammer et al. |
| 2017/0333187 A1 | 11/2017 | Hariton et al. |
| 2017/0360426 A1 | 12/2017 | Hacohen et al. |
| 2017/0367823 A1 | 12/2017 | Hariton et al. |
| 2018/0000580 A1* | 1/2018 | Wallace ............... A61F 2/2418 |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0125644 A1* | 5/2018 | Conklin ............... A61F 2/243 |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0177594 A1 | 6/2018 | Patel et al. |
| 2018/0206983 A1 | 7/2018 | Noe et al. |
| 2018/0250126 A1 | 9/2018 | O'connor et al. |
| 2018/0271654 A1 | 9/2018 | Hariton et al. |
| 2018/0280136 A1 | 10/2018 | Hariton et al. |
| 2018/0296336 A1 | 10/2018 | Cooper et al. |
| 2018/0296341 A1 | 10/2018 | Noe et al. |
| 2018/0344457 A1 | 12/2018 | Gross et al. |
| 2018/0353294 A1 | 12/2018 | Calomeni et al. |
| 2019/0038404 A1 | 2/2019 | Iamberger et al. |
| 2019/0038405 A1 | 2/2019 | Iamberger et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083248 A1 | 3/2019 | Hariton et al. |
| 2019/0083249 A1 | 3/2019 | Hariton et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |
| 2020/0163760 A1* | 5/2020 | Hariton ............... A61F 2/2418 |

FOREIGN PATENT DOCUMENTS

| | | |
|---|---|---|
| WO | 1009/043557 | 10/1998 |
| WO | 1999/30364 | 6/1999 |
| WO | 2000/047139 | 8/2000 |
| WO | 2001/062189 | 8/2001 |
| WO | 06/054930 | 5/2006 |
| WO | 2006/070372 | 7/2006 |
| WO | 2006/089236 | 8/2006 |
| WO | 2007/059252 | 5/2007 |
| WO | 08/013915 | 1/2008 |
| WO | 2008/029296 | 3/2008 |
| WO | 2008/103722 | 8/2008 |
| WO | 09/033469 | 3/2009 |
| WO | 09/053497 | 4/2009 |
| WO | 2009/091509 | 7/2009 |
| WO | 2010/006627 | 1/2010 |
| WO | 2010/081033 | 7/2010 |
| WO | 2011/069048 | 6/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011/143263 | 11/2011 |
| WO | 2012/011108 | 1/2012 |
| WO | 2012/024428 | 2/2012 |
| WO | 2012/127309 | 9/2012 |
| WO | 2012/177942 | 12/2012 |
| WO | 2013/021374 | 2/2013 |
| WO | 2013/021375 | 2/2013 |
| WO | 2002/151970 | 4/2013 |
| WO | 2013/072496 | 5/2013 |
| WO | 2013/078497 | 6/2013 |
| WO | 2013/128436 | 9/2013 |
| WO | 2014/022124 | 2/2014 |
| WO | 2014/076696 | 5/2014 |
| WO | 2014/115149 | 7/2014 |
| WO | 2014/145338 | 9/2014 |
| WO | 2014/164364 | 10/2014 |
| WO | 2014/194178 | 12/2014 |
| WO | 2015/173794 | 11/2015 |
| WO | 2016/093877 | 6/2016 |
| WO | 2018/029680 | 2/2018 |
| WO | 2018/131042 | 7/2018 |
| WO | 2019/026059 | 2/2019 |
| WO | 2019/030753 | 2/2019 |
| WO | 2019/195860 | 10/2019 |

OTHER PUBLICATIONS

An Office Action dated Dec. 31, 2012 U.S. Appl. No. 13/044,694.
An Office Action dated Feb. 6, 2013 U.S. Appl. No. 13/412,814.
Langer et al. "RING plus STRING: Papillary muscle repositioning as an adjunctive repair technique for ischemis mitral regurgitation", J. Thorac Cardiovasc Surg, 133: 247-9, Jan. 2007.
Langer et al; "RING+STRING: Successful repair technique for ischemic mitral regurgitation with severe tethering", Circulation 120[suppl 1]: S85-S91, Sep. 2009.
Webb; Transcatheter Valve-in-Valve Implantation for Failed Bioprosthetic Heart Valves:, Circulation; Apr. 2010; 121; 1848-1857.
Jansen, et al; "Detachable Shape-Memory Sewing Ring for Heart Valves", Artificial Organs, 16:294-297. 1992 (an abstract).
Geha, et al; "Replacement of degenerated mitral and aortic bioprostheses without explanation", Ann Thorac Surg. Jun. 2001; 72:1509-1514.
ISR and WO dated Oct. 13, 2011 PCT/IL11/00231.
Office Action dated Jul. 1, 2016; U.S. Appl. No. 14/161,921.
ISR and WO dated Dec. 5, 2011; PCT/IL11/00582.
USPTO OA dated May 29, 2012; U.S. Appl. No. 12/840,463.
U.S. Appl. No. 61/555,160.
U.S. Appl. No. 61/525,281.
U.S. Appl. No. 61/537,276.
U.S. Appl. No. 61/515,372.
U.S. Appl. No. 61/492,449.
U.S. Appl. No. 61/588,892.
ISR and WO dated Feb. 6, 2013, PCT/IL12/00292.
ISR and WO dated Feb. 6, 2013; PCT/IL 12/00293.
USPTO OA dated Nov. 28, 2012 U.S. Appl. No. 12/961,721.
USPTO OA dated Feb. 15, 2013 U.S. Appl. No. 12/840,463.
USPTO OA dated Feb. 10, 2014 U.S. Appl. No. 13/033,852.
USPTO OA dated Sep. 19, 2014 U.S. Appl. No. 13/044,694.
ISR and WO dated Sep. 4, 2014 PCT/IL2014/050087.
Invitation to Pay Additional Fees dated Jun. 12, 2014; PCT/IL2014/050087.
USPTO OA dated Jun. 17, 2014 U.S. Appl. No. 12/961,721.
USPTO OA dated Jul. 3, 2014 U.S. Appl. No. 13/033,852.
USPTO OA dated May 23, 2014 U.S. Appl. No. 13/412,814.
Himbert Mitral Regurgitation and Stenosis from Bioprosthesis and Annuloplasty Failure: Transcatheter approaches and outcomes:, 24 pages Oct. 28, 2013.
ISR and WO dated Mar. 17, 2014; PCT/IL2013/050937.
IPRP dated Dec. 2, 2013; PCT/IL11/00582.
USPTO OA dated Sep. 12, 2013 U.S. Appl. No. 13/412,814.

(56) References Cited

OTHER PUBLICATIONS

USPTO OA dated Aug. 2, 2013 U.S. Appl. No. 13/033,852.
IPRP dated Sep. 1, 2012 PCT/IL2011/000231.
USPTO OA dated Jul. 2, 2014 U.S. Appl. No. 13/811,308.
USPTO dated Jan. 20, 2016 U.S. Appl. No. 14/161,921.
USPTO dated Jul. 23, 2013 U.S. Appl. No. 12/961,721.
USPTO dated Jul. 18, 2013 U.S. Appl. No. 13/044,694.
USPTO OA dated Nov. 8, 2013 U.S. Appl. No. 12/840,463.
USPTO dated Jun. 4, 2014 U.S. Appl. No. 12/840,463.
USPTO OA dated Aug. 13, 2012 U.S. Appl. No. 13/044,694.
USPTO OA dated Jul. 2, 2012 U.S. Appl. No. 13/033,852.
USPTO OA dated Feb. 3, 2014 U.S. Appl. No. 13/811,308.
IPRP dated Feb. 11, 2014 PCT/IL12/00292.
USPTO OA dated Nov. 26, 2018 U.S. Appl. No. 16/040,831.
USPTO OA dated Jul. 11, 218 U.S. Appl. No. 15/978,494.
USPTO OA dated Nov. 23, 2018 U.S. Appl. No. 16/041,208.
USPTO OA dated Jun. 15, 2018 U.S. Appl. No. 15/970,314.
USPTO OA dated Oct. 12, 2018 U.S. Appl. No. 15/970,314.
USPTO OA dated Jul. 26, 2018 U.S. Appl. No. 15/979,686.
USPTO OA dated Sep. 10, 2018 U.S. Appl. No. 16/008,618.
USPTO OA dated Sep. 6, 2018 U.S. Appl. No. 15/994,022.
USPTO OA dated Sep. 7, 2018 U.S. Appl. No. 15/995,725.
USPTO OA dated Aug. 1, 2019 U.S. Appl. No. 15/668,559.
USPTO OA dated Aug. 16, 2019 U.S. Appl. No. 15/668,559.
USPTO OA dated Apr. 22, 2019 U.S. Appl. No. 15/668,559.
USPTO OA dated Jun. 19, 2019 U.S. Appl. No. 15/682,789.
USPTO NOA dated Aug. 30, 2019 U.S. Appl. No. 15/682,789.
USPTO NOA dated Mar. 29, 2019 U.S. Appl. No. 15/541,783.
An Office Action dated Jun. 25, 2019, which issued during the prosecution of U.S. Appl. No. 15/329,920.
An Office Action dated May 16, 2019, which issued during the prosecution of U.S. Appl. No. 15/433,547.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
IPRP dated Feb. 11, 2014 PCT/IL12/00293.
USPTO NOA dated Aug. 15, 2014 U.S. Appl. No. 13/412,814.
USPTO OA dated Aug. 14, 2012 U.S. Appl. No. 12/961,721.
U.S. Appl. No. 61/283,819.
USPTO NOA dated Apr. 8, 2016 U.S. Appl. No. 14/237,258.
U.S. Appl. No. 61/756,034.
U.S. Appl. No. 61/756,049.
IPRP dated Jan. 31, 2017 PCT/IL2015/050792.
U.S. Appl. No. 62/372,861.
USPTO NOA dated Aug. 13, 2018 U.S. Appl. No. 15/995,597.
USPTO NOA dated Apr. 20, 2018 U.S. Appl. No. 15/878,206.
USPTO OA dated Dec. 10, 2015 U.S. Appl. No. 14/237,258.
IPRP dated Jul. 28, 2015 PCT/IL2014/050087.
USPTO OA dated Nov. 27, 2015 U.S. Appl. No. 14/626,267.
USPTO OA dated Jan. 21, 2016 U.S. Appl. No. 14/237,264.
Office Action dated Jan. 30, 2015 UK Appln. 1413474.6.
ISR and WO dated May 30, 2016 PCT/IL2016/050125.
USPTO OA dated Sep. 26, 2016 U.S. Appl. No. 14/763,004.
USPTO OA dated Jan. 18, 2017 U.S. Appl. No. 14/626,267.
USPTO OA dated Feb. 7, 2017 U.S. Appl. No. 14/689,608.
Office Action dated Feb. 8, 2017 UK Appln. 1613219.3.
Office Action dated Feb. 1, 2017 EP Appln. 12821522.5.
ISR and WO dated Oct. 27, 2015 PCT/IL2015/050792.
ESR dated Feb. 18, 2015 EP 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve- interventions.
USPTO AA dated Apr. 2, 2018 U.S. Appl. No. 14/763,004.
USPTO OA dated Jul. 26, 2018 U.S. Appl. No. 15/872,501.
USPTO OA dated May 4, 2018 U.S. Appl. No. 15/872,501.
USPTO OA dated Apr. 20, 2018 U.S. Appl. No. 15/886,517.
USPTO OA dated Aug. 9, 2018 U.S. Appl. No. 15/899,858.
USPTO OA dated Aug. 9, 2018 U.S. Appl. No. 15/902,403.
USPTO OA dated Jun. 28, 2018 U.S. Appl. No. 29/635,658.
USPTO OA dated Jun. 28, 2018 U.S. Appl. No. 29/635,661.
Lutter et al; "Percutaneous Valve Replacement: Current State and Future Prospects", The Annals of Thoracic Surgery, vol. 78, pp. 2199-2206 Dec. 2004.
Office Action dated Jun. 6, 2018 UK Appln. 1720803.4.
U.S. Appl. No. 62/560,384.
ISR and WO dated Jun. 20, 2018 PCT/IL2018/050024.
Office Action dated Jun. 18, 2018 UK Appln, 1800399.6.
USPTO OA dated Oct. 23, 2017 U.S. Appl. No. 14/763,004.
USPTO dated Dec. 7, 2017 U.S. Appl. No. 15/213,791.
Interview Summary dated Feb. 8, 2018 U.S. Appl. No. 15/213,791.
USPTO OA dated Feb. 7, 2018 U.S. Appl. No. 15/197,069.
ISR and WO dated Nov. 24, 2017 PCT/IL2017/050873.
USPTO OA dated Jan. 5, 2018 U.S. Appl. No. 15/541,783.
USPTO OA dated Feb. 2, 218 U.S. Appl. No. 15/329,920.
Invitation to Pay Additional Fees dated Jan. 2, 2018 PCT/IL2017/050849.
Invitation to Pay Additional Fees dated Sep. 29, 2017 PCT/IL2017/050873.
ESR dated Jun. 29, 2017 EP 11809374.9.
Invitation to pay Additional Fees dated Oct. 11, 2018 PCT/IL2018/050725.
USPTO OA dated Dec. 4, 2018 U.S. Appl. No. 16/045,059.
CNOa dated Nov. 5, 2018 CN20168008328.5.
USPTO NOA dated Sep. 25, 2018 U.S. Appl. No. 15/188,507.
ESR dated Sep. 26, 2018 EP 18186784.7.
USPTO OA dated Jun. 30, 2015 U.S. Appl. No. 14/522,987.
USPTO NOA dated Dec. 13, 2013 U.S. Appl. No. 13/675,119.
IPRP dated Aug. 8, 2017 PCT/IL2016/050125.
USPTO OA dated Jan. 17, 2018 U.S. Appl. No. 14/763,004.
USPTO OA dated Mar. 25, 2015 U.S. Appl. No. 12/840,463.
USPTO OA dated Feb. 25, 2016 U.S. Appl. No. 14/522,987.
USPTO OA dated Apr. 13, 2016 U.S. Appl. No. 14/626,267.
USPTO OA dated Aug. 28, 2015 U.S. Appl. No. 14/237,264.
U.S. Appl. No. 62/112,343.
Maisano (2015) TCR presentation re Cardiovalve.
USPTO NOA dated Sep. 29, 2016 U.S. Appl. No. 14/442,541.
USPTO NOA dated May 10, 2016 U.S. Appl. No. 14/237,258.
USPTO NOA dated May 20, 2016 U.S. Appl. No. 14/237,258.
IPRP dated May 1, 215 PCT/IL2013/050937.
Pavcnik et al; "Development and Initial Experimental Evaluation of a Prosthetic Aortic Valve for Transcatheter Placement", Cardiovascular Radiology. Radiology Apr. 1992, vol. 183, pp. 151-154.
USPTO NOA dated Oct. 16, 2013 U.S. Appl. No. 13/675,119.
USPTO NOA dated Feb. 11, 2015 U.S. Appl. No. 13/033,852.
USPTO NOA dated May 5, 2015 U.S. Appl. No. 12/840,463.
USPTO NOA dated Mar. 1, 2015 U.S. Appl. No. 13/811,308.
USPTO NOA dated Jul. 1, 2016 U.S. Appl. No. 14/442,541.
ISR and WO dated Nov. 9, 2018 PCT/IL2018/050869.
ISR and WO dated Dec. 5, 2018 PCT/IL2018/050725.
ISR and WO dated Apr. 25, 2019 PCT/IL2019/050142.
IPRP dated Feb. 12, 2019 PCT/IL2017/050873.
Office Action dated Mar. 25, 2019 EP Appln. 14710060.6.
ISR and WO dated Jan. 25, 2019 PCT/IL2018/051122.
ISR and WO dated May 13, 2019 PCT/IL2018/051350.
IPRP dated Feb. 5, 2019, PCT/IL2017/050849.
USPTO Oa dated Oct. 25, 2018 U.S. Appl. No. 14/763,004.
USPTO dated Mar. 4, 2019 U.S. Appl. No. 14/763,004.
USPTO OA dated Jan. 9, 2019 U.S. Appl. No. 15/329,920.

(56) References Cited

OTHER PUBLICATIONS

USPTO OA dated Jan. 30, 2019 U.S. Appl. No. 15/872,51.
USPTO OA dated Feb. 5, 2019 U.S. Appl. No. 15/899,858.
USPTO OA dated May 23, 2019 U.S. Appl. No. 15/668,659.
USPTO OA dated May 1, 2019 U.S. Appl. No. 15/691,032.
USPTO OA dated Nov. 16, 2018 U.S. Appl. No. 16/042,028.
An Office Action dated Jan. 6, 2020, which issued during the prosecution of U.S. Appl. No. 16/660,231.
An Office Action dated Dec. 31, 2019, which issued during the prosectution of U.S. Appl. No. 16/183,140.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action summarized English translation and Search Report dated Jul. 3, 2020, which issued during the prosecution of Chinese Patent Application No. 201780061210.3.
Sündermann, Simon H., et al. "Feasibility of the Engager$^{TM}$ aortic transcatheter valve system using a flexible over-the-wire design." European Journal of Cardio-Thoracic Surgery 42.4 (2012): pp. e48-e52.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&Ipg=PA198&ots=soqWrDH-y_&dg=%20%22Edwards%20SAPIEN%22&lr&pg=PA20#v=onepage&q=%22Edwards%20SAPIEN%22&f=false ; Downloaded on Jun. 18, 2020, 2 pages.

\* cited by examiner

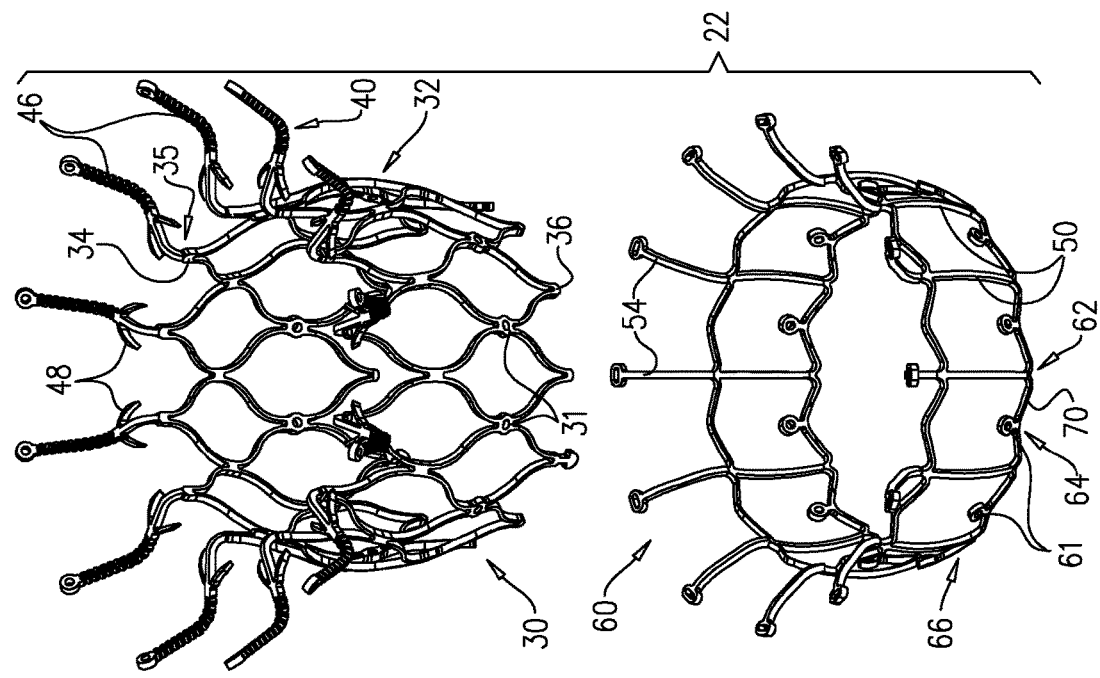
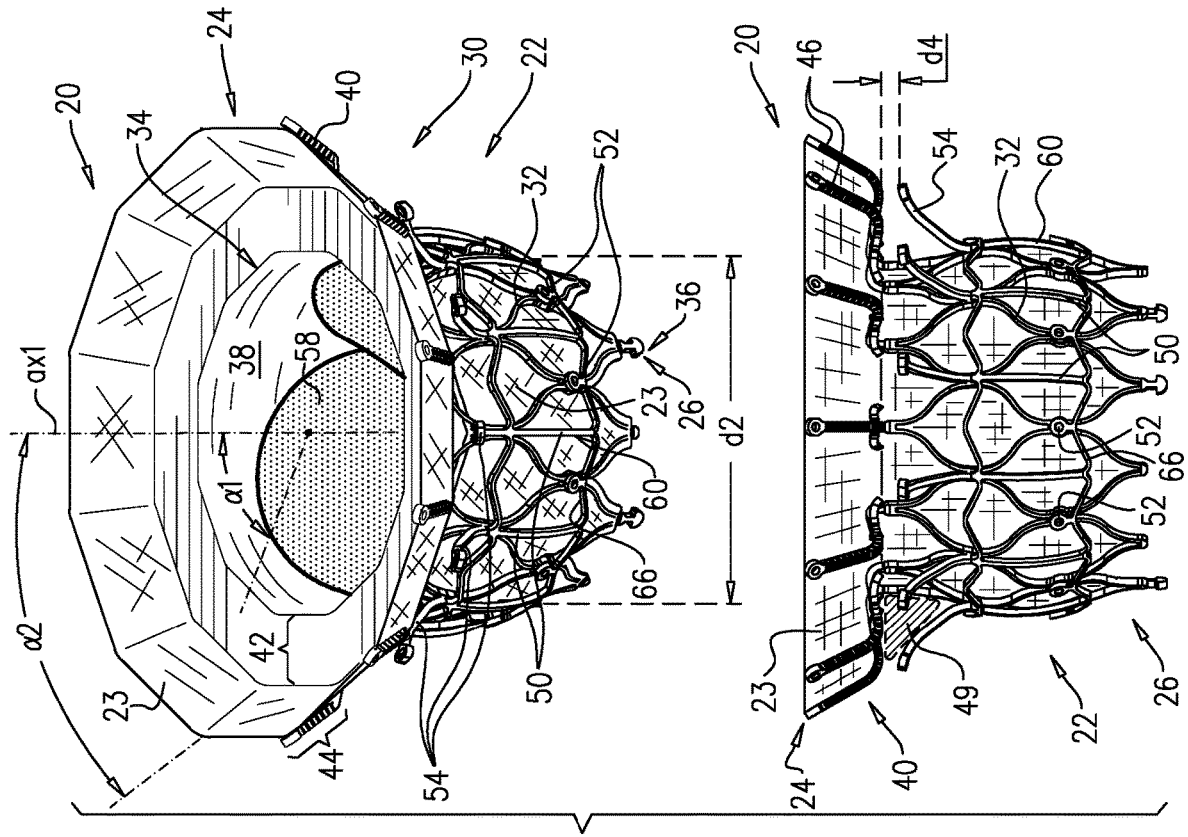

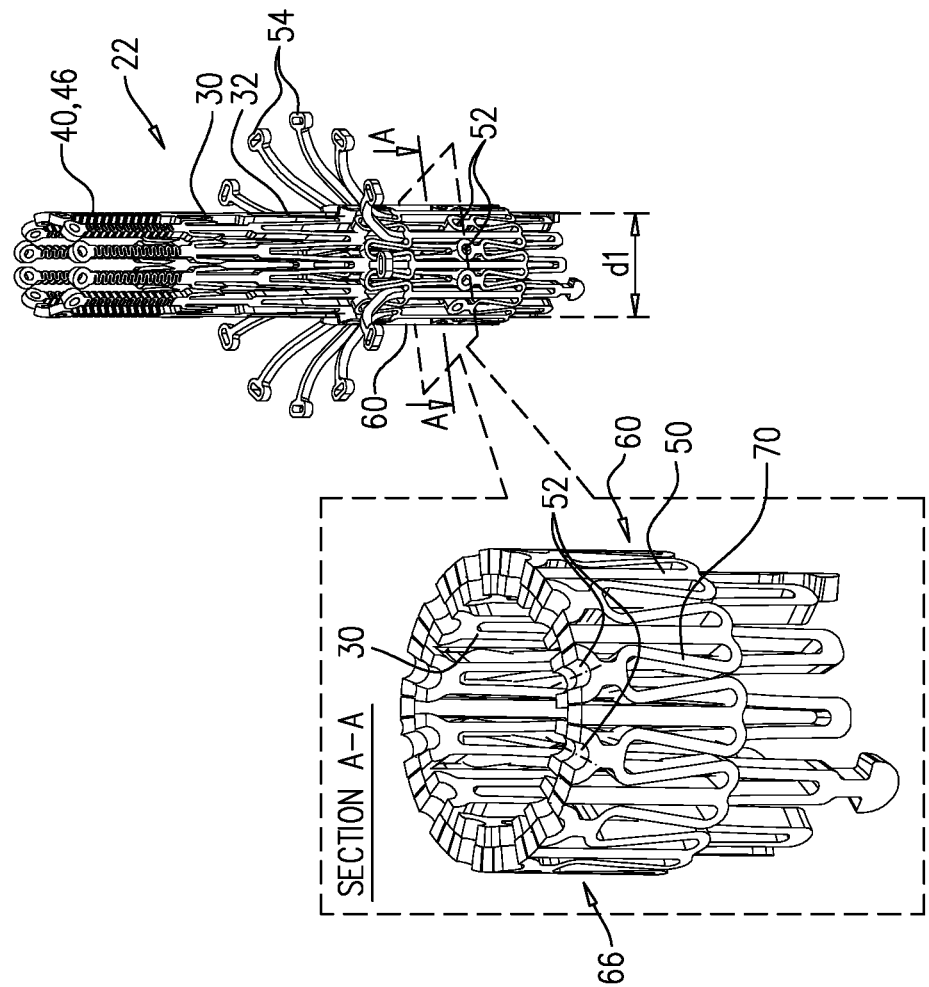
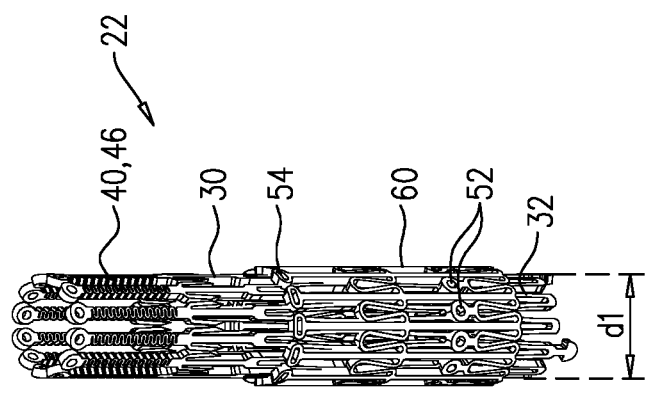
FIG. 2B
FIG. 2A

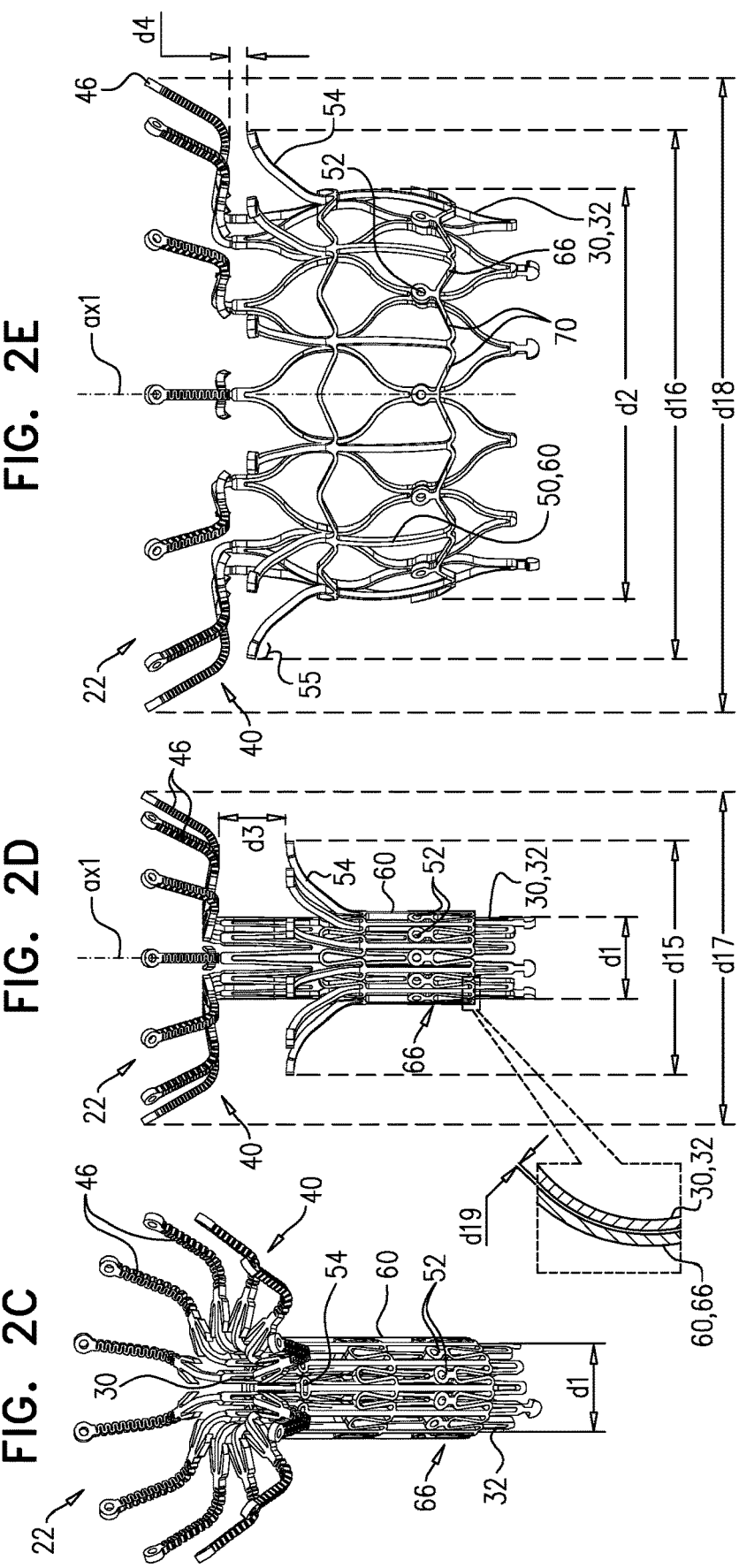

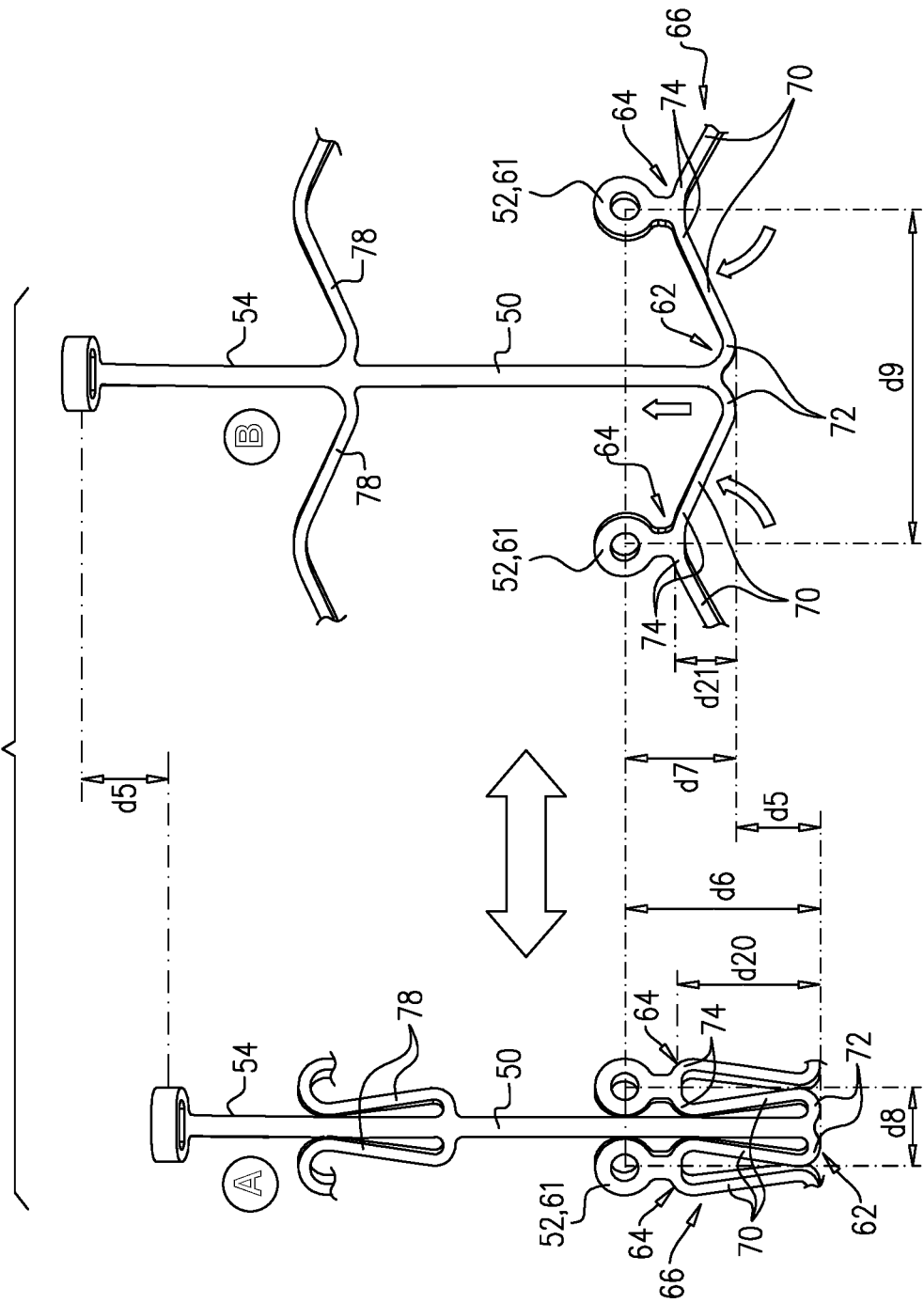

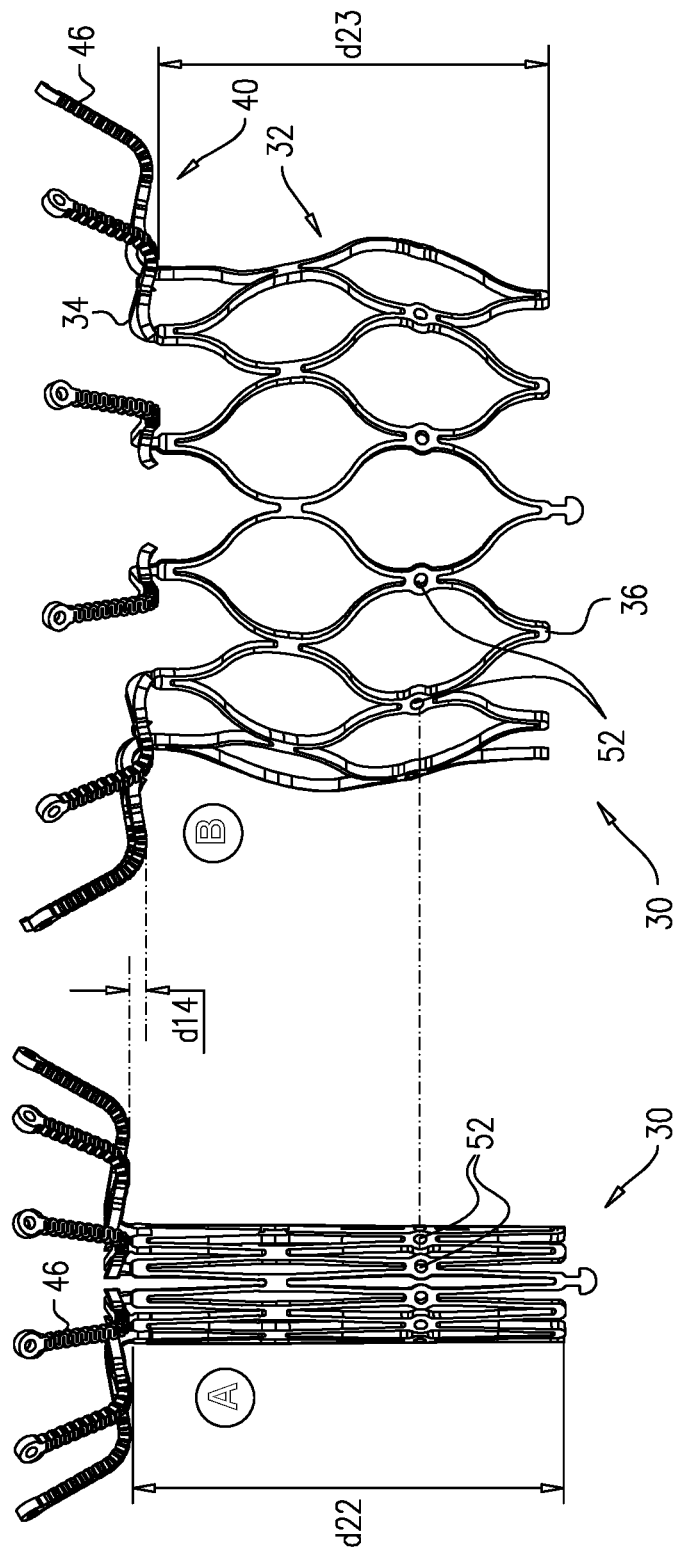

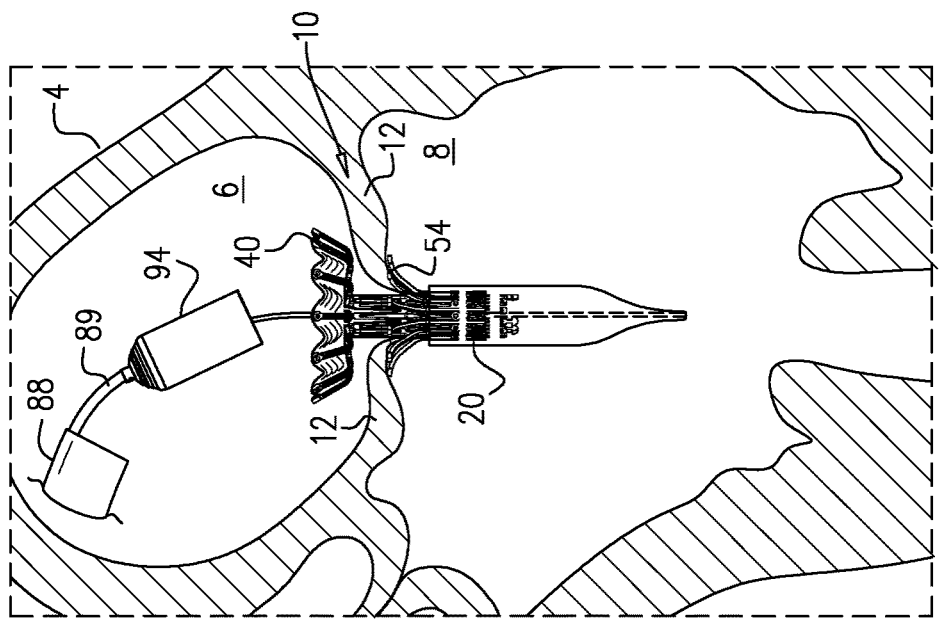
FIG. 4D
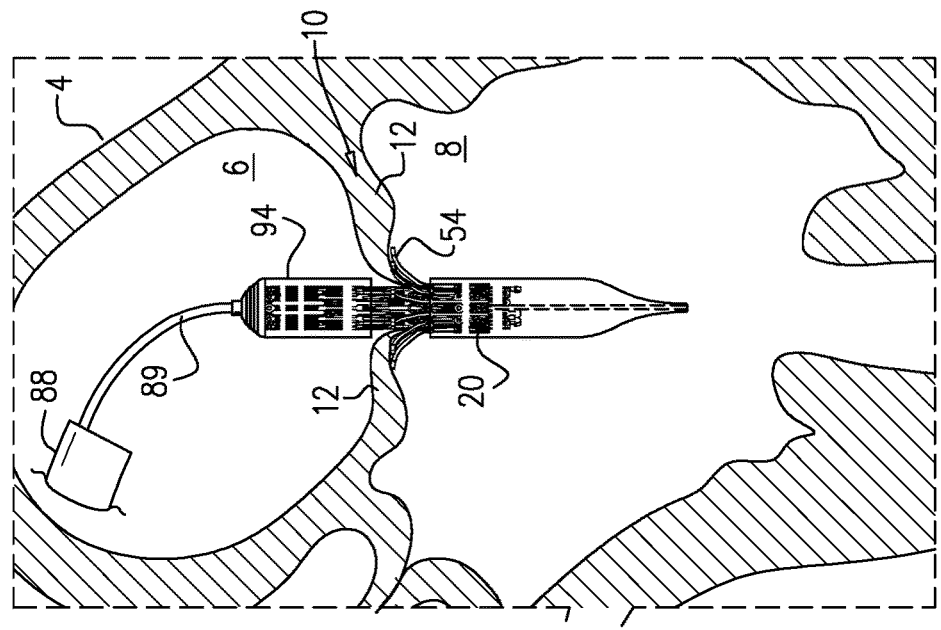
FIG. 4C
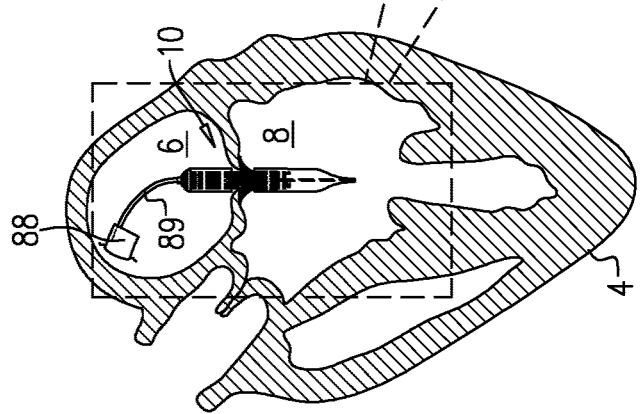

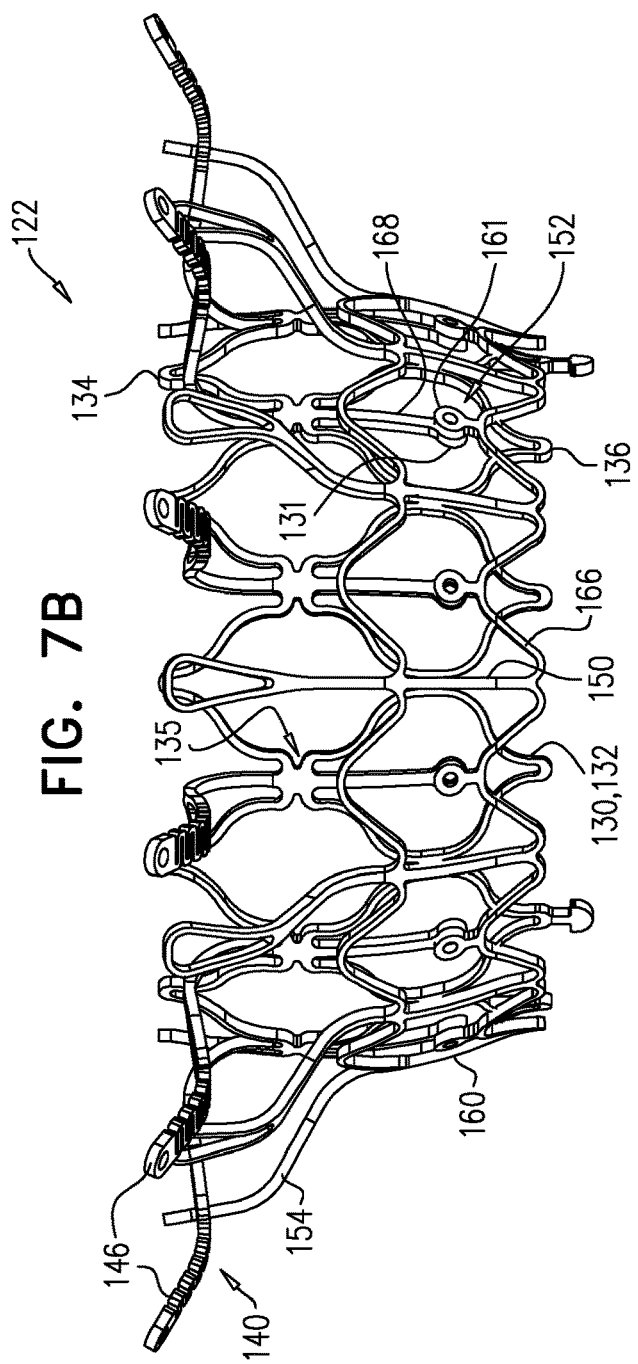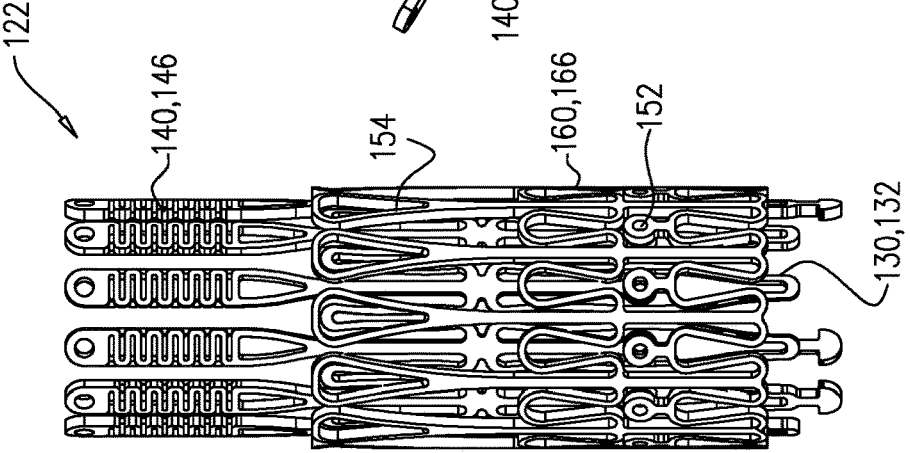

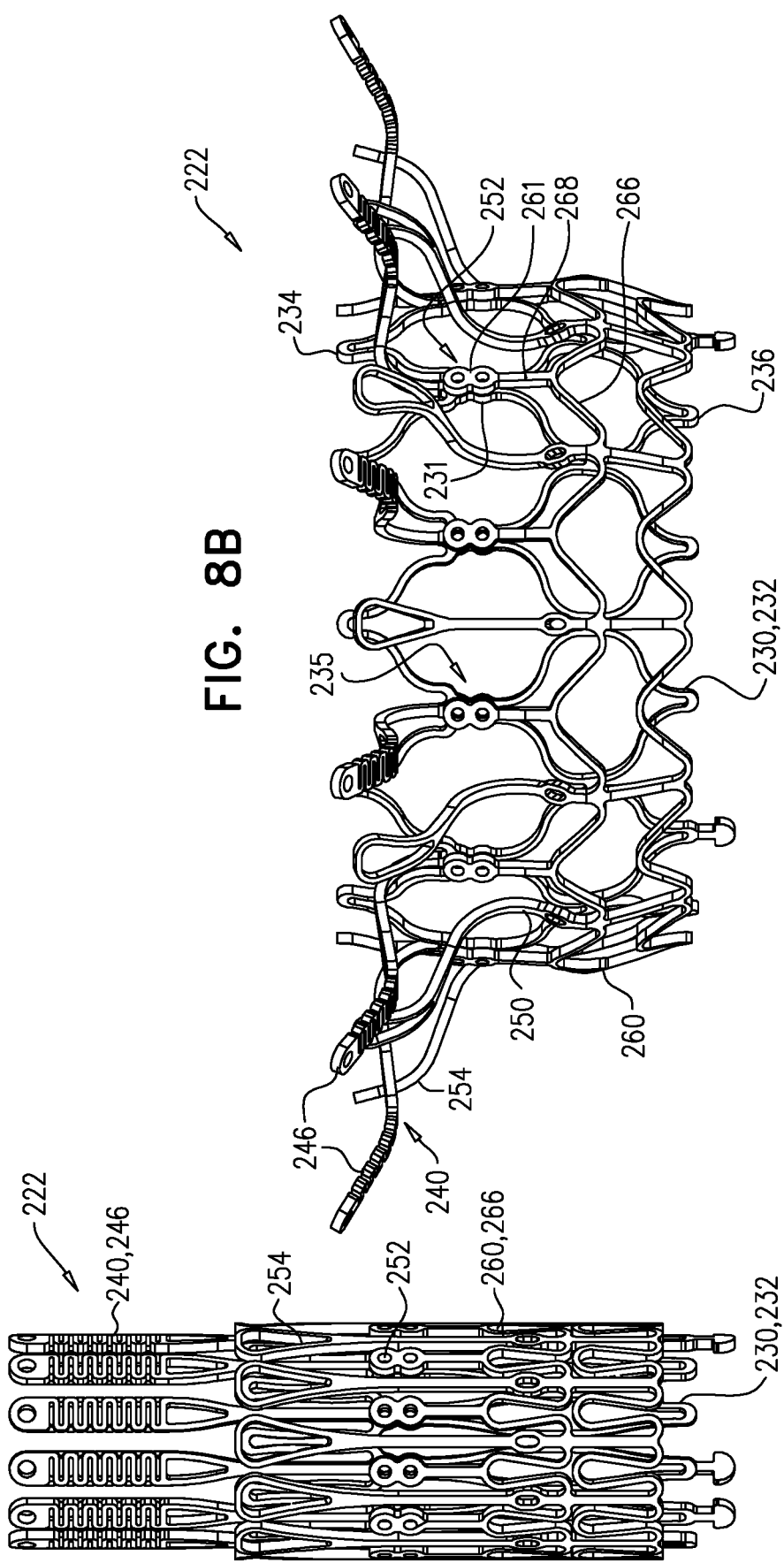

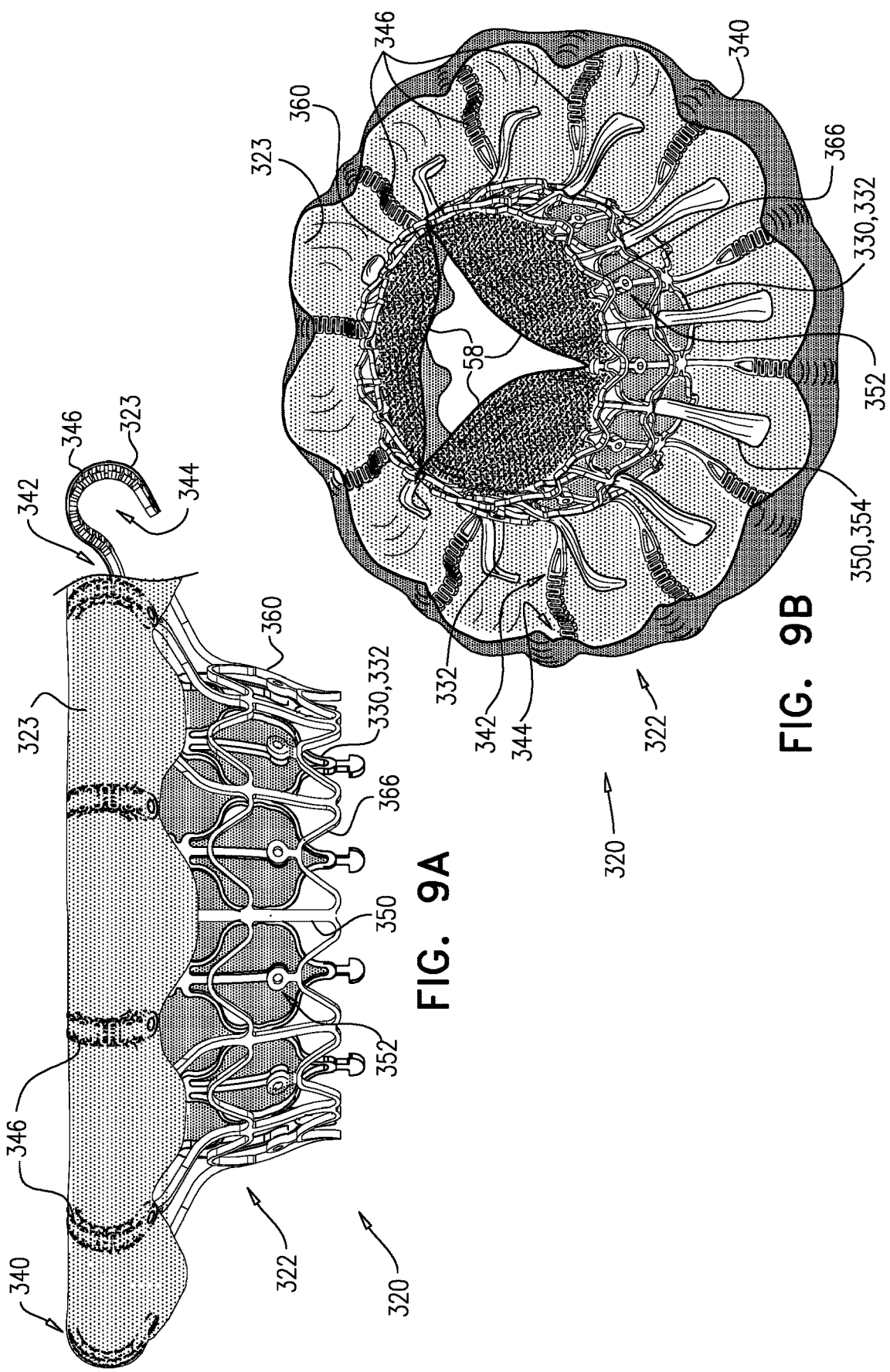

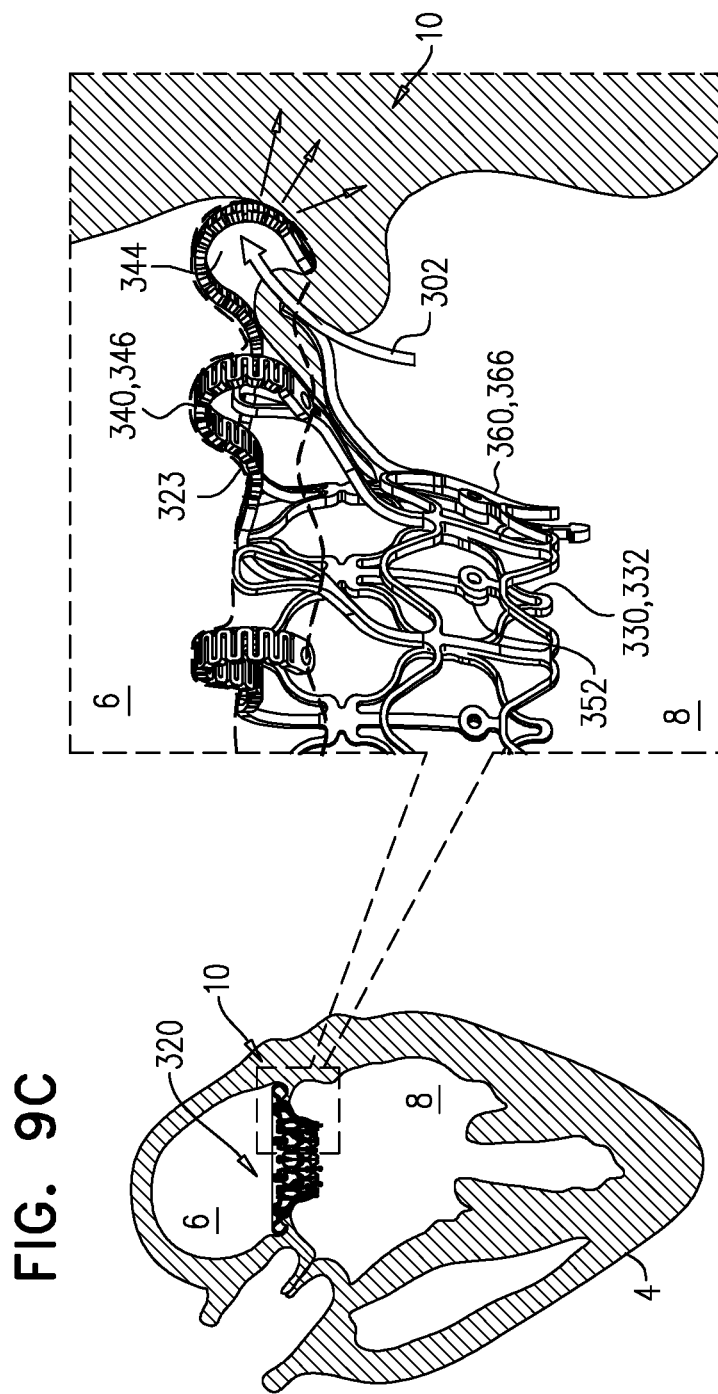

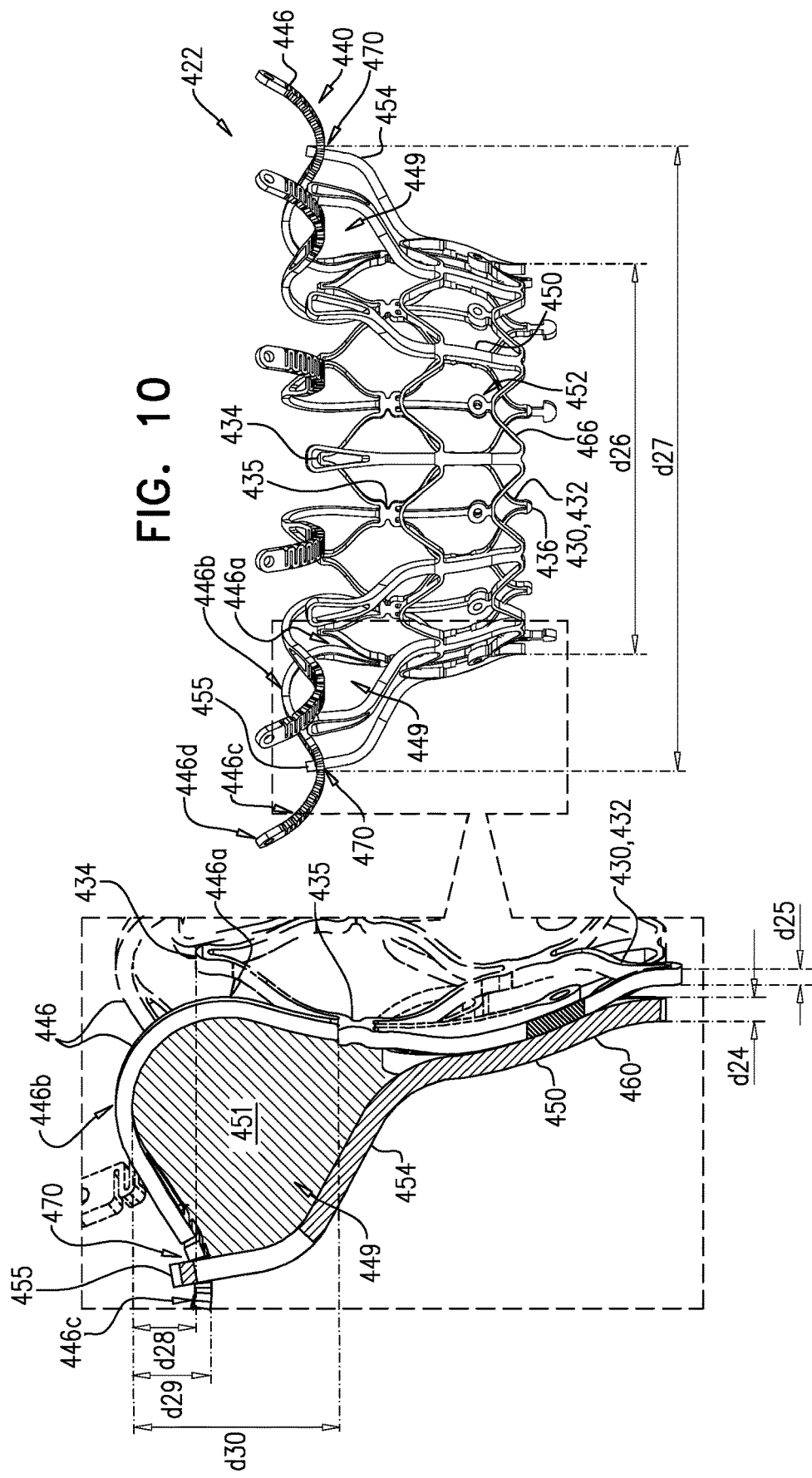

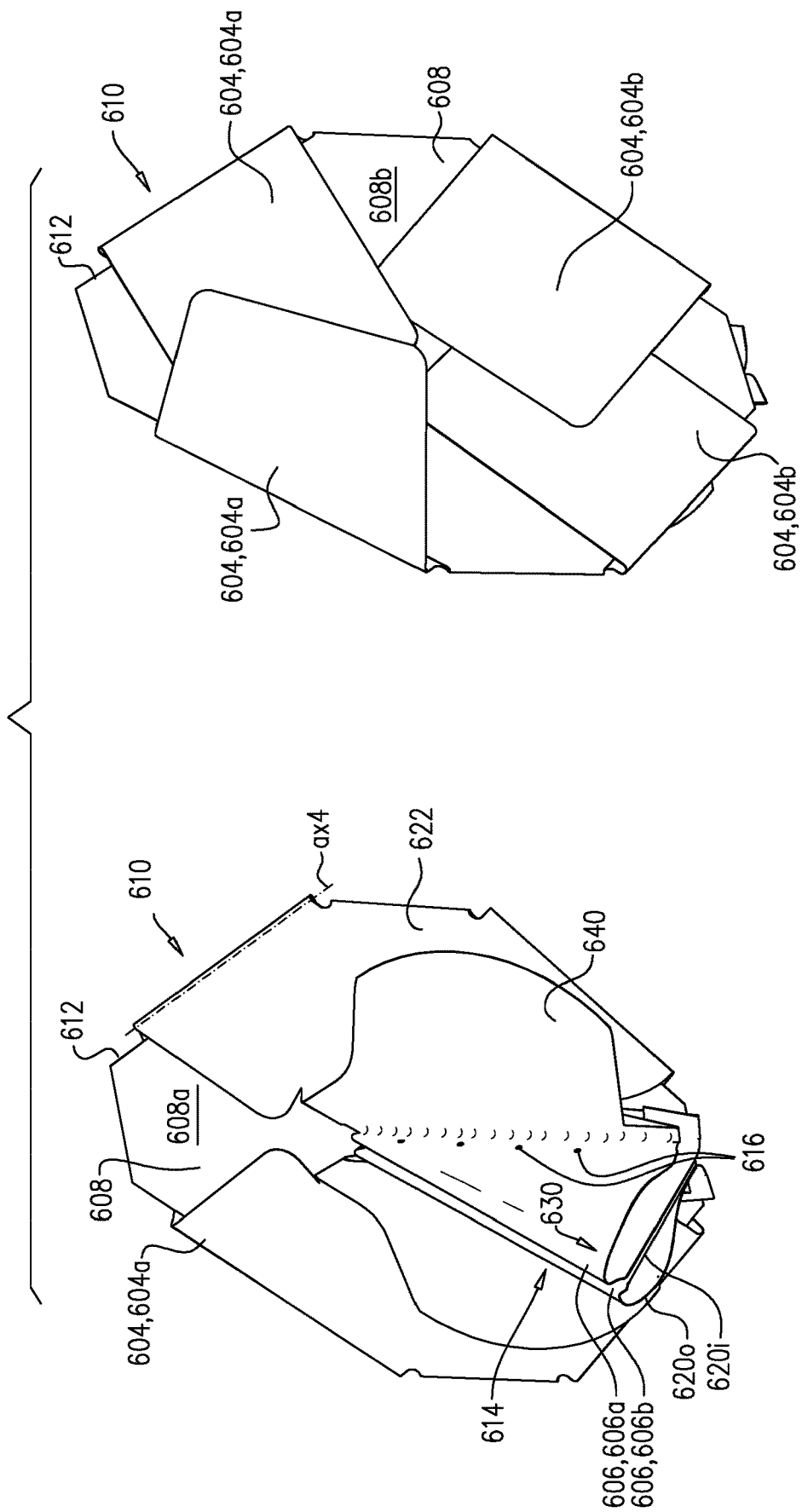

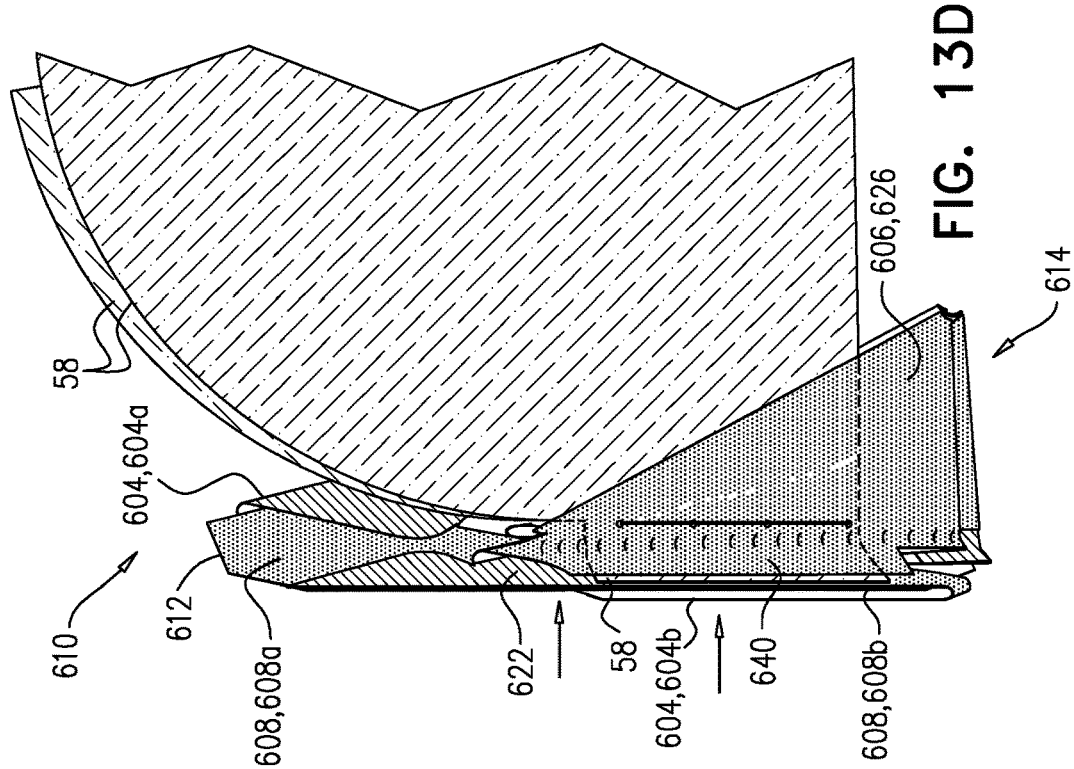
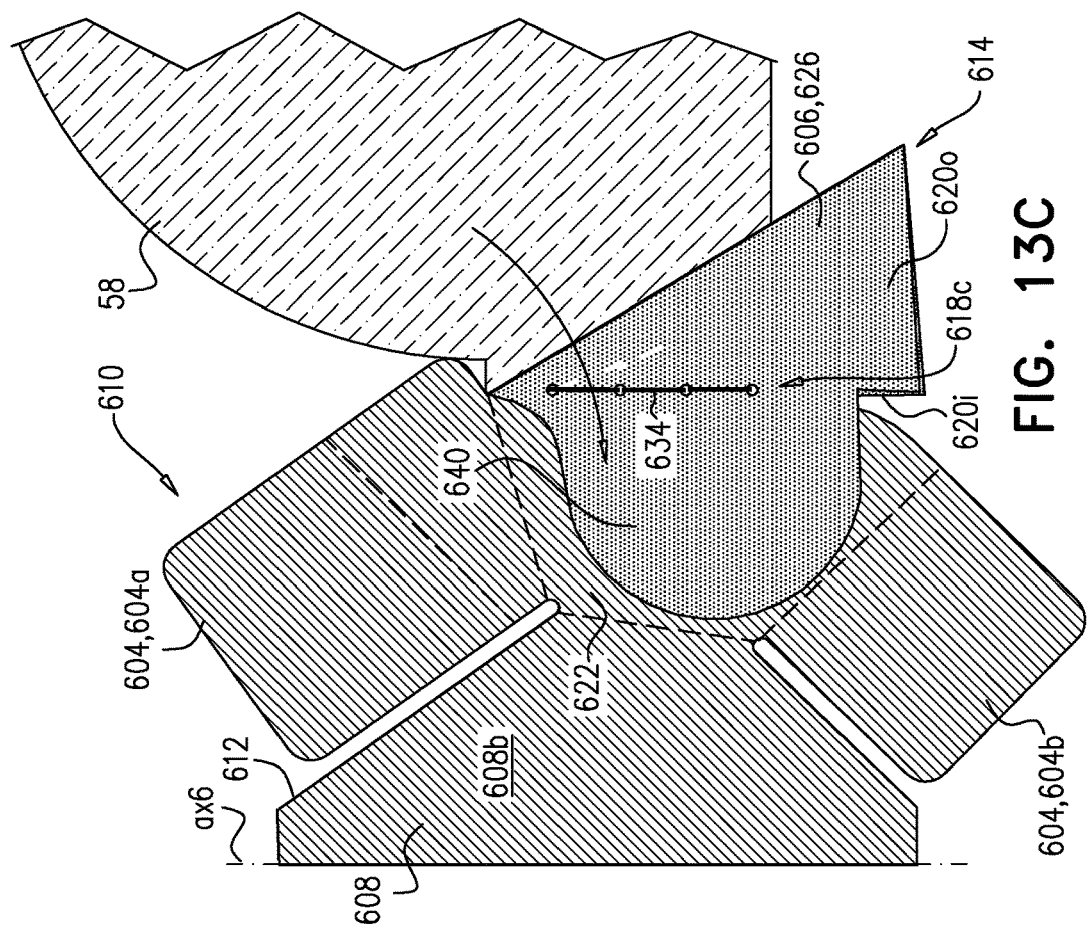

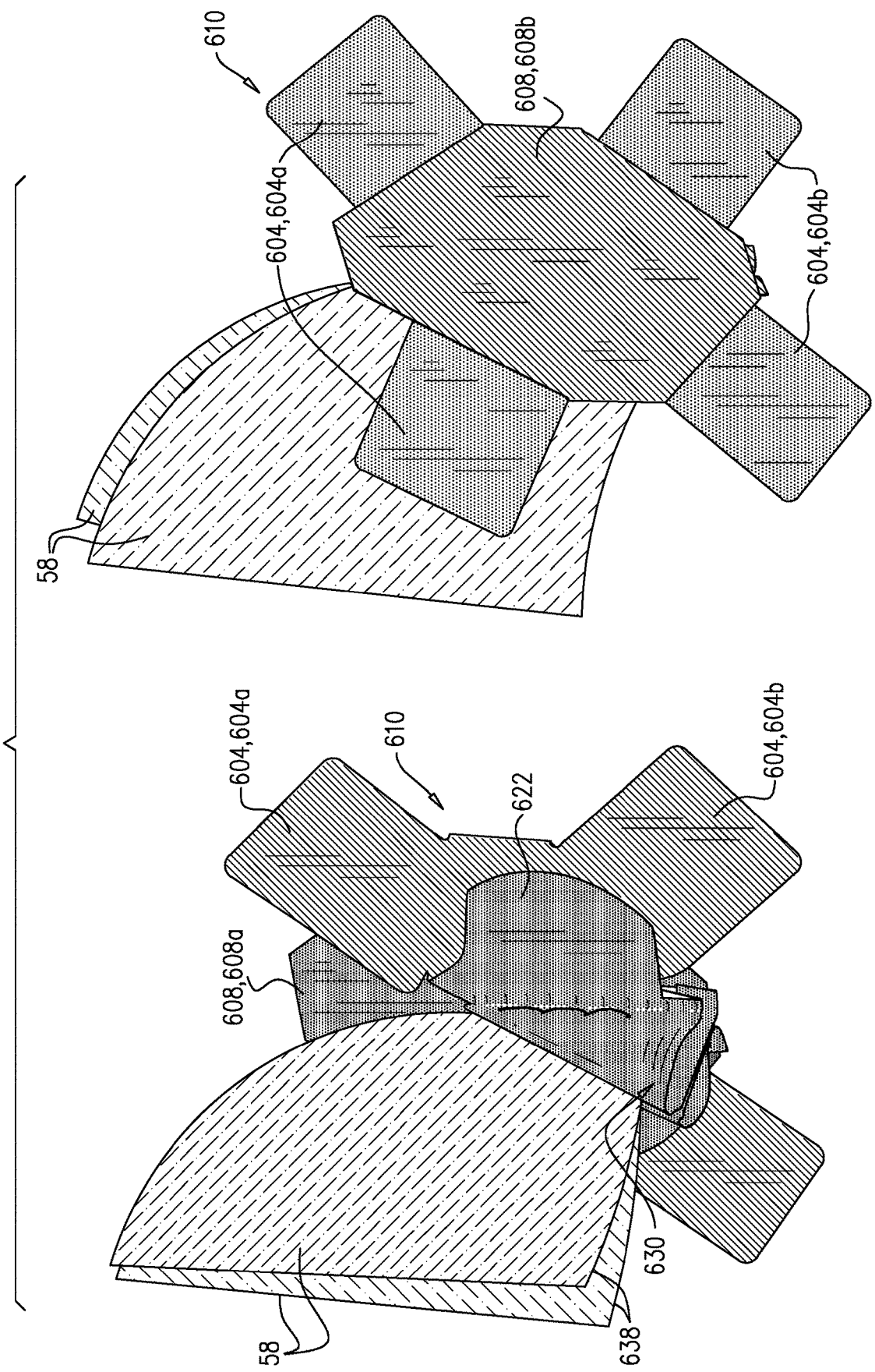

PROSTHETIC VALVE WITH CONCENTRIC FRAMES

CROSS-REFERENCES TO RELATED APPLICATIONS

This application is the US National Phase of International Patent Application PCT/IL2017/050873 to Hariton et al., filed Aug. 8, 2017, and entitled "Prosthetic valve with concentric frames," which published as WO 2018/029680, and which claims priority from U.S. provisional patent application 62/372,861 to Hariton et al., filed Aug. 10, 2016, and entitled "Prosthetic valve with concentric frames."

This application is related to U.S. patent application Ser. No. 15/541,783 to Hariton et al., now U.S. Pat. No. 9,974,651, which is the US National Phase of PCT application IL2016/050125 to Hariton et al., filed Feb. 3, 2016, which published as WO/2016/125160, and entitled "Prosthetic valve with axially-sliding frames."

All of the above applications are incorporated herein by reference.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, an implant is provided having a tubular portion, an upstream support portion and one or more flanges. The implant is assembled from two concentric frames. An inner frame defines the tubular portion and the upstream support portion, and an outer frame defines the flanges. The implant is percutaneously deliverable to a native heart valve in a compressed state, and is expandable at the native valve. The implant is secured at a native heart valve by sandwiching tissue of the native valve between the upstream support portion and the flanges.

For some applications, the outer frame is radially thicker than the inner frame. For some applications, the outer frame is undersized with respect to the inner frame, such that it constrains the inner frame even in a relaxed expanded state of the implant, and such that even in the relaxed expanded state residual stress is present in one or both of the frames. For some applications, a toroidal space is defined by the tubular portion, the upstream support portion, and the flanges. For some such applications, the implant is configured such that the toroidal space is dimensioned proportionally to dimensions of the tubular portion.

There is therefore provided, in accordance with an application of the present invention, apparatus for use with a prosthetic valve, the apparatus including a connector, the connector including a flexible sheet that is folded to define:
a panel, having a first side facing in a first direction, and a second side that is opposite the first side;
a leaflet receptacle, disposed on the first side of the panel, and protruding in the first direction away from the panel; and
a plurality of flaps, each flap folded about a respective fold axis such that at least part of each flap is disposed on the second side of the panel.

In an application, the panel has an edge between the first side and the second side, and each flap is foldable over the edge, so as to be disposed on the second side of the panel.

In an application, the plurality of flaps is arranged in a circuit such that each flap has two adjacent flaps around the circuit, and the fold axis of each flap is oriented at 60-120 degrees from the fold axis of each of its adjacent flaps.

In an application, the flexible sheet is a single unitary flexible sheet, and the unitary flexible sheet is folded to define the panel, the leaflet receptacle, and the plurality of flaps.

In an application, the plurality of flaps includes exactly four flaps.

In an application:
the leaflet receptacle includes:
a first leaflet-engaging tab, extending from the first side of the panel, and defining a first row of first-tab stitching holes and a second row of first-tab stitching holes, and
a second leaflet-engaging tab, extending from the first side of the panel, and defining a first row of second-tab stitching holes and a second row of second-tab stitching holes;
the receptacle is configured to sandwich one or more prosthetic valve leaflets between the leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first row of first-tab stitching holes and the second row of first-tab stitching holes diverge at 10-45 degrees from each other, and the first row of second-tab stitching holes and the second row of second-tab stitching holes diverge at 10-45 degrees from each other.

In an application, the first row of first-tab stitching holes and the second row of first-tab stitching holes diverge at 10-30 degrees from each other, and the first row of second-tab stitching holes and the second row of second-tab stitching holes diverge at 10-30 degrees from each other.

In an application, the first row of first-tab stitching holes and the second row of first-tab stitching holes diverge at 15-25 degrees from each other, and the first row of second-tab stitching holes and the second row of second-tab stitching holes diverge at 15-25 degrees from each other.

In an application, the flexible sheet is folded such that each of the first leaflet-engaging tab and the second leaflet-engaging tab includes (i) an outer layer, and (ii) an inner layer that is positioned to be sandwiched between the outer layer and the one or more leaflets, and:
the first and second rows of first-tab stitching holes are defined in the inner layer of the first leaflet-engaging tab, and
the first and second rows of second-tab stitching holes are defined in the inner layer of the second leaflet-engaging tab.

In an application:
the first leaflet-engaging tab further defines a third row of first-tab stitching holes, defined in the outer layer of the first leaflet-engaging tab, and aligned with the first row of first-tab stitching holes, the second leaflet-engaging tab further defines a third row of second-tab stitching holes, defined in the outer layer of the second leaflet-engaging tab, and aligned with the first row of second-tab stitching holes.

In an application, the apparatus further includes:
a tubular frame that defines a lumen therethrough; and
a first prosthetic leaflet and a second prosthetic leaflet, the first and second prosthetic leaflets disposed within the lumen,
and the apparatus defines a commissure at which the first and second leaflets meet each other and are coupled to the frame via the connector.

In an application, the leaflets define an upstream end and a downstream end of the lumen by being arranged and coupled to the frame so as to facilitate one-way fluid flow through the lumen.

In an application:
the leaflet receptacle includes:
a first leaflet-engaging tab, extending from the first side of the panel, and
a second leaflet-engaging tab, extending from the first side of the panel; and
the first and second leaflets are sandwiched together between the first and second leaflet-engaging tabs, and are stitched to the first and second leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first leaflet has a first-leaflet downstream edge, and the second leaflet has a second-leaflet downstream edge, and each of the first and second leaflet-engaging tabs extends in a downstream direction beyond the first-leaflet downstream edge and the second-leaflet downstream edge.

In an application:
the first leaflet has a first-leaflet downstream edge, and the second leaflet has a second-leaflet downstream edge,
the first and second leaflets are configured:
to inhibit fluid flow in an upstream direction by the first and second leaflets moving toward each other in response to the fluid flow in an upstream direction, such that the first-leaflet downstream edge and the second-leaflet downstream edge move away from the frame, and
to facilitate fluid flow in a downstream direction by the first and second leaflets moving away from each other in response to the fluid flow in a downstream direction, such that the first-leaflet downstream edge and the second-leaflet downstream edge move toward the frame,
the first leaflet-engaging tab defines a first cushion that inhibits movement of a commissural portion of the first leaflet toward the frame, and
the second leaflet-engaging tab defines a second cushion that inhibits movement of a commissural portion of the second leaflet toward the frame.

In an application, the first cushion and the second cushion are disposed further downstream than the first-leaflet downstream edge and the second-leaflet downstream edge.

In an application, the first and second cushions are each defined by folds in the flexible sheet.

In an application:
the leaflet receptacle includes:
a first leaflet-engaging tab, extending from the first side of the panel, and defining a first row of first-tab stitching holes and a second row of first-tab stitching holes, and
a second leaflet-engaging tab, extending from the first side of the panel, and defining a first row of second-tab stitching holes and a second row of second-tab stitching holes; and
the first and second leaflets are sandwiched together between the first and second leaflet-engaging tabs, and are stitched to the first and second leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first and second rows of first-tab stitching holes diverge from each other such that progressively downstream parts of the first and second rows of first-tab stitching holes are progressively further from each other, and the first and second rows of second-tab stitching holes diverge from each other such that progressively downstream parts of the first and second rows of second-tab stitching holes are progressively further from each other.

In an application, the first and second rows of first-tab stitching holes diverge at 10-45 degrees from each other, and the first and second rows of second-tab stitching holes diverge at 10-45 degrees from each other.

In an application:
the connector is a first connector,
the commissure is a first commissure,
the apparatus further includes a second connector, a third connector, and a third leaflet, and
the apparatus defines:
a second commissure at which the second and third leaflets meet each other and are coupled to the frame via the second connector, and
a third commissure at which the third and first leaflets meet each other and are coupled to the frame via the third connector.

In an application, the fold axis of each flap is oriented at 70-110 degrees from the fold axis of each of its adjacent flaps.

In an application, the fold axis of each flap is oriented at 80-100 degrees from the fold axis of each of its adjacent flaps.

In an application, the connector has a folded state in which the sheet is folded to define the panel, the leaflet receptacle, and the plurality of flaps, and the sheet further has an unfolded state in which the sheet defines a plane, and further defines, in the plane:
the panel, at a medial region of the sheet,
the flaps, disposed peripherally to the panel,
a first tab portion and a second tab portion, each of the tab portions disposed peripherally from the panel,
and in the folded state, each of the tab portions defines a respective leaflet-engaging tab, and the leaflet receptacle includes the leaflet-engaging tab of each of the tab portions.

In an application, in the folded state, a first flap part of each of the flaps is disposed on the first side of the panel, and each of the flaps is folded around the panel such that a second flap part of each of the flaps is disposed on the second side of the panel.

In an application, the sheet further defines a first bridging element via which the first tab portion is connected to the panel, and a second bridging element via which the second tab portion is connected to the panel.

In an application, in the folded state, the first and second bridging elements extend from respective edges of the panel and toward each other across the first side of the panel, and each of the first and second tab portions protrudes from the respective bridging element in the first direction away from the first side of the panel.

In an application, the flaps are connected to the panel independently of the bridging elements.

In an application, the flaps are connected to the panel via the bridging elements.

In an application, in the unfolded state:

the panel, the first and second bridging elements, and the first and second tab portions are arranged in a row that defines a lateral axis in the plane, the lateral axis passing through the panel, the first and second bridging elements, and the first and second tab portions, and for each of the bridging elements, a first flap of the plurality of flaps and a second flap of the plurality of flaps are connected to the bridging element, the lateral axis passing between the first and second flaps.

In an application, in the folded state, the bridging elements are disposed on the first side of the panel, and each flap extends from one of the bridging elements and around the panel such that a flap part of each flap is disposed on the second side of the panel.

In an application, in the unfolded state, the first tab portion and the second tab portion flank the panel by being disposed, in the plane, on opposing lateral sides of the panel.

In an application, in the unfolded state, the first and second tab portions, the first and second bridging elements, and the panel are arranged in a row that defines a lateral axis in the plane, and the fold axis of each of the flaps is at 30-60 degrees from the lateral axis.

There is further provided, in accordance with an application of the present invention, apparatus for use with a prosthetic valve, the apparatus including a connector, the connector comping:

a panel, having a first side that faces in a first direction, and a second side that faces in a second, opposite direction;

a leaflet-engaging tab, protruding from the first side in the first direction; and a plurality of flaps, each flap extending from the panel, and configured to fold, over a respective fold axis, toward the second direction, the plurality of flaps arranged in a circuit such that each flap has two adjacent flaps around the circuit, and:

the fold axis of each flap is oriented at 60-120 degrees from the fold axis of each of its adjacent flaps.

In an application, the panel substantially defines a plane, and each flap is configured to fold, over its respective fold axis, out of the plane.

In an application, each flap is configured to fold over a respective portion of the second side of the panel.

In an application, the connector consists of a single unitary sheet of a material that is folded to define the panel, the leaflet-engaging tab, and the plurality of flaps.

In an application, the plurality of flaps includes exactly four flaps.

In an application, the fold axis of each flap is oriented at 70-110 degrees from the fold axes of its adjacent flaps.

In an application, the fold axis of each flap is oriented at 80-100 degrees from the fold axes of its adjacent flaps.

In an application, the fold axis of each flap is oriented at approximately 90 degrees from the fold axes of its adjacent flaps.

There is further provided, in accordance with an application of the present invention, a method, including:

folding a flexible sheet to define a connector having:
a panel, having a first side facing in a first direction, and a second side that is opposite the first side;
a leaflet receptacle, disposed on the first side of the panel, and protruding in the first direction away from the panel; and
a plurality of flaps, each flap folded about a respective fold axis such that at least part of each flap is disposed on the second side of the panel;

attaching one or more leaflets to the connector by stitching the one or more leaflets to the leaflet receptacle; and attaching the connector to a frame assembly by folding each flap of the plurality of flaps around a respective component of the frame assembly, and securing them by stitching.

There is further provided, in accordance with an application of the present invention, apparatus for use at a heart valve of a subject, the apparatus including:

a frame assembly, transluminally advanceable to the heart, and including:
an inner stent frame that defines a tubular portion; and
an outer stent frame that defines a ring that is coupled to the inner stent frame, and circumscribes the tubular portion; and a plurality of prosthetic valve leaflets, coupled to the frame assembly and disposed in the tubular portion, and the inner stent frame is cut from a first tube of nitinol that has a first-tube wall thickness, and the outer stent frame is cut from a second tube of nitinol that has a second-tube wall thickness that is greater than the first-tube wall thickness.

In an application, the first-tube wall thickness is 0.45-0.65 mm, and the second-tube wall thickness is 0.6-0.8 mm.

In an application, the second-tube wall thickness is at least 20 percent greater than the first-tube wall thickness.

In an application, the second-tube wall thickness is at least 30 percent greater than the first-tube wall thickness.

In an application:

the inner frame further defines an annular upstream support portion, extending from the tubular portion, and dimensioned to be placed against an upstream surface of the heart valve, and the outer frame further defines a plurality of flanges that extend from the tubular portion, and are dimensioned to be placed against a downstream surface of the heart valve.

There is further provided, in accordance with an application of the present invention, apparatus for use with a heart of a subject, the apparatus including:

an inner stent frame that:
defines a tubular portion and a plurality of inner-frame coupling elements, and
has a relaxed expanded state in which the tubular portion defines an inner-stent-frame relaxed expanded diameter; and an outer stent frame, that:
defines a ring and a plurality of outer-frame coupling elements, and has a relaxed expanded state in which the ring defines an outer-stent-frame relaxed expanded diameter that is smaller than the inner-stent-frame expanded diameter, and:

together, the inner stent frame and the outer stent frame define at least part of a frame assembly in which the outer-frame coupling elements are fixed to the inner-frame coupling elements and the ring circumscribes the tubular portion, and the frame assembly:

further includes a plurality of prosthetic leaflets secured to, and disposed within, the tubular portion, has a compressed state in which the frame assembly is transluminally advanceable to the heart, and is expandable into an expanded state in which the tubular portion defines an inner-stent-frame constrained expanded diameter that is smaller than the inner-stent-frame relaxed expanded diameter.

In an application, the outer frame is coupled to the inner frame such that:

in the compressed state of the frame assembly, the outer frame is in circumferential contact with the tubular portion, and throughout expansion of the frame assembly into its expanded state, circumferential contact is maintained between the outer frame and the tubular portion.

In an application, the outer-frame coupling elements are welded to the inner-frame coupling elements.

In an application:

the apparatus defines a plurality of commissures at which the leaflets are secured to the frame assembly, and the outer frame is secured to the inner frame by both (i) the fixation of the outer-frame coupling elements to the inner-frame coupling elements, and (ii) stitching of the outer frame to the inner frame at the commissures.

In an application:

the apparatus defines a plurality of commissures, at each of the commissures, the apparatus includes a plurality of stitches, and commissural portions of the two prosthetic leaflets are secured to the inner stent frame and to the outer stent frame via the plurality of stitches.

In an application, at each commissure the apparatus includes a fabric connector to which the commissural portions of the two leaflets are secured, and the plurality of stitches secures the commissural portions of the two leaflets to the inner stent frame and the outer stent frame by being attached to the fabric connector.

In an application, the fabric connector is shaped to define (i) a panel having a first side and a second side, (ii) one or more leaflet-engaging tabs to which the commissural portions of the two leaflets are stitched, the tabs protruding from the first side of the panel, and (iii) a plurality of flaps, wrapped around elements of the inner stent frame and elements of the outer stent frame, and secured thus by stitching.

There is further provided, in accordance with an application of the present invention, apparatus for use in a heart of a subject, the apparatus including:

a frame assembly defining:

a tubular portion that defines a longitudinal lumen therethrough, an upstream support portion, coupled to the tubular portion, and a plurality of flanges, coupled to the tubular portion; and a plurality of prosthetic valve leaflets, coupled to the tubular portion, and disposed within the lumen, and:

the frame assembly:

has a compressed state for transluminal delivery to the heart, and has an expanded state, in which:

the upstream support portion extends radially outward from the tubular portion, the flanges extend radially outward from the tubular portion and toward the upstream support portion, the tubular portion has a transverse cross-sectional area, and the frame assembly defines a toroidal space between the flanges, the upstream support portion, and the tubular portion, the toroidal space circumscribing the tubular portion and having a cross-sectional area that is 5-10 percent of the transverse cross-sectional area of the tubular portion.

In an application:

the frame assembly is a first frame assembly, the plurality of leaflets is a first plurality of leaflets, and the apparatus includes a first implant that includes the first frame assembly and the first plurality of leaflets, and the apparatus further includes a second implant that includes:

a second frame assembly defining:

a second tubular portion that defines a second longitudinal lumen therethrough, a second upstream support portion, coupled to the second tubular portion, and a second plurality of flanges, coupled to the second tubular portion; and a second plurality of prosthetic valve leaflets, coupled to the second tubular portion, and disposed within the second lumen, and:

the second frame assembly:

has a compressed state for transluminal delivery to the heart, and has an expanded state, in which:

the second upstream support portion extends radially outward from the second tubular portion; and the flanges of the second plurality of flanges extend radially outward from the second tubular portion and toward the second upstream support portion, the second tubular portion has a transverse cross-sectional area that is at least 30 percent greater than the transverse cross-sectional area of the first tubular portion of the first implant, and the second frame assembly defines a second toroidal space between the flanges of the second plurality of flanges, the second upstream support portion, and the second tubular portion, the second toroidal space circumscribing the second tubular portion and having a cross-sectional area that is 5-10 percent of the transverse cross-sectional area of the second tubular portion.

In an application, the frame assembly is dimensioned such that the cross-sectional area of the toroidal space is 5-8 percent of the transverse cross-sectional area of the tubular portion.

In an application, the frame assembly is dimensioned such that the cross-sectional area of the toroidal space is 6-7 percent of the transverse cross-sectional area of the tubular portion.

In an application, the frame assembly is dimensioned such that the cross-sectional area of the toroidal space is 6.5-7.5 percent of the transverse cross-sectional area of the tubular portion.

In an application, the upstream support portion includes a plurality of arms that, in the expanded state of the frame assembly, protrude radially outward from the tubular portion.

In an application:

the tubular portion has an upstream end and a downstream end, the prosthetic leaflets are configured to provide one-way blood flow through the lumen from the upstream end to the downstream end, each arm of the plurality of arms is attached to the tubular portion at a site that is downstream of the upstream end, progressively lateral portions of each arm define, respectively:

an ascending portion that extends in an upstream direction past the upstream end of the tubular portion, an arch portion that curves in a downstream direction to form an arch, and a lateral portion that curves in an upstream direction.

In an application, the frame assembly defines the toroidal space between the flanges, the tubular portion, and the arch portions of the arms of the upstream support portion.

In an application, each flange extends radially outward from the tubular portion and toward a tip of the flange, and the arch portion of the arms curves in a downstream direction past the tips of the flanges.

There is further provided, in accordance with an application of the present invention, apparatus for use at a heart valve of a subject, the apparatus including:

a first implant and a second implant, each implant being transluminally advanceable to the heart, and including:

a frame assembly that includes:

an inner stent frame that defines a tubular portion that defines a lumen; and an outer stent frame that defines a ring that is coupled to the inner stent frame, and circumscribes the tubular portion; and a plurality of prosthetic valve leaflets, coupled to the frame assembly and disposed in the tubular portion; and a delivery tool, including a delivery capsule that has a capsule diameter, and:

the first implant has:

an expanded state in which its lumen has a lumen diameter, and a compressed state in which the first implant has a compressed diameter, and is dimensioned to be housed within the delivery capsule, and the second implant has:

an expanded state in which its lumen has a lumen diameter that is at least 15 percent greater than the lumen diameter of the first implant, and a compressed state in which the second implant has a compressed diameter that is no more than 2 percent greater than the compressed diameter of the first implant, and is dimensioned to be housed within the delivery capsule.

There is further provided, in accordance with an application of the present invention, apparatus for use with a native valve that is disposed between an atrium and a ventricle of a heart of a subject, the apparatus including:

a valve frame, including a tubular portion that circumscribes a longitudinal axis of the valve frame so as to define a lumen along the axis, the tubular portion defining a plurality of valve-frame coupling elements disposed circumferentially around the longitudinal axis;

a plurality of prosthetic leaflets, coupled to the frame, disposed within the lumen, and arranged to provide unidirectional flow of blood from an upstream end of the lumen to a downstream end of the lumen;

an outer frame:

including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs, including a plurality of legs, each of the legs coupled to the ring at a respective trough, and shaped to define a plurality of outer-frame coupling elements, each of the outer-frame coupling elements (i) coupled to the ring at a respective peak, and (ii) fixed with respect to a respective valve-frame coupling element, and:

the tubular portion has (i) a compressed state in which the tubular portion has a compressed diameter, and (ii) an expanded state in which the tubular portion has an expanded diameter that is greater than the compressed diameter, and the fixation of the outer-frame coupling elements to the valve-frame coupling elements is such that compression of the tubular portion from the expanded state toward the compressed state such that the valve-frame coupling elements pull the outer-frame coupling elements radially inward: (i) reduces a circumferential distance between each of the outer-frame coupling elements and its adjacent outer-frame coupling elements, and (ii) increases the amplitude of the pattern of the ring.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the expanded state of the tubular portion is a constrained expanded state, and the fixation of the outer-frame coupling elements to the valve-frame coupling elements is such that, in a relaxed expanded state of the apparatus, the outer frame constrains the tubular portion in the constrained expanded state.

In an application, the apparatus further includes an upstream support portion that includes a plurality of arms coupled to the tubular portion, and:

the upstream support portion has (i) a constrained-arm state, and (ii) a released-arm state in which the arms extend radially outward from the tubular portion, each leg has a tissue-engaging flange that has (i) a constrained-flange state, and (ii) a released-flange state in which the flange extends radially outward from the tubular portion and toward the upstream support portion, and in a relaxed expanded state of the apparatus, in which (i) the tubular portion is in its expanded state, (ii) the upstream support portion is in its released-arm state, and (iii) the flanges are in the released-flange state:

the tubular portion has a transverse cross-sectional area, and the frame assembly defines a toroidal space between the flanges, the upstream support portion, and the tubular portion, the toroidal space circumscribing the tubular portion and having a cross-sectional area that is 5-10 percent of the transverse cross-sectional area of the tubular portion.

In an application, the ring circumscribes the tubular portion.

In an application, the valve-frame coupling elements are disposed circumferentially around the longitudinal axis between the upstream end and the downstream end but not at the upstream end nor at the downstream end.

In an application, the upstream support portion includes one or more fabric pockets disposed circumferentially, each pocket of the one or more pockets having an opening that faces a downstream direction.

In an application, the outer frame is coupled to the valve frame only via the fixation of the outer-frame coupling elements to the respective valve-frame coupling elements.

In an application, the apparatus further includes an upstream support portion that includes a plurality of arms that extend radially from the tubular portion, and:
the upstream support portion has (i) a constrained-arm state, and (ii) a released-arm state in which the arms extend radially outward from the tubular portion,
each leg has a tissue-engaging flange that has (i) a constrained-flange state, and (ii) a released-flange state in which the flange extends radially outward from the tubular portion, and
the apparatus has an intermediate state in which (i) the tubular portion is in its compressed state, (ii) the upstream support portion is in its released-arm state, and (iii) the legs are in their released-flange state.

In an application:
the apparatus includes an implant that includes the valve frame, the leaflets, and the outer frame, and
the apparatus further includes a tool:
including a delivery capsule dimensioned (i) to house and retain the implant in a compressed state of the implant in which (a) the tubular portion is in its compressed state, (b) the upstream support portion is in its constrained-arm state, and (c) the legs are in their constrained-flange state, and (ii) to be advanced percutaneously to the heart of the subject while the implant is housed and in its compressed state, and
operable from outside the subject to:
transition the implant from its compressed state into the intermediate state while retaining the tubular portion in its compressed state, and
subsequently, expand the tubular portion toward its expanded state.

In an application, the tool is operable from outside the subject to transition the implant from its compressed state into the intermediate state by (i) releasing the legs into their released-flange state, while retaining the tubular portion in its compressed state, and (ii) subsequently, releasing the upstream support portion into its released-arm state, while retaining the tubular portion in its compressed state.

In an application, the tool is operable from outside the subject to transition the implant from its compressed state into the intermediate state by (i) releasing the upstream support portion into its released-arm state, while retaining the tubular portion in its compressed state, and (ii) subsequently, releasing the legs into their released-flange state, while retaining the tubular portion in its compressed state.

In an application, the fixation of the outer-frame coupling elements to the valve-frame coupling elements is such that, when the apparatus is in its intermediate state, expansion of the tubular portion from its compressed state toward its expanded state moves the flanges longitudinally away from the valve-frame coupling elements.

In an application, the fixation of the outer-frame coupling elements to the valve-frame coupling elements is such that, when the apparatus is in its intermediate state, expansion of the tubular portion from its compressed state toward its expanded state reduces the amplitude of the pattern of the ring and passes the flanges between the arms.

In an application, the upstream support portion further includes a covering that covers the arms to form an annular shape in the released-arm state, and, when the apparatus is in its intermediate state, expansion of the tubular portion from its compressed state toward its expanded state presses the flanges onto the covering.

In an application, in the compressed state of the tubular portion, a downstream end of each leg is longitudinally closer than the valve-frame coupling elements to the downstream end, and the flange of each leg is disposed longitudinally closer than the valve-frame coupling elements to the upstream end.

In an application, in the expanded state of the tubular portion, the downstream end of each leg is longitudinally closer than the valve-frame coupling elements to the downstream end, and the flange of each leg is disposed longitudinally closer than the valve-frame coupling elements to the upstream end.

There is further provided, in accordance with an application of the present invention, apparatus for use with a native valve of a heart of a subject, the apparatus including an implant that includes:
a valve frame that includes a tubular portion that circumscribes a longitudinal axis of the valve frame so as to define a lumen along the axis, the tubular portion having an upstream end, a downstream end, a longitudinal length therebetween, and a diameter transverse to the longitudinal axis;
a valve member, coupled to the tubular portion, disposed within the lumen, and arranged to provide unidirectional upstream-to-downstream flow of blood through the lumen;
an upstream support portion, coupled to the tubular portion; and
an outer frame, coupled to the tubular portion, and including a tissue-engaging flange,
and:
the implant has a first state and a second state,
in both the first state and the second state, (i) the upstream support portion extends radially outward from the tubular portion, and (ii) the tissue-engaging flange extends radially outward from the tubular portion, and
the tubular portion, the upstream support portion, and the outer frame are arranged such that transitioning of the implant from the first state toward the second state:
increases the diameter of the tubular portion by a diameter-increase amount,
decreases the length of the tubular portion by a length-decrease amount, and
moves the flange a longitudinal distance toward or toward-and-beyond the upstream support portion, the distance being greater than the length-decrease amount.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the tubular portion, the upstream support portion, and the outer frame are arranged such that the longitudinal distance is more than 20 percent greater than the length-decrease amount.

In an application, the tubular portion, the upstream support portion, and the outer frame are arranged such that the longitudinal distance is more than 30 percent greater than the length-decrease amount.

In an application, the tubular portion, the upstream support portion, and the outer frame are arranged such that the longitudinal distance is more than 40 percent greater than the length-decrease amount.

There is further provided, in accordance with an application of the present invention, apparatus for use with a native valve that is disposed between an atrium and a ventricle of a heart of a subject, the apparatus including:
  a valve frame, including a tubular portion that circumscribes a longitudinal axis of the valve frame so as to define a lumen along the axis;
  a plurality of prosthetic leaflets, coupled to the frame, disposed within the lumen, and arranged to provide unidirectional flow of blood from an upstream end of the lumen to a downstream end of the lumen;
  an outer frame, including:
    a ring defined by a pattern of alternating peaks and troughs:
      the peaks being longitudinally closer than the troughs to the upstream end,
      the peaks being fixed to respective sites of the tubular portion at respective coupling points disposed circumferentially around the longitudinal axis, and
      the pattern of the ring having an amplitude longitudinally between the peaks and the troughs; and
    a plurality of legs, each of the legs coupled to the ring at a respective trough,
  and:
    the tubular portion has (i) a compressed state in which the tubular portion has a compressed diameter, and (ii) an expanded state in which the tubular portion has an expanded diameter that is greater than the compressed diameter, and
    the fixation of the peaks to the respective sites of the tubular portion is such that compression of the tubular portion from the expanded state toward the compressed state such that the respective sites of the tubular portion pull the peaks radially inward via radially-inward tension on the coupling points: (i) reduces a circumferential distance between each of the coupling points and its adjacent coupling points, and (ii) increases the amplitude of the pattern of the ring.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the expanded state of the tubular portion is a constrained expanded state, and the fixation of the peaks to the respective sites of the tubular portion is such that, in a relaxed expanded state of the apparatus, the outer frame constrains the tubular portion in the constrained expanded state.

In an application, the outer frame is coupled to the valve frame only via the fixation of the peaks to the respective sites of the tubular portion at the respective coupling points.

There is further provided, in accordance with an application of the present invention, apparatus for use with a native valve that is disposed between an atrium and a ventricle of a heart of a subject, the apparatus including:
  a valve frame, including a tubular portion that circumscribes a longitudinal axis of the valve frame so as to define a lumen along the axis, the valve frame defining a plurality of valve-frame coupling elements disposed circumferentially around the longitudinal axis;
  a plurality of prosthetic leaflets, coupled to the frame, disposed within the lumen, and arranged to provide unidirectional flow of blood from an upstream end of the lumen to a downstream end of the lumen;
  an outer frame:
    including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs,
    including a plurality of legs, each of the legs coupled to the ring at a respective trough, and
    shaped to define a plurality of outer-frame coupling elements, each of the outer-frame coupling elements (i) coupled to the ring at a respective peak, and (ii) fixed with respect to a respective valve-frame coupling element,
  and:
    the tubular portion has (i) a compressed state in which the tubular portion has a compressed diameter, and (ii) an expanded state in which the tubular portion has an expanded diameter that is greater than the compressed diameter, and
    the fixation of the outer-frame coupling elements with respect to the valve-frame coupling elements is such that compression of the tubular portion from the expanded state toward the compressed state (i) pulls the outer-frame coupling elements radially inward via radially-inward pulling of the valve-frame coupling elements on the outer-frame coupling elements, (ii) reduces a circumferential distance between each of the outer-frame coupling elements and its adjacent outer-frame coupling elements, and (iii) increases the amplitude of the pattern of the ring, without increasing a radial gap between the valve frame and the ring by more than 1.5 mm.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the outer frame is coupled to the valve frame only via the fixation of the outer-frame coupling elements to the respective valve-frame coupling elements.

There is further provided, in accordance with an application of the present invention, apparatus for use with a native valve that is disposed between an atrium and a ventricle of a heart of a subject, the apparatus including:
  a valve frame, including a tubular portion that circumscribes a longitudinal axis of the valve frame so as to define a lumen along the axis;
  a plurality of prosthetic leaflets, coupled to the frame, disposed within the lumen, and arranged to provide unidirectional flow of blood from an upstream end of the lumen to a downstream end of the lumen;
  an outer frame, including:
    a ring defined by a pattern of alternating peaks and troughs:
      the peaks being longitudinally closer than the troughs to the upstream end, the peaks being fixed to respective sites of the tubular portion at respective coupling points disposed circumferentially around the longitudinal axis, and the pattern of the ring having an amplitude longitudinally between the peaks and the troughs; and a plurality of legs, each of the legs coupled to the ring at a respective trough, and:

the tubular portion has (i) a compressed state in which the tubular portion has a compressed diameter, and (ii) an expanded state in which the tubular portion has an expanded diameter that is greater than the compressed diameter, and the fixation of the peaks to the respective sites of the tubular portion is such that compression of the tubular portion from the expanded state toward the compressed state (i) pulls the peaks radially inward via radially-inward pulling of the respective sites of the tubular portion on the peaks, (ii) reduces a circumferential distance between each of the coupling points and its adjacent coupling points, and (iii) increases the amplitude of the pattern of the ring, without increasing a radial gap between the valve frame and the ring by more than 1.5 mm.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the outer frame is coupled to the valve frame only via the fixation of the peaks to the respective sites of the tubular portion at the respective coupling points.

There is further provided, in accordance with an application of the present invention, apparatus for use with a native valve disposed between an atrium and a ventricle of a heart of a subject, the apparatus including:

a valve frame, including a tubular portion that circumscribes a longitudinal axis of the valve frame so as to define a lumen along the axis, the tubular portion having an upstream end, a downstream end, and defining a plurality of valve-frame coupling elements disposed circumferentially around the longitudinal axis between the upstream end and the downstream end but not at the upstream end nor at the downstream end;

a plurality of prosthetic leaflets, disposed within the lumen, and arranged to provide unidirectional flow of blood through the lumen;

an outer frame:

including a ring defined by a pattern of alternating peaks and troughs, the peaks being longitudinally closer to the upstream end than to the downstream end, and the troughs being longitudinally closer to the downstream end than to the upstream end, including a plurality of legs, each of the legs coupled to the ring at a respective trough, and shaped to define a plurality of outer-frame coupling elements, each of the outer-frame coupling elements (i) coupled to the ring at a respective peak, and (ii) fixed with respect to a respective valve-frame coupling element at a respective coupling point, and:

the tubular portion has (i) a compressed state in which the tubular portion has a compressed diameter, and (ii) an expanded state in which the tubular portion has an expanded diameter that is greater than the compressed diameter, and expansion of the tubular portion from the compressed state toward the expanded state (i) increases a circumferential distance between each of the outer-frame coupling elements and its adjacent outer-frame coupling elements, and (ii) moves the plurality of legs in a longitudinally upstream direction with respect to the tubular portion.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the outer frame is coupled to the valve frame only via the fixation of the outer-frame coupling elements to the respective valve-frame coupling elements.

There is further provided, in accordance with an application of the present invention, apparatus for use with a native valve disposed between an atrium and a ventricle of a heart of a subject, the apparatus including:

a valve frame, including a tubular portion that circumscribes a longitudinal axis of the valve frame so as to define a lumen along the axis, the tubular portion having an upstream end and a downstream end;

a plurality of prosthetic leaflets, disposed within the lumen, and arranged to provide unidirectional flow of blood through the lumen;

an outer frame, including:

a ring defined by a pattern of alternating peaks and troughs:

the peaks being longitudinally closer than the troughs to the upstream end, the peaks being fixed to respective sites of the tubular portion at respective coupling points disposed circumferentially around the longitudinal axis between the upstream end and the downstream end but not at the upstream end nor the downstream end; and a plurality of legs, each of the legs coupled to the ring at a respective trough, and:

the tubular portion has (i) a compressed state in which the tubular portion has a compressed diameter, and (ii) an expanded state in which the tubular portion has an expanded diameter that is greater than the compressed diameter, and expansion of the tubular portion from the compressed state toward the expanded state (i) increases a circumferential distance between each of the coupling points and its adjacent coupling points, and (ii) moves the plurality of legs in a longitudinally upstream direction with respect to the tubular portion.

In an application, the valve frame is cut from a first tube of nitinol that has a first-tube wall thickness, and the outer frame is cut from a second tube of nitinol that has a second-tube wall thickness that is greater than the first-tube wall thickness.

In an application, the outer frame is coupled to the valve frame only via the fixation of the peaks to the respective sites of the tubular portion at the respective coupling points.

There is further provided, in accordance with an application of the present invention, apparatus for use with a native valve of a heart of a subject, the apparatus including:

a frame assembly, having an upstream end and a downstream end, and a central longitudinal axis therebetween, and including:

a valve frame, including:

a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly:

has a compressed state, for percutaneous delivery to the heart, in which the tubular portion has a compressed diameter, is biased to assume an expanded state in which the tubular portion has an expanded diameter that is greater than the compressed diameter, and is configured such that increasing the diameter of the tubular portion toward the expanded diameter causes longitudinal movement:

of the upstream support portion toward the coupling point, and of the tissue-engaging flange away from the coupling point.

In an application, the valve frame is cut from a first tube of nitinol that has a first-tube wall thickness, and the at least one leg is cut from a second tube of nitinol that has a second-tube wall thickness that is greater than the first-tube wall thickness.

In an application:

the apparatus includes an implant that includes the frame assembly and the valve member, and the apparatus further includes a tool:

including a delivery capsule dimensioned (i) to house and retain the implant in the compressed state, and (ii) to be advanced percutaneously to the heart of the subject while the implant is housed and in the compressed state, and operable from outside the subject to facilitate an increase of the diameter of the tubular portion from the compressed diameter toward the expanded diameter such that the increase of the diameter actuates longitudinal movement:

of the upstream support portion toward the coupling point, and of the tissue-engaging flange away from the coupling point.

In an application, the frame assembly is configured such that increasing the diameter of the tubular portion by expanding the frame assembly toward the expanded state causes longitudinal movement of the upstream end of the tubular portion toward the coupling point.

In an application, the coupling point is disposed closer to the downstream end of the frame assembly than are either the tissue-engaging flange or the upstream support portion.

In an application, in the expanded state of the frame assembly, the leg extends away from the central longitudinal axis.

In an application:

the expanded state of the frame assembly is a fully-expanded state of the frame assembly, the leg is expandable into an expanded state of the leg, independently of increasing the diameter of the tubular portion, and in the expanded state of the leg, the leg extends away from the central longitudinal axis.

In an application:

in the expanded state of the frame assembly, the leg extends away from the central longitudinal axis, and in the compressed state of the frame assembly, the leg is generally parallel with the central longitudinal axis.

In an application, the frame assembly is configured such that the longitudinal movement of the tissue-engaging flange away from the coupling point is a translational movement of the tissue-engaging flange that does not include rotation of the tissue-engaging flange.

In an application, the frame assembly is configured such that increasing the diameter of the tubular portion by expanding the frame assembly toward the expanded state causes 1-20 mm of longitudinal movement of the tissue-engaging flange away from the coupling point.

In an application, the frame assembly is configured such that increasing the diameter of the tubular portion by expanding the frame assembly toward the expanded state causes 1-20 mm of longitudinal movement of the upstream support portion toward the coupling point.

In an application, the frame assembly is configured such that increasing the diameter of the tubular portion by expanding the frame assembly toward the expanded state reduces a distance between the upstream support portion and the tissue-engaging flange by 5-30 mm.

In an application, the frame assembly is configured such that increasing the diameter of the tubular portion by expanding the frame assembly toward the expanded state moves the tissue-engaging flange longitudinally past the upstream support portion.

In an application:

the tubular portion is defined by a plurality of cells of the valve frame, and increasing the diameter of the tubular portion by expanding the frame assembly toward the expanded state:

includes (i) increasing a width, orthogonal to the longitudinal axis of the frame assembly, of each cell, and (ii) reducing a height, parallel with the longitudinal axis of the frame assembly, of each cell, and causes longitudinal movement of the upstream support portion toward the coupling point by reducing a height, parallel with the longitudinal axis of the frame assembly, of the tubular portion, by reducing the height of each cell.

In an application, the leg is disposed on an outside of the tubular portion.

In an application:

the at least one leg includes a plurality of legs, the coupling point includes a plurality of coupling points, and the frame assembly includes a leg frame that circumscribes the tubular portion, includes the plurality of legs, and is coupled to the valve frame at the plurality of coupling points, such that the plurality of legs is distributed circumferentially around the tubular portion.

In an application, the plurality of coupling points is disposed circumferentially around the frame assembly on a transverse plane that is orthogonal to the longitudinal axis of the frame assembly.

In an application, the plurality of legs is coupled to the valve frame via a plurality of struts, each strut:

having a first end that is coupled to a leg of the plurality of legs, and a second end that is coupled to a coupling point of the plurality of coupling points, in the compressed state of the frame assembly, being disposed at a first angle in which the first end is disposed closer to the downstream end of the frame assembly than is the second end, and being deflectable with respect to the coupling point of the plurality of coupling points, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an application, the leg frame is structured such that each leg of the plurality of legs is coupled to two struts of the plurality of struts, and two struts of the plurality of struts are coupled to each coupling point of the plurality of coupling points.

In an application, the leg is coupled to the valve frame via a strut, the strut:

having a first end that is coupled to the leg, and a second end that is coupled to the coupling point, in the compressed state of the frame assembly, being disposed at a first angle in which the first end is disposed closer to the downstream end of the frame assembly than is the second end, and being deflectable with respect to the coupling point, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an application, the at least one leg includes at least a first leg and a second leg.

In an application, the first leg and the second leg are both coupled to the valve frame at the coupling point.

In an application, the first leg is coupled to the coupling point via a respective first strut, and the second leg is coupled to the coupling point via a respective second strut.

In an application, the first and second legs, the first and second struts, and the coupling point are arranged such that, in the expanded state of the frame assembly:

the coupling point is disposed, circumferentially with respect to the tubular portion, between the first strut and the second strut, the first strut is disposed, circumferentially with respect to the tubular portion, between the coupling point and the first leg, and the second strut is disposed, circumferentially with respect to the tubular portion, between the coupling point and the second leg.

In an application, the coupling point includes at least a first coupling point and a second coupling point.

In an application, the leg is coupled to the valve frame at the first coupling point and at the second coupling point.

In an application, the leg is coupled to the first coupling point via a respective first strut, and to the second coupling point via a respective second strut.

In an application, the first and second legs, the first and second struts, and the coupling point are arranged such that, in the expanded state of the frame assembly:

the leg is disposed, circumferentially with respect to the tubular portion, between the first strut and the second strut, the first strut is disposed, circumferentially with respect to the tubular portion, between the leg and the first coupling point, and the second strut is disposed, circumferentially with respect to the tubular portion, between the leg and the second coupling point.

In an application, in the expanded state of the frame assembly, the upstream support portion extends radially outward from the tubular portion.

In an application:

the expanded state of the frame assembly is a fully-expanded state of the frame assembly, the upstream support portion is expandable into an expanded state of the upstream support portion, independently of increasing the diameter of the tubular portion, and in the expanded state of the upstream support portion, the upstream support portion extends radially outward from the tubular portion.

In an application, in the compressed state of the frame assembly, the upstream support portion is generally tubular, collinear with the tubular portion, and disposed around the central longitudinal axis.

In an application, in the expanded state of the frame assembly, an inner region of the upstream support portion extends radially outward from the tubular portion at a first angle with respect to the tubular portion, and an outer region of the upstream support portion extends, from the inner region of the upstream support portion, further radially outward from the tubular portion at a second angle with respect to the tubular portion, the second angle being smaller than the first angle.

There is further provided, in accordance with an application of the present invention, apparatus for use with a native valve of a heart of a subject, the apparatus including:

a frame assembly, having an upstream end and a downstream end, and a central longitudinal axis therebetween, and including:

a valve frame, including:

a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly:

has a compressed state, for percutaneous delivery to the heart, in which the tubular portion has a compressed diameter, is biased to assume an expanded state in which the tubular portion has an expanded diameter that is greater than the compressed diameter, and is configured such that reducing the diameter of the tubular portion toward the compressed diameter causes longitudinal movement:

of the upstream support portion away from the coupling point, and of the tissue-engaging flange toward the coupling point.

In an application, the valve frame is cut from a first tube of nitinol that has a first-tube wall thickness, and the at least one leg is cut from a second tube of nitinol that has a second-tube wall thickness that is greater than the first-tube wall thickness.

There is further provided, in accordance with an application of the present invention, apparatus for use with a native valve of a heart of a subject, the apparatus including:

a frame assembly, having an upstream end and a downstream end, and a central longitudinal axis therebetween, including:

a valve frame, including:

a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly:

has a compressed state, for percutaneous delivery to the heart, is intracorporeally expandable into an expanded state in which a diameter of the tubular portion is greater than in the compressed state, and is configured such that increasing the diameter of the tubular portion by expanding the frame assembly toward the expanded state causes longitudinal movement of the tissue-engaging flange away from the coupling point.

In an application, the valve frame is cut from a first tube of nitinol that has a first-tube wall thickness, and the at least one leg is cut from a second tube of nitinol that has a second-tube wall thickness that is greater than the first-tube wall thickness.

There is further provided, in accordance with an application of the present invention, apparatus for use with a native valve of a heart of a subject, the apparatus including:

a frame assembly, having an upstream end and a downstream end, and a central longitudinal axis therebetween, and including:

an inner frame including an inner-frame tubular portion that circumscribes the central longitudinal axis, has an upstream end and a downstream end, and defines a channel therebetween, the inner frame defining a plurality of inner-frame couplings disposed circumferentially at a longitudinal location of the inner frame, an outer frame including an outer-frame tubular portion that coaxially circumscribes at least a portion of the inner-frame tubular portion, the outer frame defining a plurality of outer-frame couplings disposed circumferentially at a longitudinal location of the outer frame, and a plurality of connectors, each connector connecting a respective inner-frame coupling to a respective outer-frame coupling;

a liner, disposed over at least part of the inner-frame tubular portion; and a plurality of prosthetic leaflets, coupled to the inner-frame tubular portion and disposed within the channel, and:

the frame assembly: (i) is compressible by a radially-compressive force into a compressed state in which the inner frame is in a compressed state thereof and the outer frame is in a compressed state thereof, (ii) is configured, upon removal of the radially-compressive force, to automatically expand into an expanded state thereof in which the inner frame is in an expanded state thereof and the outer frame is in an expanded state thereof, in the expanded state of the frame assembly, the prosthetic leaflets are configured to facilitate one-way fluid flow, in a downstream direction, through the channel, and the connection of the inner-frame couplings to the respective outer-frame couplings is such that expansion of the frame assembly from the compressed state to the expanded state causes the inner-frame tubular portion to slide longitudinally in a downstream direction with respect to the outer-frame tubular portion.

In an application, the inner frame is cut from a first tube of nitinol that has a first-tube wall thickness, and the outer frame is cut from a second tube of nitinol that has a second-tube wall thickness that is greater than the first-tube wall thickness.

There is further provided, in accordance with an application of the present invention, apparatus for use with a native valve disposed between an atrium and a ventricle of a heart of a subject, the apparatus including:

a tubular portion, having an upstream portion that includes an upstream end, and a downstream portion that includes a downstream end, and shaped to define a lumen between the upstream portion and the downstream portion;

a plurality of prosthetic leaflets, disposed within the lumen, and arranged to provide unidirectional flow of blood from the upstream portion to the downstream portion;

an annular upstream support portion:

having an inner portion that extends radially outward from the upstream portion, and including one or more fabric pockets disposed circumferentially around the inner portion, each pocket of the one or more pockets having an opening that faces a downstream direction.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the inner portion of the upstream support portion, the covering is closely-fitted between the radially-inner parts of the arms, and at the outer portion of the upstream support portion, the pockets are formed by the covering being loosely-fitted between the radially-outer parts of the arms.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, the radially-outer part being more flexible than the radially-inner part.

In an application:

the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the outer portion of the upstream support portion, the pockets are formed by each arm curving to form a hook shape.

In an application, each pocket is shaped and arranged to billow in response to perivalvular flow of blood in an upstream direction.

In an application, the apparatus is configured to be transluminally delivered to the heart, and implanted at the native valve by expansion of the apparatus, such that the upstream support portion is disposed in the atrium and the tubular portion extends from the upstream support portion into the ventricle, and each pocket is shaped and arranged such that perivalvular flow of blood in an upstream direction presses the pocket against tissue of the atrium.

There is further provided, in accordance with an application of the present invention, apparatus including:
- a plurality of prosthetic valve leaflets; and
- a frame assembly, including:
  - a tubular portion defined by a repeating pattern of cells, the tubular portion extending circumferentially around a longitudinal axis so as to define a longitudinal lumen, the prosthetic valve leaflets coupled to the inner frame and disposed within the lumen;
  - an outer frame, including a plurality of legs, distributed circumferentially around the tubular portion, each leg having a tissue-engaging flange;
  - an upstream support portion that includes a plurality of arms that extend radially outward from the tubular portion; and
  - a plurality of appendages, each having a first end that defines a coupling element via which the tubular portion is coupled to the outer frame, and a second end;
- and the frame assembly defines a plurality of hubs, distributed circumferentially around the longitudinal axis on a plane that is transverse to the longitudinal axis, each hub defined by convergence and connection of, (i) two adjacent cells of the tubular portion, (ii) an arm of the plurality of arms, and (iii) an appendage of the plurality of appendages.

In an application, the tubular portion is cut from a first tube of nitinol that has a first-tube wall thickness, and the outer frame is cut from a second tube of nitinol that has a second-tube wall thickness that is greater than the first-tube wall thickness.

In an application, each hub has six radiating spokes, two of the six spokes being part of a first cell of the two adjacent cells, two of the six spokes being part of a second cell of the two adjacent cells, one of the six spokes being the arm, and one of the six spokes being the second end of the appendage.

In an application, the appendages are in-plane with the tubular portion.

In an application, the appendages are in-plane with the outer frame.

The present invention will be more fully understood from the following detailed description of applications thereof, taken together with the drawings, in which:

BRIEF DESCRIPTION OF THE DRAWINGS

FIGS. 1A-B and 2A-E are schematic illustrations of an implant for use with a native valve of a heart of a subject, in accordance with some applications of the invention;

FIGS. 3A-C are schematic illustrations that show structural changes in a frame assembly during transitioning of the assembly between its compressed and expanded states, in accordance with some applications of the invention;

FIGS. 4A-F are schematic illustrations of implantation of the implant at the native valve, in accordance with some applications of the invention;

FIGS. 7A-B and 8A-B are schematic illustrations of frame assemblies of respective implants, in accordance with some applications of the invention;

FIGS. 9A-C are schematic illustrations of an implant comprising a frame assembly, in accordance with some applications of the invention;

FIG. 10 is a schematic illustration of a frame assembly of an implant, in accordance with some applications of the invention;

FIGS. 12A-B and 13A-F are schematic illustrations of a connector for connecting prosthetic leaflets to a frame of a prosthetic valve implant, in accordance with some applications of the invention.

DETAILED DESCRIPTION OF EMBODIMENTS

Figure 3B:
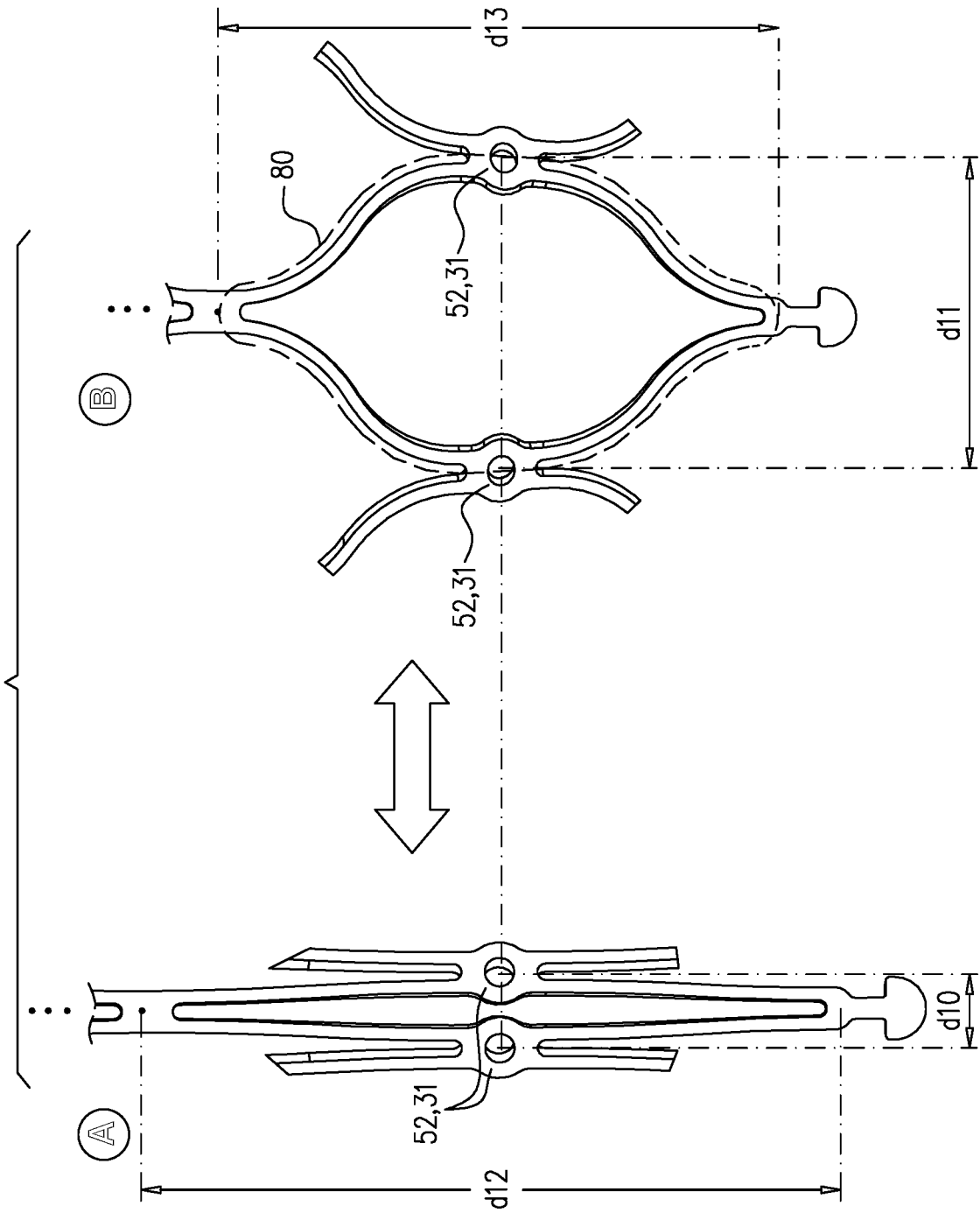

Reference is made to FIGS. 1A-B and 2A-E, which are schematic illustrations of an implant 20 for use with a native valve of a heart of a subject, in accordance with some applications of the invention. Implant 20 comprises a frame assembly 22 that has an upstream end 24, a downstream end 26, and a central longitudinal axis ax1 therebetween. Frame assembly 22 comprises a valve frame 30 that comprises a tubular portion 32 that has an upstream end 34 and a downstream end 36, and is shaped to define a lumen 38 through the tubular portion from the upstream end to the downstream end. Tubular portion 32 circumscribes axis ax1, and thereby defines lumen 38 along the axis. Valve frame 30 further comprises an upstream support portion 40, extending from upstream end 34 of tubular portion 32. Frame assembly 22 further comprises at least one leg 50, coupled to valve frame 30 at (e.g., via) a coupling point 52, and having a tissue-engaging flange 54.

Typically, and as described hereinbelow, leg 50 is part of an outer frame (or "leg frame") 60, and frames 30 and 60 define respective coupling elements 31 and 61, which are fixed with respect to each other at coupling points 52. Typically, frames 30 and 60 are coupled to each other only at coupling points 52 (e.g., only via the fixation of coupling elements 31 and 61 with respect to each other).

Implant 20 further comprises a valve member 58 (e.g., one or more prosthetic leaflets) disposed within lumen 38, and configured to facilitate one-way liquid flow through the lumen from upstream end 34 to downstream end 36 (e.g., thereby defining the orientation of the upstream and downstream ends of tubular portion 32). FIG. 1A shows implant 20 in a fully-expanded state, in which frame assembly 22 is in a fully-expanded state. FIG. 1B shows an exploded view of frame assembly 22 in its fully-expanded state. FIGS. 2A-E show respective states of implant 20, which will be discussed in more detail hereinbelow with respect to the implantation of the implant and the anatomy in which the implant is implanted. FIG. 2A shows implant 20 in a compressed state (in which frame assembly 22 is in a compressed state), for percutaneous delivery of the implant to the heart of the subject. Typically, in the compressed state, leg 50 (including flange 54 thereof) is in a constrained-flange state in which the flange is generally parallel with axis ax1. Further typically, in the compressed state, upstream support portion 40 is generally tubular, collinear with tubular portion 32 (e.g., extending collinearly from the tubular portion), and disposed around axis ax1.

FIG. 2B shows a state of implant 20 in which tissue-engaging flange 54 of each leg 50 extends radially away from axis ax1 (e.g., radially away from tubular portion 32). FIG. 2C shows a state of implant 20 in which upstream-support portion 40 extends radially away from axis ax1 (and thereby radially away from tubular portion 32). FIG. 2D shows a state of implant 20 in which both flange 54 and portion 40 extend away from axis ax1. In the fully-expanded state (FIGS. 1A-B) both upstream support portion 40 and flange 54 extend radially away from axis ax1. Typically, frame assembly 22 is biased (e.g., shape-set) to assume its fully-expanded state, which is shown in FIG. 2E. Transitioning of implant 20 between the respective states is typically controlled by delivery apparatus, such as by constraining the implant in a compressed state within a delivery tube and/or against a control rod, and selectively releasing portions of the implant to allow them to expand.

In the compressed state of frame assembly 22, tubular portion 32 has a diameter d1, and in the expanded state, the tubular portion has a diameter d2 that is greater that diameter d1. For some applications, diameter d1 is 4-15 mm, (e.g., 5-11 mm) and diameter d2 is 20-50 mm, (e.g., 23-33 mm). For some applications, and as shown, in its expanded state tubular portion 32 bulges slightly in its middle (e.g., is slightly barrel-shaped). For such applications, values of diameter d2 are the average diameter along the tubular portion. Similarly, values for the cross-sectional area of the tubular portion are the average cross-sectional area along the tubular portion. This also applies to other implants described herein, mutatis mutandis.

Frame assembly 22 is configured such that increasing the diameter of tubular portion 32 (e.g., from d1 to d2) causes longitudinal movement of flange 54 away from coupling point 52. In the same way, reducing the diameter of tubular portion 32 (e.g., from d2 to d1) causes longitudinal movement of flange 54 toward coupling point 52. It is to be noted that the term "longitudinal movement" (including the specification and the claims) means movement parallel with central longitudinal axis ax1. Therefore, longitudinal movement of flange 54 away from coupling point 52 means increasing a distance, measured parallel with longitudinal axis ax1, between flange 54 and coupling point 52. An example of such a configuration is described in more detail with respect to FIG. 3A.

Similarly reference to an element being "upstream of" (or "above") or "downstream of" (or "below") another element refers to its relative position along the central longitudinal axis of the implant ("upstream" and "downstream" being defined by the direction in which the implant facilitates blood flow).

Thus, expansion of tubular portion 32 from its compressed state toward its expanded state (i) increases a circumferential distance between each of coupling points 52 and its adjacent coupling points (e.g., between each of outer-frame coupling elements 61 and its adjacent outer-frame coupling elements) (e.g., from d8 to d9), and (ii) moves legs 50 in a longitudinally upstream direction with respect to the tubular portion.

Typically, frame assembly 22 is configured such that increasing the diameter of tubular portion 32 also causes longitudinal movement of upstream support portion 40 toward coupling point 52, e.g., as described in more detail with respect to FIGS. 3B-C. Typically, frame assembly 22 is configured such that increasing the diameter of tubular portion 32 also causes longitudinal movement of upstream end 34 of tubular portion 32 toward coupling point 52. In the same way, reducing the diameter of tubular portion 32 causes longitudinal movement of upstream end 34 away from coupling point 52.

For some applications, upstream support portion 40 comprises a plurality of arms 46 that each extends radially outward from tubular portion 32 (e.g., from upstream end 34 of the tubular portion). Arms 46 are typically flexible. For some such applications, arms 46 are coupled to tubular portion 32 such that each arm may deflect independently of adjacent arms during implantation (e.g., due to anatomical topography).

For some applications, upstream support portion 40 comprises a plurality of barbs 48 that extend out of a downstream surface of the upstream support portion. For example, each arm 46 may comprise one or more of barbs 48. Barbs 48 press into tissue upstream of the native valve (e.g., into the valve annulus), thereby inhibiting downstream movement of implant 20 (in addition to inhibition of downstream movement provided by the geometry of upstream support portion 40).

One or more surfaces of frame assembly 22 are covered with a covering 23, which typically comprises a flexible sheet, such as a fabric, e.g., comprising polyester. Typically, covering 23 covers at least part of tubular portion 32, typically lining an inner surface of the tubular portion, and thereby defining lumen 38.

Further typically, upstream support portion 40 is covered with covering 23, e.g., extending between arms 46 to form an annular shape. It is hypothesized that this reduces a likelihood of paravalvular leakage. For such applications, excess covering 23 may be provided between arms 46 of upstream support portion 40, so as to facilitate their independent movement. Although FIG. 1A shows covering 23 covering an upstream side of upstream support portion 40, the covering typically additionally (or alternatively) covers the downstream side of the upstream support portion. For example, covering 23 may extend over the tips of arms 46 and down the outside of the arms, or a separate piece of covering may be provided on the downstream side of the upstream support portion.

Alternatively, each arm 46 may be individually covered in a sleeve of covering 23, thereby facilitating independent movement of the arms.

For some applications, at least part of legs 50 (e.g., flanges thereof) is covered with covering 23.

Typically, frame assembly 22 comprises a plurality of legs 50 (e.g., two or more legs, e.g., 2-16 legs, such as 4-12 legs, such as 6-12 legs), arranged circumferentially around valve frame 30 (e.g., around the outside of tubular portion 32). Typically, frame assembly 22 comprises a plurality of coupling points 52 at which the legs are coupled to valve frame 30.

As described in more detail hereinbelow (e.g., with reference to FIG. 3A), each leg 50 is typically coupled to a coupling point 52 via a strut 70. For some applications, each leg 50 is coupled to a plurality of (e.g., two) coupling points 52 via a respective plurality of (e.g., two) struts 70. For some such applications, frame assembly 22 is arranged such that, in the expanded state of the frame assembly, leg 50 is disposed, circumferentially with respect to tubular portion 32, between two struts, and each of the two struts are disposed, circumferentially with respect to the tubular portion, between the leg and a respective coupling point 52.

For some applications, a plurality of (e.g., two) legs are coupled to each coupling point 52 via a respective plurality of (e.g., two) struts 70. For some such applications, frame assembly 22 is arranged such that, in the expanded state of the frame assembly, coupling point 52 is disposed, circumferentially with respect to tubular portion 32, between two struts 70, and each of the two struts are disposed, circumferentially with respect to the tubular portion, between the coupling point and a respective leg 50.

For some applications, frame assembly 22 comprises an outer frame (e.g., a leg frame) 60 that circumscribes tubular portion 32, comprises (or defines) the plurality of legs 50 and the plurality of struts 70, and is coupled to valve frame 30 at the plurality of coupling points 52, such that the plurality of legs are distributed circumferentially around the tubular portion. For such applications, outer frame 60 comprises a ring 66 that is defined by a pattern of alternating peaks 64 and troughs 62, and that typically circumscribes tubular portion 32. For example, the ring may comprise struts 70, extending between the peaks and troughs. Peaks 64 are longitudinally closer to upstream end 34 of tubular portion 32 than to downstream end 36, and troughs 62 are longitudinally closer to the downstream end than to the upstream end. (It is to be noted that throughout this patent application, including the specification and the claims, the term "longitudinally" means with respect to longitudinal axis ax1. For example, "longitudinally closer" means closer along axis ax1 (whether positioned on axis ax1 or lateral to axis ax1), and "longitudinal movement" means a change in position along axis ax1 (which may be in additional to movement toward or away from axis ax1).) Therefore, peaks 64 are closer than troughs 62 to upstream end 34, and troughs 62 are closer than peaks 64 to downstream end 36. For applications in which frame 60 comprises ring 66, each leg 50 is coupled to the ring (or defined by frame 60) at a respective trough 62.

In the embodiment shown, the peaks and troughs are defined by ring 66 having a generally zig-zag shape. However, the scope of the invention includes ring 66 having another shape that defines peaks and troughs, such as a serpentine or sinusoid shape.

For applications in which frame assembly 22 has a plurality of coupling points 52, the coupling points (and therefore coupling elements 31 and 61) are disposed circumferentially around the frame assembly (e.g., around axis ax1), typically on a transverse plane that is orthogonal to axis ax1. This transverse plane is illustrated by the position of section A-A in FIG. 2B. Alternatively, coupling points 52 may be disposed at different longitudinal heights of frame assembly 22, e.g., such that different flanges 54 are positioned and/or moved differently to others. Typically, coupling points 52 (and therefore coupling elements 31 and 61) are disposed longitudinally between upstream end 24 and downstream end 26 of frame assembly 22, but not at either of these ends. Further typically, coupling points 52 are disposed longitudinally between upstream end 34 and downstream end 36 of tubular portion 32, but not at either of these ends. For example, the coupling points may be more than 3 mm (e.g., 4-10 mm) both from end 34 and from end 36. It is hypothesized that this advantageously positions the coupling points at a part of tubular portion 32 that is more rigid than end 34 or end 36.

It is to be noted that leg 50 is typically expandable into its expanded state (e.g., a released-flange state) such that flange 54 extends away from axis ax1, independently of increasing the diameter of tubular portion 32 (e.g., as shown in FIGS. 2B & 2D). Similarly, upstream support portion 40 is typically expandable into its expanded state (e.g., a released-arm state) such that it (e.g., arms 46 thereof) extends away from axis ax1, independently of increasing the diameter of tubular portion 32 (e.g., as shown in FIGS. 2C & 2D). The state shown in FIG. 2D may be considered to be an intermediate state. Therefore, implant 20 is typically configured such that legs 50 (e.g., flanges 54 thereof) and upstream support portion 40 are expandable such that they both extend away from axis ax1, while retaining a distance d3 therebetween. This distance is subsequently reducible to a distance d4 by expanding tubular portion 32 (e.g., shown in FIG. 2E).

For some applications, while tubular portion 32 remains in its compressed state, flange 54 can extend away from axis ax1 over 40 percent (e.g., 40-80 percent, such as 40-70 percent) of the distance that it extends from the axis subsequent to the expansion of the tubular portion. For example, for applications in which implant 20 comprises a flange on opposing sides of the implant, a span d15 of the flanges while tubular portion 32 is in its compressed state may be at least 40 percent (e.g., 40-80 percent, such as 40-70 percent) as great as a span d16 of the flanges subsequent to the expansion of the tubular portion. For some applications, span d15 is greater than 15 mm and/or less than 50 mm (e.g., 20-30 mm). For some applications, span d16 is greater than 30 mm and/or less than 60 mm (e.g., 40-50 mm). It is to be noted that flange 54 is effectively fully expanded, with respect to other portions of leg 50 and/or with respect to tubular portion 32, before and after the expansion of the tubular portion.

Similarly, for some applications, while tubular portion 32 remains in its compressed state, upstream support portion 40 (e.g., arms 46) can extend away from axis ax1 over 30 percent (e.g., 30-70 percent) of the distance that it extends from the axis subsequent to the expansion of the tubular portion. That is, for some applications, a span d17 of the upstream support portion while tubular portion 32 is in its compressed state may be at least 30 percent (e.g., 30-70 percent) as great as a span d18 of the upstream support portion subsequent to the expansion of the tubular portion. For some applications, span d17 is greater than 16 mm (e.g., greater than 20 mm) and/or less than 50 mm (e.g., 30-40 mm). For some applications, span d18 is greater than 40 mm and/or less than 65 mm (e.g., 45-56 mm, such as 45-50 mm). It is to be noted that upstream support portion 40 is effectively fully expanded, with respect to tubular portion 32, before and after the expansion of the tubular portion.

It is to be noted that when tubular portion 32 is expanded, flanges 54 typically translate radially outward from span d15 to span d16 (e.g., without deflecting). Typically, upstream support portion 40 behaves similarly (e.g., arms 46 translated radially outward from span d17 to span d18, e.g., without deflecting). That is, an orientation of each flange 54 and/or each arm 46 with respect to tubular portion 32 and/or axis ax1 is typically the same in the state shown in FIG. 2D as it is in the state shown in FIG. 2E. Similarly, for some applications an orientation of each flange 54 with respect to upstream support portion 40 (e.g., with respect to one or more arms 46 thereof) is the same before and after expansion of tubular portion 32.

For some applications, increasing the diameter of tubular portion 32 from d1 to d2 causes greater than 1 mm and/or less than 20 mm (e.g., 1-20 mm, such as 1-10 mm or 5-20 mm) of longitudinal movement of flange 54 away from coupling point 52. For some applications, increasing the diameter of tubular portion 32 from d1 to d2 causes greater than 1 mm and/or less than 20 mm (e.g., 1-20 mm, such as 1-10 mm or 5-20 mm) of longitudinal movement of upstream support portion 40 toward coupling point 52. For some applications, distance d3 is 7-30 mm. For some applications, distance d4 is 0-15 mm (e.g., 2-15 mm). For some applications, increasing the diameter of tubular portion 32 from d1 to d2 reduces the distance between the upstream support portion and flanges 54 by more than 5 mm and/or less than 30 mm, such as 5-30 mm (e.g., 10-30 mm, such as 10-20 mm or 20-30 mm). For some applications, the difference between d3 and d4 is generally equal to the difference between d1 and d2. For some applications, the difference between d3 and d4 is more than 1.2 and/or less than 3 times (e.g., 1.5-2.5 times, such as about 2 times) greater than the difference between d1 and d2.

For some applications, flanges 54 curve such that a tip of each flange is disposed at a shallower angle with respect to inner region 42 of upstream support portion 40, than are portions of leg 50 that are closer to downstream end 26 of frame assembly 22. For some such applications, a tip of each flange may be generally parallel with inner region 42. For some such applications, while tubular portion 32 is in its expanded state, a tip portion 55 of each flange 54 that extends from the tip of the flange at least 2 mm along the flange, is disposed within 2 mm of upstream support portion 40. Thus, for some applications, while tubular portion 32 is in its expanded state, for at least 5 percent (e.g., 5-8 percent, or at least 8 percent) of span 18 of upstream support portion 40, the upstream support portion is disposed within 2 mm of a flange 54.

For some applications, in the absence of any obstruction (such as tissue of the valve or covering 23) between flange 54 and upstream support portion 40, increasing the diameter of tubular portion 32 from d1 to d2 causes the flange and the upstream support portion to move past each other (e.g., the flange may move between arms 46 of the upstream support portion), such that the flange is closer to the upstream end of implant 20 than is the upstream support portion, e.g., as shown hereinbelow for frame assemblies 122 and 222, mutatis mutandis. (For applications in which upstream support portion 40 is covered by covering 23, flanges 54 typically don't pass the covering. For example, in the absence of any obstruction, flanges 54 may pass between arms 46, and press directly against covering 23.) It is hypothesized that for some applications this configuration applies greater force to the valve tissue being sandwiched, and thereby further facilitates anchoring of the implant. That is, for some applications, distance d3 is smaller than the sum of distance d5 and a distance d14 (described with reference to FIG. 3C). For some applications, increasing the diameter of tubular portion 32 from d1 to d2 advantageously causes flanges 54 and upstream support portion 40 to move greater than 3 mm and/or less than 25 mm (e.g., greater than 5 mm and/or less than 15 mm, e.g., 5-10 mm, such as about 7 mm) with respect to each other (e.g., toward each other and then past each other).

For some applications, in the expanded state of frame assembly 22, upstream support portion 40 has an inner region (e.g., an inner ring) 42 that extends radially outward at a first angle with respect to axis ax1 (and typically with respect to tubular portion 32), and an outer region (e.g., an outer ring) 44 that extends, from the inner region, further radially outward from the tubular portion at a second angle with respect to the tubular portion, the second angle being smaller than the first angle. For example, for some applications inner region 42 extends radially outward at an angle alpha_1 of 60-120 degrees (e.g., 70-110 degrees) with respect to axis ax1, and outer region 44 extends radially outward at an angle alpha_2 of 5-70 degrees (e.g., 10-60 degrees) with respect to axis ax1.

It is to be noted that angles alpha_1 and alpha_2 are measured between the respective region support portion 40, and the portion of axis ax1 that extends in an upstream direction from the level of frame assembly 22 at which the respective region begins to extend radially outward.

For some applications in which implant 20 is configured to be placed at an atrioventricular valve (e.g., a mitral valve or a tricuspid valve) of the subject, region 42 is configured to be placed against the upstream surface of the annulus of the atrioventricular valve, and region 44 is configured to be placed against the walls of the atrium upstream of the valve.

For some applications, outer region 44 is more flexible than inner region 42. For example, and as shown, each arm 46 may have a different structure in region 44 than in region 42. It is hypothesized that the relative rigidity of region 42 provides resistance against ventricular migration of implant 20, while the relative flexibility of region 44 facilitates conformation of upstream support portion 40 to the atrial anatomy.

For some applications, two or more of arms 46 are connected by a connector (not shown), reducing the flexibility, and/or the independence of movement of the connected arms relative to each other. For some applications, arms 46 are connected in particular sectors of upstream support portion 40, thereby making these sectors more rigid than sectors in which the arms are not connected. For example, a relatively rigid sector may be provided to be placed against the posterior portion of the mitral annulus, and a relatively flexible sector may be provided to be placed against the anterior side of the mitral annulus, so as to reduce forces applied by upstream support portion 40 on the aortic sinus.

For some applications, and as shown, coupling points 52 are disposed closer to downstream end 26 of frame assembly 22 than are flanges 54, or is upstream support portion 40.

As described in more detail with respect to FIGS. 4A-F, the movement of flange 54 away from coupling point 52 (and the typical movement of upstream support portion 40 toward the coupling point) facilitates the sandwiching of tissue of the native valve (e.g., leaflet and/or annulus tissue) between the flange and the upstream support portion, thereby securing implant 20 at the native valve.

Typically, in the compressed state of tubular portion 32, a downstream end of each leg 50 is longitudinally closer than valve-frame coupling elements 31 to downstream end 36, and flange 54 of each leg is disposed longitudinally closer than the valve-frame coupling elements to upstream end 34. Typically, this is also the case in the expanded state of tubular portion 32.

FIGS. 3A-C show structural changes in frame assembly 22 during transitioning of the assembly between its compressed and expanded states, in accordance with some applications of the invention. FIGS. 3A-C each show a portion of the frame assembly, the structural changes thereof being representative of the structural changes that occur in other portions of the frame assembly. FIG. 3A shows a leg 50 and struts 70 (e.g., a portion of outer frame 60), and illustrates the structural changes that occur around outer frame 60. FIG. 3B shows a portion of valve frame 30, and illustrates the structural changes that occur around the valve frame. FIG. 3C shows valve frame 30 as a whole. In each of FIGS. 3A-C, state (A) illustrates the structure while frame assembly 22 (and in particular tubular portion 32) is in its compressed state, and state (B) illustrates the structure while the frame assembly (and in particular tubular portion 32) is in its expanded state.

FIG. 3A shows structural changes in the coupling of legs 50 to coupling point 52 (e.g., structural changes of outer frame 60) during the transitioning of frame assembly 22 (and in particular tubular portion 32) between its compressed and expanded states. Each leg 50 is coupled to valve frame 30 via at least one strut 70, which connects the leg to coupling point 52. Typically, each leg 50 is coupled to valve frame 30 via a plurality of struts 70. A first end 72 of each strut 70 is coupled to leg 50, and a second end 74 of each strut is coupled to a coupling point 52. As described hereinabove, for applications in which frame 60 comprises ring 66, each leg 50 is coupled to the ring at a respective trough 62. Ring 66 may comprise struts 70, extending between the peaks and troughs, with each first end 72 at (or close to) a trough 62, and each second end 74 at (or close to) a peak 64.

In the compressed state of frame assembly 22 (and in particular of tubular portion 32), each strut 70 is disposed at a first angle in which first end 72 is disposed closer than second end 74 to the downstream end of the frame assembly. Expansion of frame assembly 22 (and in particular of tubular portion 32) toward its expanded state causes strut 70 to deflect to a second angle. This deflection moves first end 72 away from the downstream end of frame assembly 22. That is, in the expanded state of frame assembly 22, first end 72 is further from the downstream end of the frame assembly than it is when the frame assembly is in its compressed state. This movement is shown as a distance d5 between the position of end 72 in state (A) and its position in state (B). This movement causes the above-described movement of flanges 54 away from coupling points 52. As shown, flanges 54 typically move the same distance d5 in response to expansion of frame assembly 22.

For applications in which outer frame 60 comprises ring 66, the pattern of alternating peaks and troughs may be described as having an amplitude longitudinally between the peaks and troughs, i.e., measured parallel with central longitudinal axis ax1 of frame assembly 22, and the transition between the compressed and expanded states may be described as follows: In the compressed state of frame assembly 22 (and in particular of tubular portion 32), the pattern of ring 66 has an amplitude d20. In the expanded state frame assembly 22 (and in particular of tubular portion 32), the pattern of ring 66 has an amplitude d21 that is lower than amplitude d20. Because (i) it is at peaks 64 that ring 66 is coupled to valve frame 30 at coupling points 52, and (ii) it is at troughs 62 that ring 66 is coupled to legs 50, this reduction in the amplitude of the pattern of ring 66 moves legs 50 (e.g., flanges 54 thereof) longitudinally further from the downstream end of the frame assembly. The magnitude of this longitudinal movement (e.g., the difference between magnitudes d20 and d21) is equal to d5.

Typically, distance d5 is the same distance as the distance that flange 54 moves away from coupling point 52 during expansion of the frame assembly. That is, a distance between flange 54 and the portion of leg 50 that is coupled to strut 70, typically remains constant during expansion of the frame assembly. For some applications, the longitudinal movement of flange 54 away from coupling point 52 is a translational movement (e.g., a movement that does not include rotation or deflection of the flange).

For some applications, a distance d6, measured parallel to axis ax1 of frame assembly 22, between coupling point 52 and first end 72 of strut 70 while assembly 22 is in its compressed state, is 3-15 mm. For some applications, a distance d7, measured parallel to axis ax1, between coupling point 52 and first end 72 of strut 70 while assembly 22 is in its expanded state, is 1-5 mm (e.g., 1-4 mm).

For some applications, amplitude d20 is 2-10 mm (e.g., 4-7 mm). For some applications, amplitude d21 is 4-9 mm (e.g., 5-7 mm).

For some applications, and as shown, in the expanded state, first end 72 of strut 70 is disposed closer to the downstream end of frame assembly 22 than is coupling point 52. For some applications, in the expanded state, first end 72 of strut 70 is disposed further from the downstream end of frame assembly 22 than is coupling point 52.

For applications in which frame assembly 22 comprises a plurality of legs 50 and a plurality of coupling points 52 (e.g., for applications in which the frame assembly comprises outer frame 60) expansion of the frame assembly increases a circumferential distance between adjacent coupling points 52, and an increase in a circumferential distance between adjacent legs 50. FIG. 3A shows such an increase in the circumferential distance between adjacent coupling points 52, from a circumferential distance d8 in the compressed state to a circumferential distance d9 in the expanded state. For some applications, distance d8 is 1-6 mm. For some applications, distance d9 is 3-15 mm.

For some applications, in addition to being coupled via ring 66 (e.g., struts 70 thereof) legs 50 are also connected to each other via connectors 78. Connectors 78 allow the described movement of legs 50 during expansion of frame assembly 22, but typically stabilize legs 50 relative to each other while the frame assembly is in its expanded state. For example, connectors 78 may bend and/or deflect during expansion of the frame assembly.

FIGS. 3B-C show structural changes in valve frame 30 during the transitioning of frame assembly 22 between its compressed and expanded states. Tubular portion 32 of valve frame 30 is defined by a plurality of cells 80, which are defined by the repeating pattern of the valve frame. When frame assembly 22 is expanded from its compressed state toward its expanded state, cells 80 (i) widen from a width d10 to a width d11 (measured orthogonal to axis ax1 of the frame assembly), and (ii) shorten from a height d12 to a height d13 (measured parallel to axis ax1 of the frame assembly). This shortening reduces the overall height (i.e., a longitudinal length between upstream end 34 and downstream end 36) of tubular portion 32 from a height d22 to a height d23, and thereby causes the above-described longitudinal movement of upstream support portion 40 toward coupling points 52 by a distance d14 (shown in FIG. 3C). For some applications, and as shown, coupling points 52 are disposed at the widest part of each cell.

Figure 4A:
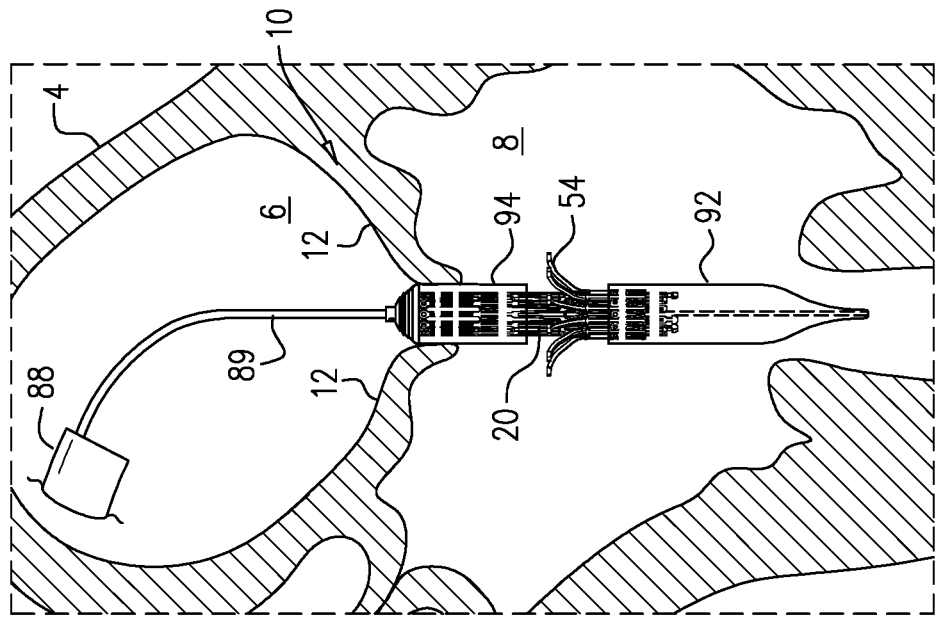
Figure 4B:
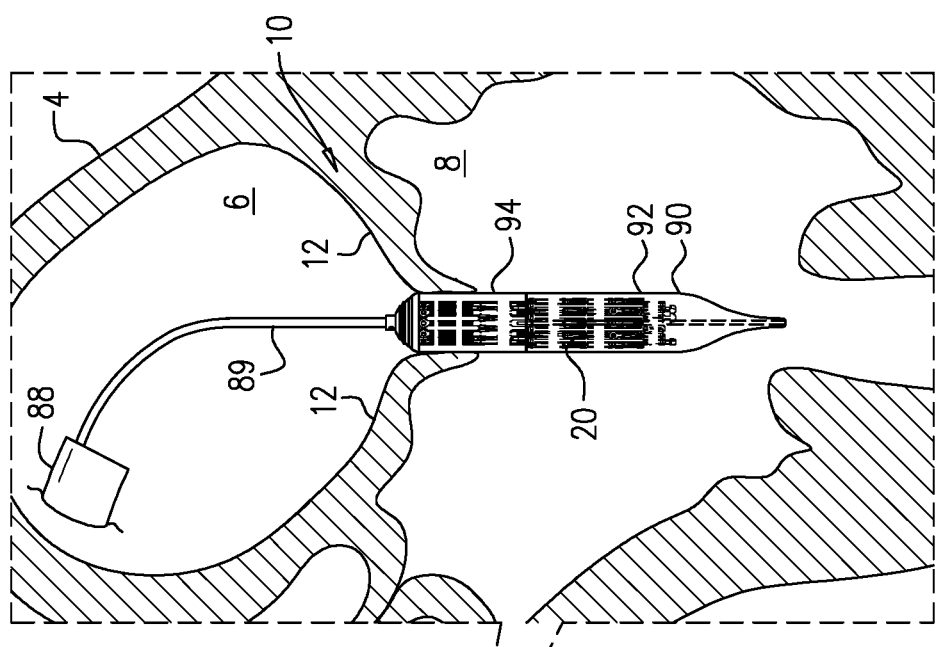
Figure 4F:
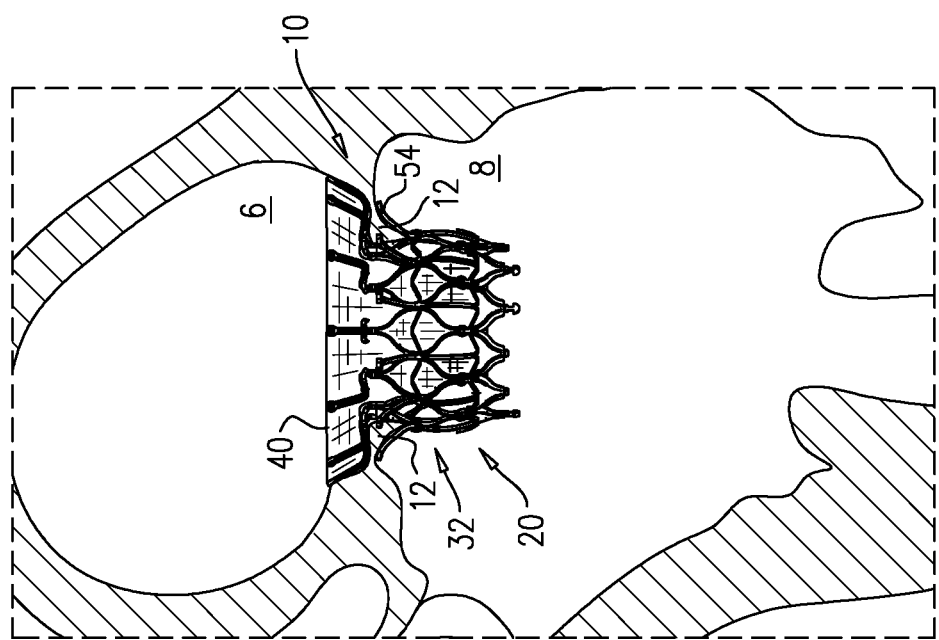
Figure 4E:
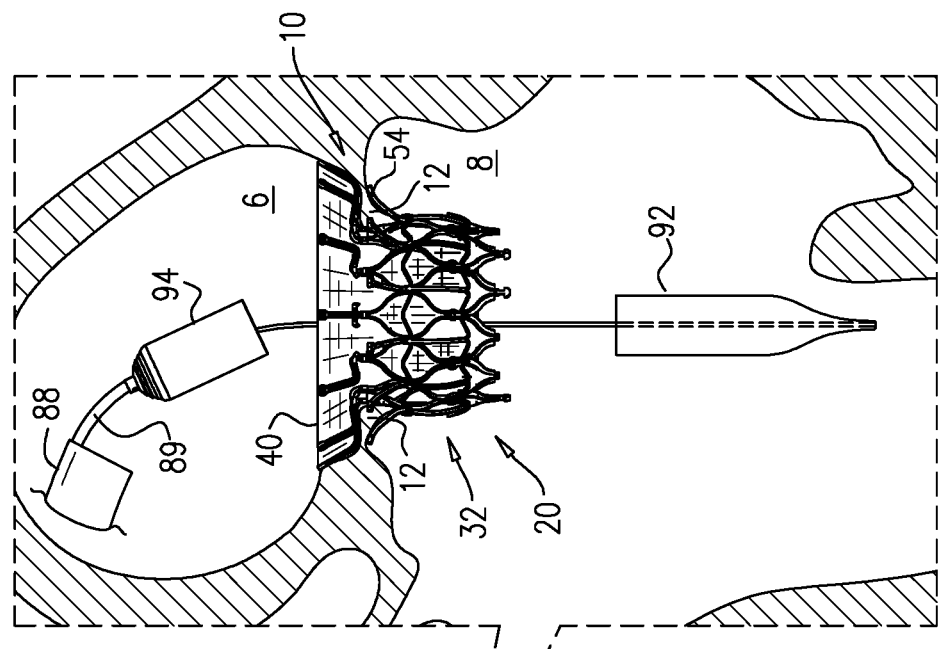

Due to the configurations described herein, the distance by which flanges 54 move with respect to (e.g., toward, or toward-and-beyond) upstream support portion 40 (e.g., arms 46 thereof), is typically greater than the reduction in the overall height of tubular portion 32 (e.g., more than 20 percent greater, such as more than 30 percent greater, such as more than 40 percent greater). That is, implant 20 comprises:

a valve frame (30) that comprises a tubular portion (32) that circumscribes a longitudinal axis (ax1) of the valve frame so as to define a lumen (38) along the axis, the tubular portion having an upstream end (34), a downstream end (36), a longitudinal length therebetween, and a diameter (e.g., d1 or d2) transverse to the longitudinal axis;

a valve member (58), coupled to the tubular portion, disposed within the lumen, and arranged to provide unidirectional upstream-to-downstream flow of blood through the lumen;

an upstream support portion (40), coupled to the tubular portion; and an outer frame (60), coupled to the tubular portion, and comprising a tissue-engaging flange (54), wherein:

the implant has a first state (e.g., as shown in FIG. 2D and FIG. 4D) and a second state (e.g., as shown in FIG. 2E and FIG. 4E), in both the first state and the second state, (i) the upstream support portion extends radially outward from the tubular portion, and (ii) the tissue-engaging flange extends radially outward from the tubular portion, and the tubular portion, the upstream support portion, and the outer frame are arranged such that transitioning of the implant from the first state toward the second state:
increases the diameter of the tubular portion by a diameter-increase amount (e.g., the difference between d1 and d2),
decreases the length of the tubular portion by a length-decrease amount (e.g., the difference between d22 and d23), and
moves the flange a longitudinal distance with respect to (e.g., toward or toward-and-beyond) the upstream support portion (e.g., the difference between d3 and d4), this distance being greater than the length-decrease amount.

As shown in the figures, valve frame 30 is typically coupled to outer frame 60 by coupling between (i) a valve-frame coupling element 31 defined by valve frame 30, and (ii) an outer-frame coupling element 61 defined by outer frame 60 (e.g., an outer-frame coupling element is coupled to end 74 of each strut). Typically, elements 31 and 61 are fixed with respect to each other. Each coupling point 52 is thereby typically defined as the point at which a valve-frame coupling element and a corresponding outer-frame coupling element 61 are coupled (e.g., are fixed with respect to each other). For some applications, and as shown, elements 31 and 61 are eyelets configured to be coupled together by a connector, such as a pin or a stitch (e.g., a suture). The fixing of elements 31 and 61 with respect to each other may be achieved by welding, soldering, crimping, stitching (e.g., suturing), gluing, or any other suitable technique.

Typically, and as shown, valve-frame coupling elements 31 are defined by tubular portion 32, and are disposed circumferentially around central longitudinal axis ax1. Outer-frame coupling elements 61 are coupled to ring 66 (or defined by frame 60, such as by ring 66) at respective peaks 64.

As shown (e.g., in FIGS. 2A-E), valve frame 30 (e.g., tubular portion 32 thereof) and outer frame 60 (e.g., ring 66 thereof) are arranged in a close-fitting coaxial arrangement, in both the expanded and compressed states of frame assembly 22. Ignoring spaces due to the cellular structure of the frames, a radial gap d19 between valve frame 30 (e.g., tubular portion 32 thereof) and outer frame 60 (e.g., ring 66 thereof) is typically less than 2 mm (e.g., less than 1 mm), in both the compressed and expanded states, and during the transition therebetween. This is facilitated by the coupling between frames 30 and 60, and the behavior, described hereinabove, of frame 60 in response to changes in the diameter of tubular portion 32 (e.g., rather than solely due to delivery techniques and/or tools). For some applications, more than 50 percent (e.g., more than 60 percent) of ring 66 is disposed within 2 mm of tubular portion 32 in both the compressed and expanded states, and during the transition therebetween. For some applications, more than 50 percent (e.g., more than 60 percent) of outer frame 60, except for flanges 54, is disposed within 2 mm of tubular portion 32 in both the compressed and expanded states, and during the transition therebetween.

The structural changes to frame assembly 22 (e.g., to outer frame 60 thereof) are described hereinabove as they occur during (e.g., as a result of) expansion of the frame assembly (in particular tubular portion 32 thereof). This is the natural way to describe these changes because, as described hereinbelow with respect to FIGS. 4A-6, assembly 22 is in its compressed state during percutaneous delivery to the implant site, and is subsequently expanded. However, the nature of implant 20 may be further understood by describing structural changes that occur during compression of the frame assembly (e.g., a transition from the expanded state in FIG. 2E to the intermediate state in FIG. 2D), in particular tubular portion 32 thereof (including if tubular portion 32 were compressed by application of compressive force to the tubular portion, and not to frame 60 except via the tubular portion pulling frame 60 radially inward). Such descriptions may also be relevant because implant 20 is typically compressed (i.e., "crimped") soon before its percutaneous delivery, and therefore these changes may occur while implant 20 is in the care of the operating physician.

For some applications, the fixation of peaks 64 to respective sites of tubular portion 32 is such that compression of the tubular portion from its expanded state toward its compressed state such that the respective sites of the tubular portion pull the peaks radially inward via radially-inward tension on coupling points 52: (i) reduces a circumferential distance between each of the coupling points and its adjacent coupling points (e.g., from d9 to d8), and (ii) increases the amplitude of the pattern of ring 66 (e.g., from d21 to d20).

For some applications, the fixation of outer-frame coupling elements 61 to valve-frame coupling elements 31 is such that compression of tubular portion 32 from its expanded state toward its compressed state such that the valve-frame coupling elements pull the outer-frame coupling elements radially inward: (i) reduces a circumferential distance between each of the outer-frame coupling elements and its adjacent outer-frame coupling elements (e.g., from d9 to d8), and (ii) increases the amplitude of the pattern of ring 66 (e.g., from d21 to d20).

For some applications, the fixation of peaks 64 to the respective sites of tubular portion 32 is such that compression of the tubular portion from its expanded state toward its compressed state (i) pulls the peaks radially inward via radially-inward pulling of the respective sites of the tubular portion on the peaks, (ii) reduces a circumferential distance between each of coupling points 52 and its adjacent coupling points (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

For some applications, the fixation of outer-frame coupling elements 61 with respect to valve-frame coupling elements 31 is such that compression of tubular portion 32 from its expanded state toward its compressed state (i) pulls outer-frame coupling elements 61 radially inward via radially-inward pulling of valve-frame coupling elements 31 on outer-frame coupling elements 61, (ii) reduces a circumferential distance between each of the outer-frame coupling elements and its adjacent outer-frame coupling elements (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

Reference is made to FIGS. 4A-F, which are schematic illustrations of implantation of implant 20 at a native valve 10 of a heart 4 of a subject, in accordance with some applications of the invention. Valve 10 is shown as a mitral valve of the subject, disposed between a left atrium 6 and a left ventricle 8 of the subject. However, implant 20 may be implanted at another heart valve of the subject, mutatis mutandis. Similarly, although FIGS. 4A-F show implant 20 being delivered transseptally via a sheath 88, the implant may alternatively be delivered by any other suitable route, such as transatrially, or transapically.

Implant 20 is delivered, in its compressed state, to native valve 10 using a delivery tool 89 that is operable from outside the subject (FIG. 4A). Typically, implant 20 is delivered within a delivery capsule 90 of tool 89, which retains the implant in its compressed state. A transseptal approach, such as a transfemoral approach, is shown. Typically, implant 20 is positioned such that at least flanges 54 are disposed downstream of the native valve (i.e., within ventricle 8). At this stage, frame assembly 22 of implant 20 is as shown in FIG. 2A.

Subsequently, flanges 54 are allowed to protrude radially outward, as described hereinabove, e.g., by releasing them from capsule 90 (FIG. 4B). For example, and as shown, capsule 90 may comprise a distal capsule-portion 92 and a proximal capsule-portion 94, and the distal capsule-portion may be moved distally with respect to implant 20, so as to expose flanges 54. At this stage, frame assembly 22 of implant 20 is as shown in FIG. 2B.

Subsequently, implant 20 is moved upstream, such that upstream support portion 40, in its compressed state, is disposed upstream of leaflets 12 (i.e., within atrium 6). For some applications, the upstream movement of implant 20 causes flanges 54 to engage leaflets 12. However, because of the relatively large distance d3 provided by implant 20 (described hereinabove), for some applications it is not necessary to move the implant so far upstream that flanges 54 tightly engage leaflets 12 and/or pull the leaflets upstream of the valve annulus. Upstream support portion 40 is then allowed to expand such that it protrudes radially outward, as described hereinabove, e.g., by releasing it from capsule 90 (FIG. 4D). For example, and as shown, proximal capsule-portion 94 may be moved proximally with respect to implant 20, so as to expose upstream support portion 40. At this stage, frame assembly 22 of implant 20 is as shown in FIG. 2D, in which: (i) distance d3 exists between upstream support portion 40 and flanges 54, (ii) the flanges have span d15, (iii) the upstream support portion has span d17, and (iv) tubular portion 32 has diameter d1.

Typically, expansion of frame assembly 22 is inhibited by distal capsule-portion 92 (e.g., by inhibiting expansion of tubular portion 32), and/or by another portion of delivery tool 89 (e.g., a portion of the delivery tool that is disposed within lumen 38).

Subsequently, implant 20 is allowed to expand toward its expanded state, such that tubular portion 32 widens to diameter d2, and the distance between upstream support portion 40 and flanges 54 reduces to distance d4 (FIG. 4E). This sandwiches tissue of valve 10 (typically including annular tissue and/or leaflets 12) between upstream support portion 40 and flanges 54, thereby securing implant 20 at the valve. FIG. 4F shows delivery capsule 90 having been removed from the body of the subject, leaving implant 20 in place at valve 10.

As described hereinabove, implant 20 is configured such that when tubular portion 32 is expanded, flanges 54 and upstream support portion 40 move a relatively large distance toward each other. This enables distance d3 to be relatively large, while distance d4 is sufficiently small to provide effective anchoring. As also described hereinabove, implant 20 is configured such that flanges 54 and upstream support portion 40 can extend radially outward a relatively large distance while tubular portion 32 remains compressed. It is hypothesized that for some applications, these configurations (independently and/or together) facilitate effective anchoring of implant 20, by facilitating placement of a relatively large proportion of valve tissue (e.g., leaflets 12) between the flanges and the upstream support portion prior to expanding tubular portion 32 and sandwiching the valve tissue.

It is further hypothesized that the relatively great radially-outward extension of flanges 54 and upstream support portion 40 prior to expansion of tubular portion 32, further facilitates the anchoring/sandwiching step by reducing radially-outward pushing of the valve tissue (e.g., leaflets 12) during the expansion of the tubular portion, and thereby increasing the amount of valve tissue that is sandwiched.

It is yet further hypothesized that this configuration of implant 20 facilitates identifying correct positioning of the implant (i.e., with upstream support portion 40 upstream of leaflets 12 and flanges 54 downstream of the leaflets) prior to expanding tubular portion 32 and sandwiching the valve tissue.

As shown in FIG. 1A, for some applications, in the expanded state of frame assembly 22, implant 20 defines a toroidal space 49 between flanges 54 and upstream support portion 40 (e.g., a space that is wider than distance d4). For example, space 49 may have a generally triangular cross-section. It is hypothesized that for some such applications, in addition to sandwiching tissue of the native valve between upstream support portion 40 and flanges 54 (e.g., the tips of the flanges), space 49 advantageously promotes tissue growth therewithin (e.g., between leaflet tissue and covering 23), which over time further secures implant 20 within the native valve.

Figure 5:
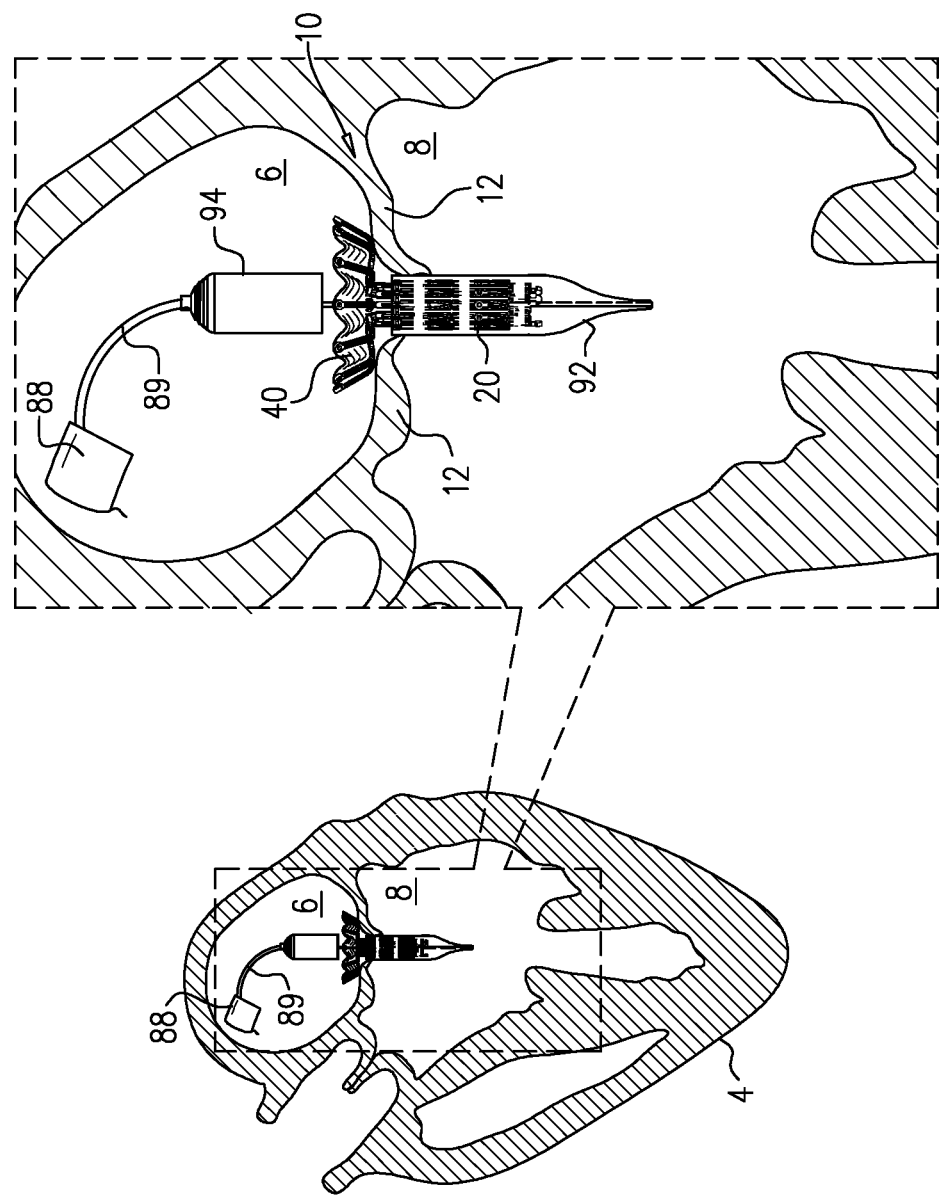
FIG. 5 is a schematic illustration of a step in the implantation of the implant, in accordance with some applications of the invention.

Reference is now made to FIG. 5, which is a schematic illustration of a step in the implantation of implant 20, in accordance with some applications of the invention. Whereas FIGS. 4A-F show an implantation technique in which flanges 54 are expanded prior to upstream support portion 40, for some applications the upstream support portion is expanded prior to the flanges. FIG. 5 shows a step in such an application.

Reference is again made to FIGS. 2A-5. As noted hereinabove, implant 20 may be implanted by causing flanges 54 to radially protrude before causing upstream support portion 40 to radially protrude, or may be implanted by causing the upstream support portion to protrude before causing the flanges to protrude. For some applications, implant 20 is thereby configured to be deliverable in a downstream direction (e.g., transseptally, as shown, or transapically) or in an upstream direction (e.g., transapically or via the aortic valve). Thus, for some applications, an operating physician may decide which delivery route is preferable for a given application (e.g., for a given subject, and/or based on available equipment and/or expertise), and implant 20 is responsively prepared for the chosen delivery route (e.g., by loading the implant into an appropriate delivery tool).

It is to be noted that for some applications, downstream delivery of implant 20 may be performed by expanding flanges 54 first (e.g., as shown in FIGS. 4A-F) or by expanding upstream support portion 40 first (e.g., as shown in FIG. 5). Similarly, for some applications upstream delivery of implant 20 may be performed by upstream support portion 40 first, or by expanding flanges 54 first.

Figure 6:
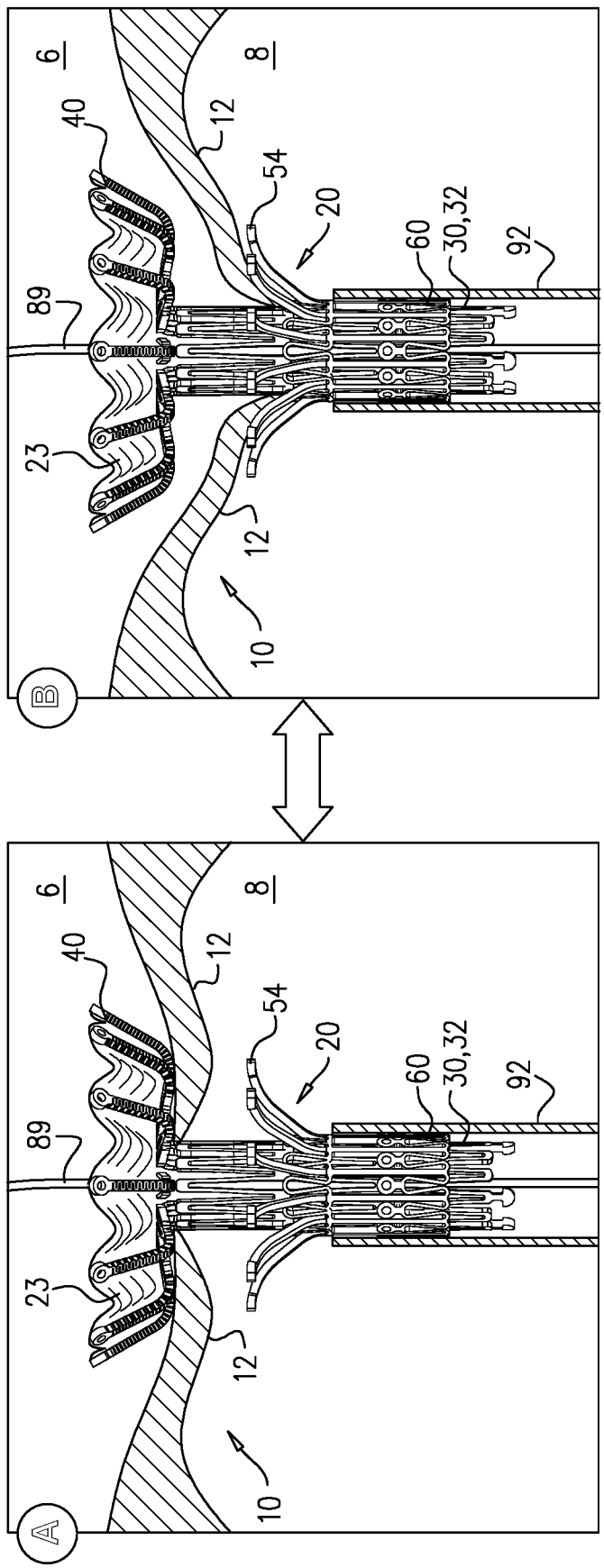
FIG. 6 is a schematic illustration of the implant, in accordance with some applications of the invention.

Reference is now made to FIG. 6, which is a schematic illustration of implant 20, in the state and position shown in FIG. 4D, in accordance with some applications of the invention. For some applications, while implant 20 is in the state and position shown in FIG. 4D, leaflets 12 of valve 10 are able to move, at least in part in response to beating of the heart. Frame (A) shows leaflets 12 during ventricular systole, and frame (B) shows the leaflets during ventricular diastole. For some such applications, blood is thereby able to flow from atrium 6 to ventricle 8, between leaflets 12 and implant 20. It is hypothesized that this advantageously facilitates a more relaxed implantation procedure, e.g., facilitating retaining of implant 20 in this state and position for a duration of greater than 8 minutes. During this time, imaging techniques may be used to verify the position of implant 20, and/or positioning of leaflets 12 between upstream support portion 40 and flanges 54.

Reference is made to FIGS. 7A-B and 8A-B, which are schematic illustrations of frame assemblies 122 and 222 of respective implants, in accordance with some applications of the invention. Except where noted otherwise, frame assemblies 122 and 222 are typically identical to frame assembly 22, mutatis mutandis. Elements of frame assemblies 122 and 222 share the name of corresponding elements of frame assembly 22. Additionally, except where noted otherwise, the implants to which frame assemblies 122 and 222 belong are similar to implant 20, mutatis mutandis.

Frame assembly 122 comprises (i) a valve frame 130 that comprises a tubular portion 132 and an upstream support portion 140 that typically comprises a plurality of arms 146, and (ii) an outer frame (e.g., a leg frame) 160 that circumscribes the valve frame, and comprises a plurality of legs 150 that each comprise a tissue-engaging flange 154. Typically, outer frame 160 comprises a ring 166 to which legs 150 are coupled. Ring 166 is defined by a pattern of alternating peaks and troughs, the peaks being fixed to frame 130 at respective coupling points 152, e.g., as described hereinabove for frame assembly 22, mutatis mutandis.

Frame assembly 222 comprises (i) a valve frame 230 that comprises a tubular portion 232 and an upstream support portion 240 that typically comprises a plurality of arms 246, and (ii) an outer frame (e.g., a leg frame) 260 that circumscribes the valve frame, and comprises a plurality of legs 250 that each comprise a tissue-engaging flange 254. Typically, outer frame 260 comprises a ring 266 to which legs 250 are coupled. Ring 266 is defined by a pattern of alternating peaks and troughs, the peaks being fixed to frame 230 at respective coupling points 252, e.g., as described hereinabove for frame assembly 22, mutatis mutandis.

Whereas arms 46 of frame assembly 22 are shown as extending from upstream end 34 of tubular portion 32, arms 146 and 246 of frame assemblies 122 and 222, respectively, extend from sites further downstream. (This difference may also be made to frame assembly 22, mutatis mutandis.) Tubular portions 32, 132 and 232 are each defined by a repeating pattern of cells that extends around the central longitudinal axis. Typically, and as shown, tubular portions 32, 132 and 232 are each defined by two stacked, tessellating rows of cells. In the expanded state of each tubular portion, these cells are typically narrower at their upstream and downstream extremities than midway between these extremities. For example, and as shown, the cells may be roughly diamond or astroid in shape. In frame assembly 22, each arm 46 is attached to and extends from a site 35 that is at the upstream extremity of cells of the upstream row. In contrast, in frame assemblies 122 and 222, each arm 146 or 246 is attached to and extends from a site 135 (assembly 122) or 235 (assembly 222) that is at the connection between two adjacent cells of the upstream row (alternatively described as being at the upstream extremity of cells of the downstream row).

It is hypothesized by the inventors that this lower position of the arms, while maintaining the length of the lumen of the tubular portion, advantageously reduces the distance that the tubular portion (i.e., the downstream end thereof) extends into the ventricle of the subject, and thereby reduces a likelihood of inhibiting blood flow out of the ventricle through the left ventricular outflow tract. It is further hypothesized that this position of the arms reduces radial compression of the tubular portion by movement of the heart, due to greater rigidity of the tubular portion at sites 135 and 235 (which is supported by two adjacent cells) than at site 35 (which is supported by only one cell).

As shown, in the expanded state of frame assemblies 22, 122 and 222, the legs (50, 150 and 250, respectively) are circumferentially staggered with the arms of the upstream support portion (46, 146 and 246, respectively). This allows the legs to move in an upstream direction between the arms during expansion of the tubular portion (32, 132 and 232, respectively), facilitating application of greater sandwiching force on tissue of the native valve. The lower position of the arms of assemblies 122 and 222 includes circumferentially shifting the position of the arms by the width of half a cell. In order to maintain the circumferential staggering of the arms and legs, rings 166 and 266 (and thereby legs 150 and 250) are circumferentially shifted correspondingly. As a result, whereas the peaks of ring 66 generally align with connections between adjacent cells of the downstream row of cells of tubular portion 32 (and are fixed to these sites), the peaks of rings 166 and 266 are generally aligned midway between these sites (i.e., at spaces of the cellular structure of the tubular portion). Appendages 168 (for assembly 122) or 268 (for assembly 222) facilitate fixing of the peak with respect to the tubular structure.

For assembly 122, appendages 168 are defined by valve frame 130 (e.g., by tubular portion 132 thereof) and extend (in a downstream direction) to the peaks of ring 166, to which they are fixed. For example, each appendage 168 may define a valve-frame coupling element 131 that is fixed to a respective outer-frame coupling element 161 defined by outer frame 260. Typically, appendages 168 extend from sites 135. Typically, appendages 168 are integral with tubular portion 132 and/or in-plane with the tubular portion (e.g., are part of its tubular shape).

For assembly 222, appendages 268 are defined by outer frame 260, and extend (e.g., in an upstream direction) from the peaks of ring 266. Typically, appendages 268 extend to sites 235, to which they are fixed. For example, each appendage 268 may define an outer-frame coupling element 261 that is fixed to a respective valve-frame coupling element 231 defined by valve frame 230 (e.g., by tubular portion 232 thereof). Typically, appendages 268 are integral with outer frame 260 and/or in-plane with adjacent portions of outer frame 260, such as ring 266.

Therefore, frame assembly 122 defines a hub at site 135, and frame assembly 222 defines a hub at site 235. For some applications, apparatus therefore comprises:

a plurality of prosthetic valve leaflets; and a frame assembly, comprising:

a tubular portion (132 or 232) defined by a repeating pattern of cells, the tubular portion extending circumferentially around longitudinal axis ax1 so as to define a longitudinal lumen, the prosthetic valve leaflets coupled to the inner frame and disposed within the lumen;

an outer frame (160 or 260), comprising a plurality of legs (150 or 250), distributed circumferentially around the tubular portion, each leg having a tissue-engaging flange (154 or 254);

an upstream support portion (140 or 240) that comprises a plurality of arms (146 or 246) that extend radially outward from the tubular portion; and a plurality of appendages (168 or 268), each having a first end that defines a coupling element (161 or 261) via which the tubular portion is coupled to the outer frame, and a second end;

wherein the frame assembly defines a plurality of hubs (135 or 235), distributed circumferentially around the longitudinal axis on a plane that is transverse to longitudinal axis ax1, each hub defined by convergence and connection of, (i) two adjacent cells of the tubular portion, (ii) an arm of the plurality of arms, and (iii) an appendage of the plurality of appendages.

Reference is made to FIGS. 9A-C, which are schematic illustrations of an implant 320 comprising a frame assembly 322, in accordance with some applications of the invention. Except where noted otherwise, frame assembly 322 is identical to frame assembly 122, and implant 300 is identical to the implant to which frame assembly 122 belongs, mutatis mutandis. FIG. 9A is a side-view of implant 320, and FIG. 9B is an isometric bottom-view of the implant.

Frame assembly 122 comprises (i) a valve frame 330 that comprises a tubular portion 332 and an upstream support portion 340 that typically comprises a plurality of arms 346, and (ii) an outer frame (e.g., a leg frame) 360 that circumscribes the valve frame, and comprises a plurality of legs 350 that each comprise a tissue-engaging flange 354. Typically, outer frame 360 comprises a ring 366 to which legs 350 are coupled. Ring 366 is defined by a pattern of alternating peaks and troughs, the peaks being fixed to frame 330 at respective coupling points 352, e.g., as described hereinabove for frame assembly 22 and/or frame assembly 122, mutatis mutandis.

Frame assembly 322 comprises an annular upstream support portion 340 that has an inner portion 342 that extends radially outward from the upstream portion (e.g., the upstream end) of tubular portion 332. Upstream support portion 340 further comprises one or more fabric pockets 344 disposed circumferentially around inner portion 342, each pocket of the one or more pockets having an opening that faces a downstream direction (i.e., generally toward the downstream end of implant 320). In the figures, upstream support portion 340 has a single toroidal pocket 344 that extends circumferentially around inner portion 342.

Typically, a covering 323 (e.g., similar to covering 23, described hereinabove, mutatis mutandis) is disposed over arms 346, thereby forming pocket 344. Further typically, arms 346 are shaped to form pocket 344 from covering 323. For example, and as shown, arms 346 may curve to form a hook-shape.

For some applications, portion 340 has a plurality of separate pockets 344, e.g., separated at arms 346. For some such applications, covering 323 is loosely-fitted (e.g., baggy) between radially-outward parts of arms 346, e.g., compared to inner portion 342, in which the covering is more closely-fitted between radially-inward parts of the arms.

FIG. 9C shows implant 320 implanted at native valve 10. Pocket 344 is typically shaped and arranged to billow in response to perivalvular flow 302 of blood in an upstream direction. If ventricular systole forces blood in ventricle 8 between implant 320 and native valve 10, that blood inflates pocket 344 and presses it (e.g., covering 323 and/or the radially-outward part of arm 346) against tissue of atrium 6 (e.g., against the atrial wall), thereby increasing sealing responsively. It is hypothesized by the inventors that the shape and orientation of pocket 344 (e.g., the hook-shape of arms 346) facilitates this pressing radially-outward in response to the pocket's receipt of upstream-flowing blood.

Pocket(s) 344 may be used in combination with any of the implants described herein, mutatis mutandis.

Reference is now made to FIG. 10, which is a schematic illustration of a frame assembly 422 of an implant, in accordance with some applications of the invention. Except where noted otherwise, frame assembly 422 is typically identical to frame assembly 122, mutatis mutandis. Elements of frame assembly 422 share the name of corresponding elements of frame assembly 122. Additionally, except where noted otherwise, the implant to which frame assembly 422 belongs is similar to implant the other implants described herein (e.g., implant 20), mutatis mutandis. FIG. 10 shows frame assembly 422 in an expanded state (e.g., in the absence of external deforming forces, such as those provided by a delivery tool during implantation, or by heart tissue after implantation).

Frame assembly 422 comprises (i) a valve frame (e.g., an inner frame) 430 that comprises a tubular portion 432 and an upstream support portion 440 that typically comprises a plurality of radial arms 446, and (ii) an outer frame (e.g., a leg frame) 460 that circumscribes the valve frame, and comprises a plurality of legs 450 that each comprise a tissue-engaging flange 454. Typically, outer frame 460 comprises a ring 466 to which legs 450 are coupled. Ring 466 is defined by a pattern of alternating peaks and troughs, the peaks being fixed to frame 430 at respective coupling points 452, e.g., as described hereinabove for frame assemblies 22 and 122, mutatis mutandis. Tubular portion 432 has a diameter d26 (corresponding to diameter d2 of implant 20), and a transverse cross-sectional area that is a function of diameter d26.

Similarly to other frame assemblies described herein, in the expanded state of frame assembly 422, legs 450 are circumferentially staggered with arms 446 of upstream support portion 440. This allows the legs (e.g., flanges 454 thereof) to move in an upstream direction between the arms during deployment of the implant (although the presence of heart tissue typically reduces the amount by which flanges 454 move between arms 446). FIG. 10 shows frame assembly 422 in its expanded state, in which upstream support portion 440 (e.g., arms 446) and flanges 454 extend radially outward from tubular portion 432, and intersect at an intersection 470. Opposite intersections 470 define an intersect diameter d27. Typically, flanges 454 extend radially outward from the tubular portion and toward the upstream support portion 440 (i.e., outward and in an upstream direction). A toroidal space 449 is defined between flanges 454, upstream support portion 440, and tubular portion 432, the toroidal space circumscribing the tubular portion.

As described hereinabove with respect to other implants, the implant to which frame assembly 422 belongs is secured at the native valve by sandwiching heart tissue (e.g., leaflets 12 and/or the valve annulus) between upstream support portion 440 and flanges 54 (e.g., within space 449). Typically, leaflets 12 are trapped in space 449. Space 449 is dimensioned to be sufficiently large to accommodate leaflets 12, because it has been observed by the inventors that if space 449 is too small, the implant tends to become secured to tissue that is suboptimally close to the middle of the native valve orifice (e.g., closer to the free edges of the leaflets), and to sit in a position that is suboptimally downstream (i.e., into ventricle 8). Additionally, space 449 is dimensioned to be sufficiently small to accommodate leaflets 12 snugly, because it has been observed by the inventors that if space 449 is sufficiently small that the leaflets fill the space well (typically folding or bunching up within the space), sandwiching forces are applied to leaflet tissue throughout space 449. In contrast, if space 449 is too large, sandwiching forces may be applied to the leaflets only at or close to intersections 470, reducing the effectiveness of anchoring, and/or increasing a likelihood of damaging the tissue at or close to the intersections.

It is hypothesized by the inventors that an optimal size of space 449 (i.e., a size that is sufficiently large to accommodate leaflets 12, but sufficiently small to do so snugly) is achieved when the space has a cross-sectional area 451 that is 5-10 percent (e.g., 5-8 percent, such as 6-7 percent or 6.5-7.5 percent) of the transverse cross-sectional area of tubular portion 432. It is further hypothesized that this relative size is optimal across implants that have tubular portions of different diameters. For example:

For an implant in which diameter d26 is 25 mm, an optimally-sized cross-sectional area 451 may be 25-40 (e.g., about 35) mm^2.

For an implant in which diameter d26 is 27 mm, an optimally-sized cross-sectional area 451 may be 30-45 (e.g., about 40) mm^2.

For an implant in which diameter d26 is 29 mm, an optimally-sized cross-sectional area 451 may be 35-50 (e.g., about 45) mm^2.

This optimal relative size range of area 451 is hypothesized by the inventors to apply to implants that have tubular portions that are narrower or wider than the above examples (e.g., 23 mm or 31 mm diameter).

For some applications, implants of different diameters d26 are provided, and each of the implants has a cross-sectional area 451 that is 5-10 percent (e.g., 5-8 percent, such as 6-7 percent or 6.5-7.5 percent) of the transverse cross-sectional area of the tubular portion 432 of the implant. For example, the tubular portion 432 of one of the implants may have a have transverse cross-sectional area that is at least 15 percent (e.g., at least 30 percent) greater than another one of the implants.

Tubular portion 432 has an upstream end 434 and a downstream end 436. Similarly to frame assembly 122, arms 446 are attached to and extend from sites 435 that are downstream of upstream end 434, e.g., at the connection between two adjacent cells of the upstream row of cells of tubular portion 432 (alternatively described as being at the upstream extremity of cells of the downstream row of cells).

Progressively lateral portions of each arm 446 define, respectively: (i) an ascending portion 446a that extends in an upstream direction past upstream end 434 of tubular portion 432 (e.g., by a distance d28), (ii) an arch portion 446b that curves in a downstream direction to form an arch (portion 446b may alternatively be described as being convex in an upstream direction), and (iii) a lateral portion 446c that curves in an upstream direction. For some applications, in the absence of tissue, arch portion 446b curves in the downstream direction as far as (and typically past) tips 455 of flanges 454 (i.e., at the arch portion, each arm 446 extends below (i.e., further downstream than) adjacent tips 455). For some applications, and as shown, intersections 470 are generally close to where arms 446 begin to curve upstream.

A height d29 is the height, along the central longitudinal axis of the implant, between (i) the crest of arch portion 446b, and (ii) intersection 470. For some applications, height d29 is 0.5-3.5 mm (e.g., 1.8-2.6 mm).

A height d30 is the height, along the central longitudinal axis of the implant, between (i) the crest of arch portion 446b, and (ii) site 435. For some applications, height d30 is 4-7.5 mm (e.g., 5.2-6.5 mm).

It is to be noted, therefore, that for some applications, arms 446 extend (i) radially outward and above (a) upstream end 434 and (b) the tips of flanges 454, and then (ii) further radially outward and below (a) upstream end 434 and/or (b) the tips of flanges 454 (i.e., toward the flanges). The above configuration of arm 46 increases the size of toroidal space 449 (compared to a similar arm in which d28 and/or d29 are smaller), e.g., providing an optimal cross-sectional area 451, as described hereinabove. (In contrast, for example, in frame assemblies 122 and 222, the arms do not have arch portions that extend above (i) the upstream end of the respective tubular portion, or (ii) the tips of the respective flanges. Although the lateral portions of these arms do extend upwardly, the lateral portions are radially outward of the flanges, and therefore do not increase the cross-sectional area of the toroidal space defined by these frame assemblies.) For some applications, an end 446d (i.e., the lateral extremity) of arm 446 is disposed further in an upstream direction than arch portion 446b.

For some applications, the outer stent frame (e.g., leg frame) 460 has a radial thickness d24 (i.e., a thickness measured along an axis that extends radially outward from the central longitudinal axis of the implant) that is greater than a radial thickness d25 of inner stent frame (e.g., valve frame) 430. That is, the outer stent frame is radially thicker than the inner stent frame. This is typically achieved by cutting (e.g., laser cutting) the inner stent frame from a nitinol tube that has a first wall thickness (e.g., equal to d25), and cutting the outer stent frame from another nitinol tube that has a second, greater wall thickness (e.g., equal to d24). However, other methods of manufacture, including 3D printing, may be used.

For some applications, thickness d24 is at least 10 percent (e.g., at least 20 percent, such as at least 30 percent) and/or no more than 80 percent (e.g., no more than 50 percent) greater than thickness d25. For some applications, thickness d24 is 0.6-0.8 mm (e.g., 0.7-0.75 mm, e.g., 0.71-0.73 mm, such as 0.72 mm), and thickness d25 is 0.45-0.65 mm (e.g., 0.5-0.55 mm, e.g., 0.52-0.54 mm, such as 0.53 mm).

Having the outer stent frame (e.g., leg frame) be radially thicker than inner stent frame (e.g., valve frame) may be applied to the other frame assemblies described herein, mutatis mutandis.

There is therefore provided, in accordance with some applications of the invention, apparatus comprising:
(1) a frame assembly, transluminally advanceable to the heart, and comprising:
  (i) an inner stent frame that defines a tubular portion; and
  (ii) an outer stent frame that defines a ring that is coupled to the inner stent frame, and circumscribes the tubular portion; and
(2) a plurality of prosthetic valve leaflets, coupled to the frame assembly and disposed in the tubular portion,
wherein the inner stent frame is cut from a first tube of nitinol that has a first-tube wall thickness, the outer stent frame is cut from a second tube of nitinol that has a second-tube wall thickness that is greater than the first-tube wall thickness.

Providing a frame assembly in which the outer frame has greater radial thicknesses is hypothesized by the inventors to advantageously provide (i) radially-expansive strength (and resistance to radially-inward deformation) to the portion of the frame assembly in which the prosthetic leaflets are disposed, and (ii) rigidity (and resistance to fatigue) to legs 450.

For some applications, when frames 430 and 460 are separate and independent (e.g., during manufacturing, before the frames are fixed to each other), and the frames are in respective relaxed expanded states (e.g., in the absence of external deforming forces, such as if placed on a table) tubular portion 432 defines an inner-stent-frame relaxed expanded diameter (which is measured as an outer diameter of the tubular portion) that is greater than an outer-stent-frame relaxed expanded diameter defined by ring 466 (which is measured as an inner diameter of the ring). For some applications, the inner-stent-frame relaxed expanded diameter is 0.5-1.5 (e.g., 0.5-1, such as 0.8) mm greater than the outer-stent-frame relaxed expanded diameter.

Therefore, in the expanded state of frame assembly 422 (shown in FIG. 10), frame 460 (e.g., ring 466) constrains tubular portion 432 to an inner-stent-frame constrained expanded diameter that is smaller than the inner-stent-frame relaxed expanded diameter. Therefore, even in the relaxed expanded state of frame assembly 422 (i.e., the state shown in FIG. 10), residual stress is typically present in frame 430 (e.g., tubular portion 432 thereof) and/or frame 460 (e.g., ring 466 thereof). Additionally, when the frame assembly is in its compressed state, and throughout its expansion into its expanded state, circumferential contact (and reciprocating expansive and compressive forces) is maintained between frame 460 and tubular portion 432.

It is hypothesized by the inventors that this optional residually-stressed configuration advantageously increases the strength of the frame assembly (e.g., the tubular portion), and in particular its resistance to deformation, e.g., in response to forces applied directly to the frame assembly by tissue of the native valve, and/or applied indirectly to the frame assembly during systole when ventricular blood is forced against the prosthetic leaflets, which pull on the frame assembly.

It is to be noted that frames 430 and 460 are fixed to each other independently of any additional coupling that might be provided by the residually-stressed configuration. For example, and as described hereinabove, the frames are fixed to each other at coupling points 452, e.g., by welding, soldering, crimping, stitching (e.g., suturing), gluing, or any other suitable technique. As described hereinbelow with reference to FIGS. 11A-C, for some applications the frames are also fixed to each other at commissures of the implant. That is, the residually-stressed configuration is provided for strength and rigidity of the frame assembly (and for ensuring maintenance of circumferential contact between the frames), rather than for coupling of the frames to each other.

Figure 11A:
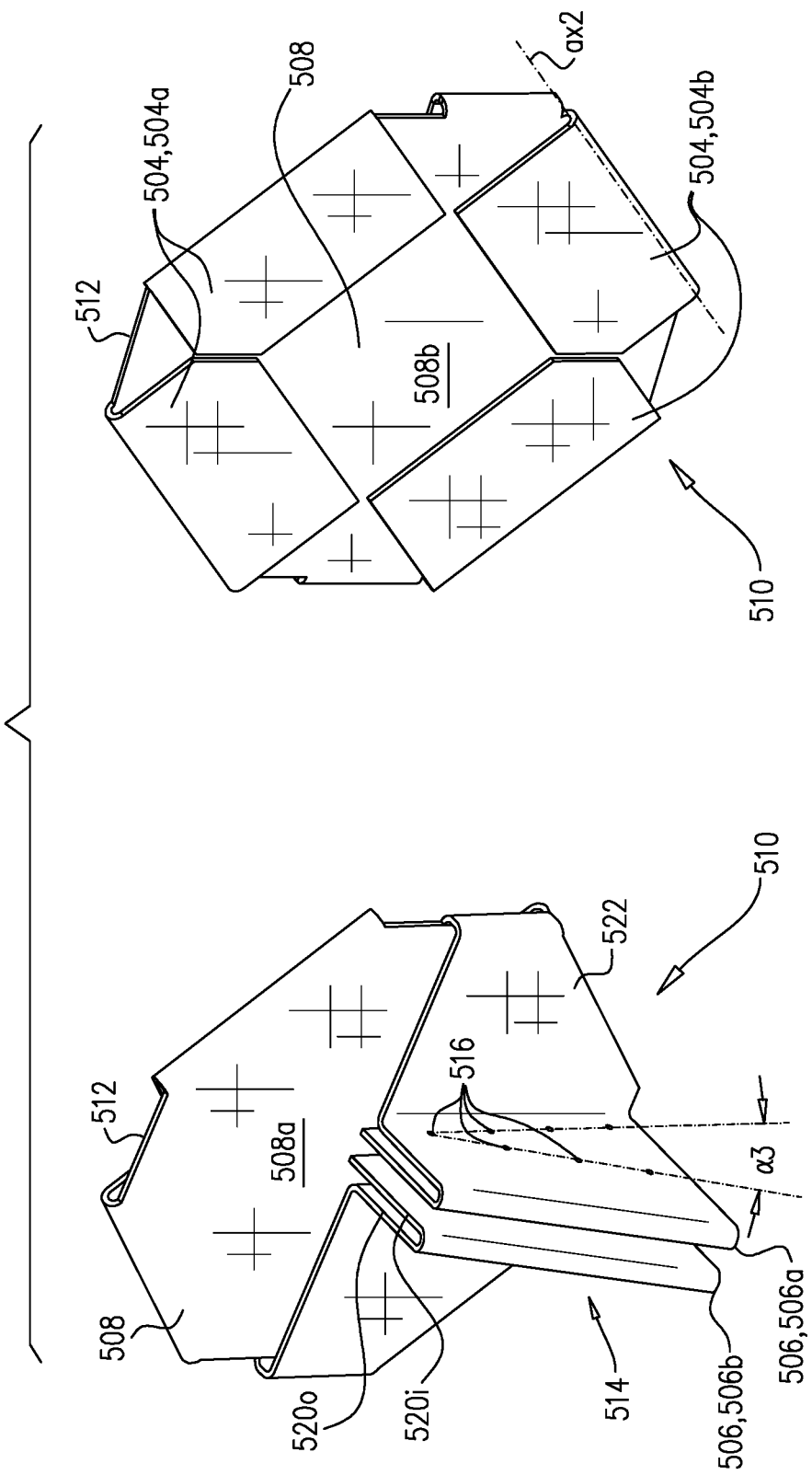
FIGS. 11A-C are schematic illustrations of a connector and a commissure of a prosthetic valve, in accordance with some applications of the invention.
Figure 11B:
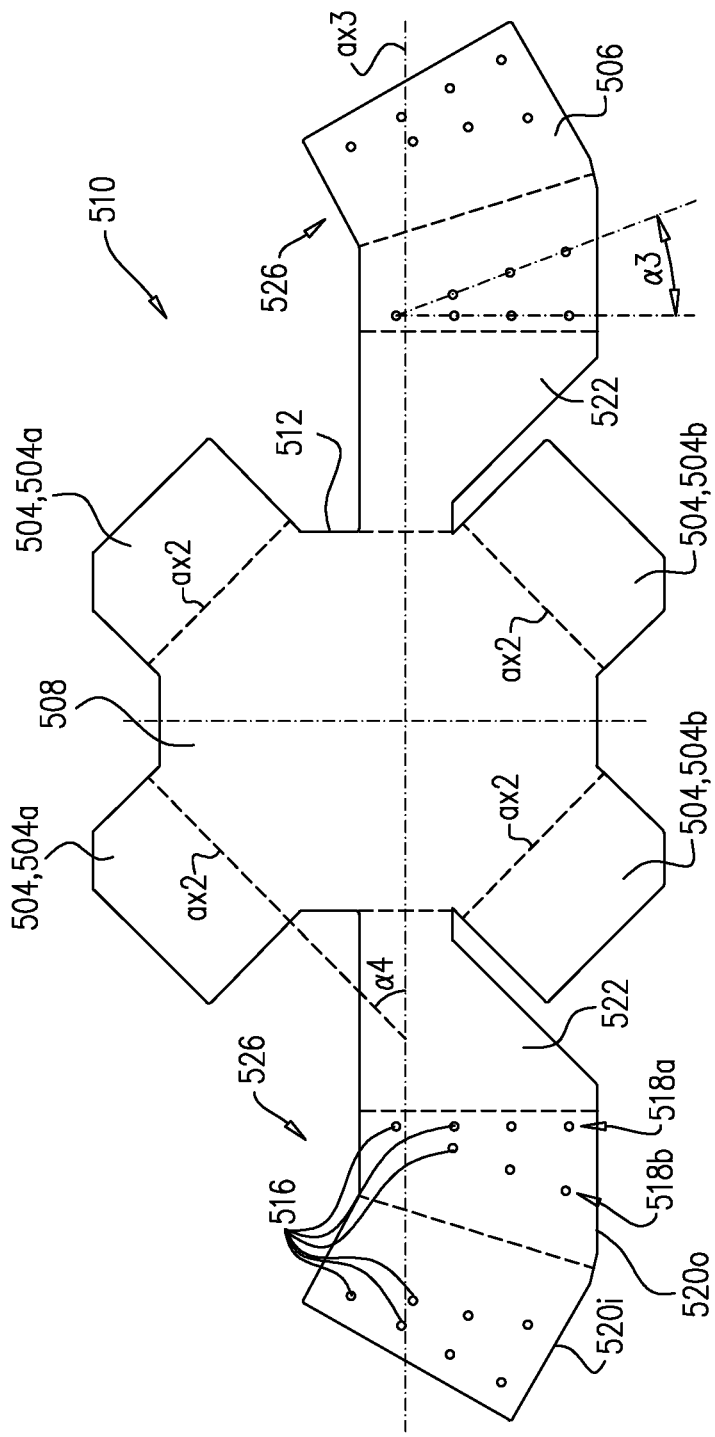
Figure 11C:
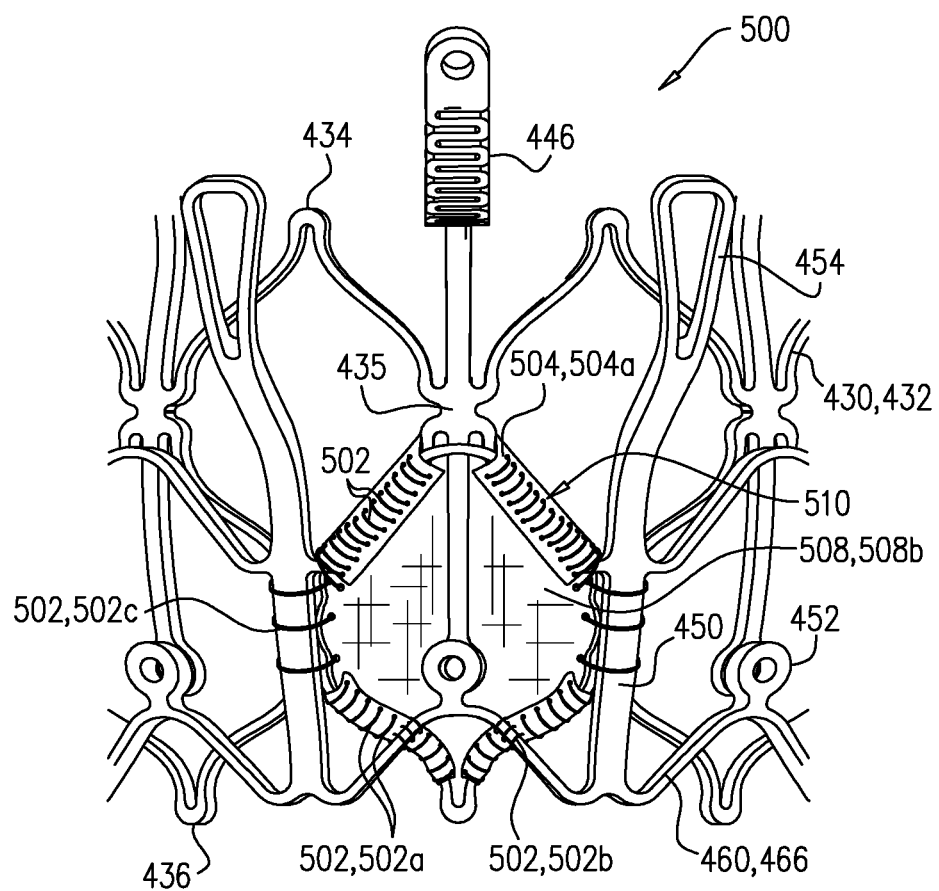

Reference is made to FIGS. 11A-C, which are schematic illustrations of a connector 510 and a commissure 500 of a prosthetic valve, in accordance with some applications of the invention. Connector 510 typically comprises a flexible sheet 512 that is folded to define elements of the connector. Further typically, sheet 512 is a single, unitary sheet (e.g., cut from a single piece of stock material). FIG. 11A shows two perspective views of connector 510 (e.g., sheet 512 thereof) in its folded state, and FIG. 11B shows its unfolded state. FIG. 11C shows connector 510 fixed to frame assembly 422 at commissure 500. Commissure 500 is described with respect to the implant to which frame assembly 422 belongs, although it may be used in combination with the other prosthetic valves described herein, and/or with other prosthetic valves, mutatis mutandis.

The implant to which frame assembly 422 belongs defines a plurality of commissures 500 at which two of the prosthetic leaflets of the implant (e.g., leaflets 58 or similar) meet, and are fixed to the frame assembly. At each commissure, the implant comprises a plurality of stitches (e.g., stitches) 502, via which commissural portions of the two prosthetic leaflets are secured to the frame assembly. For some applications, the stitches secure the prosthetic leaflets to the inner stent frame (frame 430, e.g., tubular portion 432 thereof) and to the outer stent frame (frame 460). That is, the leaflets are not coupled to the outer stent frame merely by being fixed to the inner stent frame, which in turn is coupled to the outer stent frame. Rather, the leaflets are fixed to both frames by stitches 502. Because (as described hereinabove) (i) frame 460 is radially thicker than frame 430, and (ii) the relative diameters of the frames results in residual stress and maintained circumferential contact between frames 430 and 460, the fixation of the leaflets to both frames advantageously provides the implant with enhanced resistance to pulling of commissures 500 radially inward by the prosthetic leaflets when ventricular pressure increases during ventricular systole.

For some applications, and as shown, stitches 502 fix the leaflets to both frames by fixing a connector 510 (typically comprising primarily or solely a fabric) to the two frames. Connector 510 is shaped to define a plurality of flaps 504, and a leaflet-receptacle 514 comprising one or more (e.g., two) leaflet-engaging tabs 506, such as a first leaflet-engaging tab 506a and a second leaflet-engaging tab 506b. For some applications, connector 510 is shaped to define a panel (e.g., a plate) 508, tabs 506 protrude from of one side of the panel, and each flap 504 folds over a respective portion of the other side of the panel. The commissural portions of the leaflets are stitched to leaflet-engaging tabs 506 (e.g., to respective leaflet-engaging tabs). Flaps 504 are stitched to frames 430 and 460—i.e., are fixed to the frames by stitches 502. Typically, flaps 504 are folded over or wrapped around elements of frames 430 and 460, and are fixed in this disposition by stitches 502, thereby providing increased strength to the fixation of the leaflets to the frames (and of the frames to each other).

Typically, connector 510 comprises four flaps 504. For some applications, and as shown, flaps 504 are arranged in a circuit such that each flap has two adjacent flaps around the circuit, and the fold axis ax2 of each flap is oriented at 60-120 degrees (e.g., 70-110 degrees, e.g., 80-100 degrees) from the fold axis of each of its adjacent flaps. For applications in which the frame to which connector 510 is to be connected has a cellular structure with roughly diamond-shape cells, such an arrangement facilitates attachment of the connector to the frame.

For some applications, and as shown, and as shown, connector 510 has four flaps arranged roughly in a diamond shape, with two upstream flaps 504a tapering away from each other in a downstream direction, and two downstream flaps 504b tapering toward each other in a downstream direction. Each upstream flap 504a is typically folded over or wrapped around an element of frame 430 and an element of frame 460. As can be seen in FIG. 11C, at commissure 500, elements of frame 430 align with elements of frame 460, and flaps 504a are arranged to align with these elements of both frames. Flaps 504 are folded over or wrapped around these elements of both frames, and are fixed to these elements by stitches 502. In the position of downstream flaps 504b, elements of frame 430 do not align with elements of frame 460, and may even be perpendicular to them. Downstream flaps 504b are arranged to align with elements of frame 430, and are folded over or wrapped around elements, but typically not over or around elements of frame 460. The elements of frame 430, and flaps 504b, are stitched to elements of frame 460; these stitches are indicated by the reference numeral 502b, while the stitches that secure flaps over or around frame elements are indicated by the reference numeral 502a. For some applications, panel 508 is also stitched to elements of frame 430 and/or frame 460; these stitches are indicated by the reference numeral 502c.

It is to be noted that frames 430 and 460 are thereby fixed to each other at commissures 500 (i.e., in addition to at coupling points 452).

Alternatively, connector 510 and/or the stitches may secure the leaflets only to inner frame 430, such that the leaflets are coupled to outer frame 460 only via inner frame 430.

There is therefore provided, in accordance with some applications of the invention, a connector (e.g., connector 510) comprising a flexible sheet (e.g., sheet 512) that is folded to define: (i) a panel (e.g., panel 508) that has a first side (e.g., side 508a), and a second side (e.g., side 508b) that is opposite the first side; (ii) a leaflet receptacle (e.g., receptacle 514), disposed on the first side of the panel, and protruding in the first direction away from the panel; and (iii) a plurality of flaps (e.g., flaps 504), each flap folded about a respective fold axis (e.g., axis ax2) such that at least part of each flap is disposed on the second side of the panel.

Receptacle 514 is configured to sandwich one or more prosthetic leaflets between leaflet-engaging tabs 506a and 506b. Typically, stitching holes 516 are defined in leaflet-engaging tabs 506 to guide the introduction of stitches which will secure the leaflets sandwiched between the tabs. For some applications, holes 516 are arranged into rows. For example, and as shown, each leaflet-engaging tab 506 may define a first row 518a of stitching holes and a second row 518b of stitching holes, the rows of one tab being aligned with the rows of the other tab. For some such applications, rows 518a and 518b diverge from each other at an angle alpha_3, typically such that that progressively downstream parts of the rows are progressively further from each other. For example, angle alpha_3 may be 10-45 degrees (e.g., 10-30 degrees, e.g., 15-25 degrees, such as about 20 degrees).

For some applications, sheet 512 is folded such that each leaflet-engaging tab 506 comprises an outer layer 520o, and an inner layer 520i that is positioned to be sandwiched between the outer layer and the one or more leaflets.

In the unfolded state of connector 510 (FIG. 11B), sheet 512 defines a plane (i.e., the plane of the page). In the unfolded state, sheet 512 defines, in the plane, (i) panel 508 at a medial region of sheet 512, (ii) flaps 504, disposed peripherally to the panel, and (iii) first and second tab portions 526, also disposed peripherally from the panel. Each tab portion 526 includes outer layer 520o and inner layer 520i, and in the folded state, defines a respective leaflet-engaging tab 506.

Typically, sheet 512 further defines bridging elements 522, via each of which a respective tab portion 526 is connected to panel 508. Flaps 504 are connected to panel 508 independently of the bridging elements.

In the unfolded state, tab portions 526 flank panel 508 by being disposed, in the plane, on opposing lateral sides of the panel. In the unfolded state, panel 508, tab portions 526, and bridging elements 522 are arranged in a row that defines a lateral axis ax3 in the plane, axis ax3 passing through the panel, tab portions, and bridging elements. Axis ax3 typically passes between upstream flaps 504a and downstream flaps 504b. Typically, the fold axis ax2 of each flap 504 is disposed at an angle alpha_4 that is 30-60 degrees from lateral axis ax3.

In the folded state, bridging elements 522 extend from respective edges of panel 508 and toward each other across first side 508a of the panel, and each of the leaflet-engaging tabs 506 protrudes from its respective bridging element away from the first side of the panel in the direction that the first side of the panel faces.

Reference is made to FIGS. 12A-B and 13A-F, which are schematic illustrations of another connector 610 for connecting prosthetic leaflets (e.g., leaflets 58) to a frame of a prosthetic valve implant, in accordance with some applications of the invention. Connector 610 may be used with any of the implants described herein, or with a different prosthetic valve, mutatis mutandis.

Figure 12B:
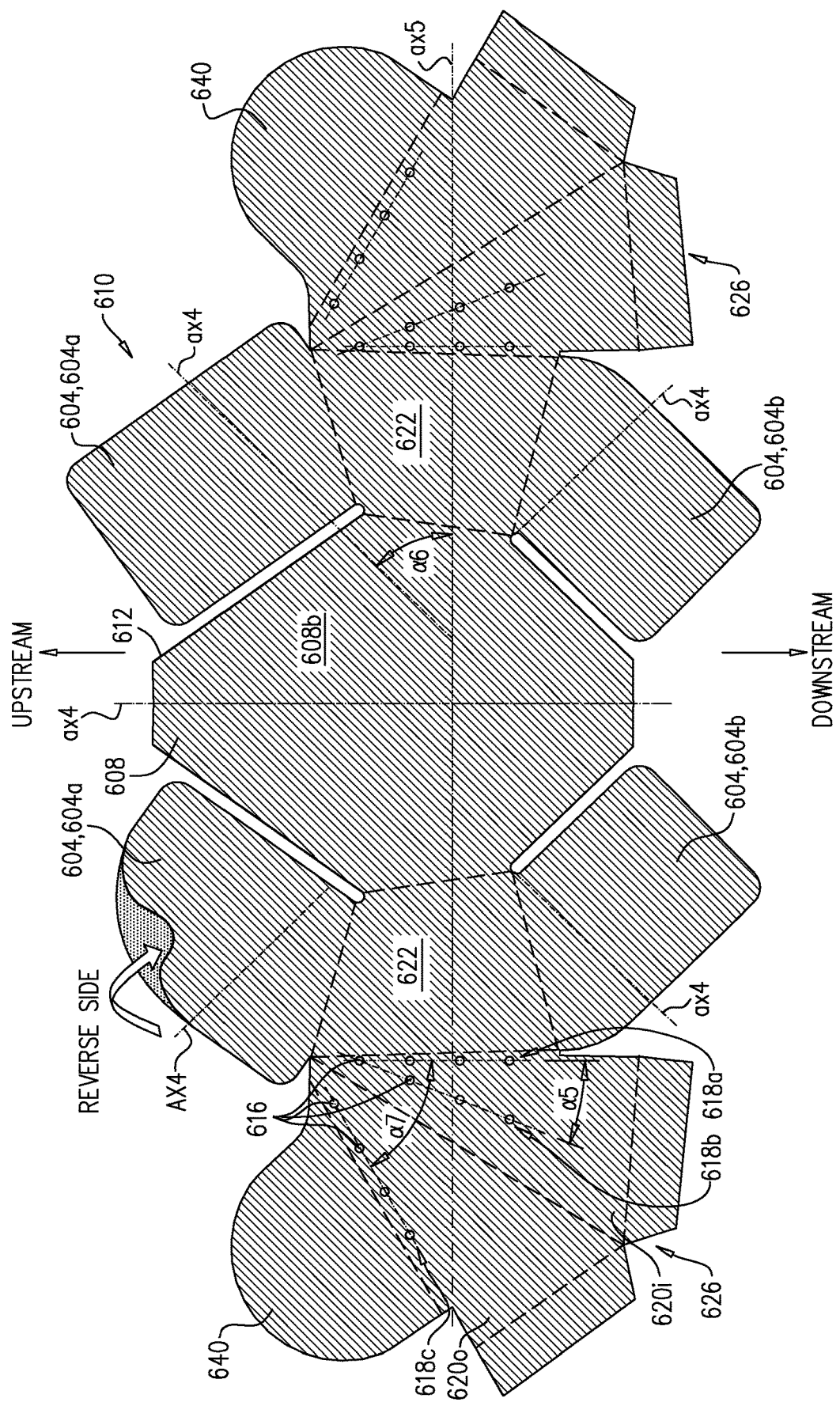

Connector 610 typically comprises a flexible sheet 612 that is folded to define elements of the connector. Further typically, sheet 612 is a single, unitary sheet (e.g., cut from a single piece of stock material). FIG. 12A shows two perspective views of connector 610 (e.g., sheet 612 thereof) in its folded state, and FIG. 12B shows its unfolded state. To facilitate illustration of the folding of sheet 612, in FIGS. 12B and 13A-F opposing sides of the sheet are differently shaded, e.g., as demonstrated by a corner of sheet 612 being curled over in FIG. 12B to show its reverse side.

Connector 610 (e.g., in its folded state) is shaped to define a plurality of flaps 604, and a leaflet-receptacle 614 comprising one or more (e.g., two) leaflet-engaging tabs 606, such as a first leaflet-engaging tab 606a and a second leaflet-engaging tab 606b. Connector 610 is typically shaped to define a panel (e.g., a plate) 608. In the folded state, tabs 606 protrude from of a first side 608a of the panel, and each flap 604 folds over a second side 608b of the panel (e.g., a respective portion thereof). The commissural portions of leaflets 58 are stitched to leaflet-engaging tabs 606. Flaps 604 are folded over or wrapped around elements of the frame of the prosthetic valve implant, e.g., as shown in FIG. 13F. Typically, flaps 604 are fixed in this disposition by stitches (not shown).

Typically, connector 610 comprises four flaps 604, typically two upstream flaps 604a and two downstream flaps 604b. For some applications, and as shown, flaps 604 are arranged in a circuit such that each flap has two adjacent flaps around the circuit, and the fold axis ax4 of each flap is oriented at 60-120 degrees (e.g., 70-110 degrees, e.g., 80-100 degrees) from the fold axis of each of its adjacent flaps. For applications in which the frame to which connector 610 is to be connected has a cellular structure with roughly diamond-shape cells, such an arrangement facilitates attachment of the connector to the frame, e.g., as shown in FIG. 13F.

There is therefore provided, in accordance with some applications of the invention, a connector (e.g., connector 610) comprising a flexible sheet (e.g., sheet 612) that is folded to define: (i) a panel (e.g., panel 608) that has a first side (e.g., side 608a), and a second side (e.g., side 608b) that is opposite the first side; (ii) a leaflet receptacle (e.g., receptacle 614), disposed on the first side of the panel, and protruding in a first direction away from the panel; and (iii) a plurality of flaps (e.g., flaps 604), each flap folded about a respective fold axis (e.g., axis ax4) such that at least part of each flap is disposed on the second side of the panel.

Receptacle 614 is configured to sandwich one or more prosthetic leaflets between leaflet-engaging tabs 606a and 606b. Typically, stitching holes 616 are defined in leaflet-engaging tabs 606 to guide the introduction of stitches which will secure the leaflets sandwiched between the tabs. For some applications, holes 616 are arranged into rows. For example, and as shown, each leaflet-engaging tab 606 may define a first row 618a of stitching holes and a second row 618b of stitching holes, the rows of one tab being aligned with the corresponding rows of the other tab. For some such applications, rows 618a and 618b diverge from each other at an angle alpha_5, typically such that that progressively downstream parts of the rows are progressively further from each other. For example, angle alpha_5 may be 10-45 degrees (e.g., 10-30 degrees, e.g., 15-25 degrees, such as about 20 degrees). Downstream is defined by the direction in which the prosthetic leaflets facilitate one-way fluid flow, which itself is in part dependent on the orientation of the attachment of the leaflets to connectors 610.

Typically, sheet 612 is folded such that each leaflet-engaging tab 606 comprises an outer layer 620o, and an inner layer 620i that is positioned to be sandwiched between the outer layer and the one or more leaflets. For some applications, and as further described hereinbelow, rows 618a and 618b are defined by inner layer 620i, and a third row 618c of stitching holes is defined by outer layer 620, and the folding of sheet 612 is such that row 618c aligns with row 618a. For such applications, only row 618c is visible in the folded state. In the unfolded state, an angle alpha_7 between rows 618a and 618c is typically 40-120 degrees (e.g., 40-90 degrees, e.g., 40-70 degrees, e.g., 40-60 degrees, such as 50-60 degrees).

In the unfolded state of connector 610 (FIG. 12B), sheet 612 defines a plane (i.e., the plane of the page). In the unfolded state, sheet 612 defines, in the plane, (i) panel 608 at a medial region of sheet 612, (ii) flaps 604, disposed peripherally to the panel, and (iii) first and second tab portions 626, also disposed peripherally from the panel. Each tab portion 626 includes outer layer 620o and inner layer 620i, and in the folded state, defines a respective leaflet-engaging tab 606.

Sheet 612 further defines bridging elements 622, via each of which a respective tab portion 626 is connected to panel 608. Flaps 504 are connected to panel 508 via the bridging elements.

Typically, in the folded state, part of each flap 604 is disposed on first side 608a of panel 608, and part of each flap is disposed on second side 608b. For example, bridging elements 622 are typically disposed on first side 608a, and each flap 604 extends from one of the bridging elements and around panel 608 such that part of the flap is disposed on side 608a, and part is disposed on side 608b.

In the unfolded state, tab portions 626 flank panel 608 by being disposed, in the plane, on opposing lateral sides of the panel. In the unfolded state, panel 608, tab portions 626, and bridging elements 622 are arranged in a row that defines a lateral axis ax5 in the plane, axis ax5 passing through the panel, tab portions, and bridging elements. Axis ax5 typically passes between upstream flaps 604a and downstream flaps 604b. Typically, the fold axis ax4 of each flap 604 is disposed at an angle alpha_6 that is 30-70 degrees from lateral axis ax5.

Sheet 612 typically further defines a lapel 640 that, in the unfolded state, is lateral to each tab portion 626. Lapels 640 are described further hereinbelow.

In the folded state, bridging elements 622 extend from respective edges of panel 608 and toward each other across first side 608a of the panel, and each of the leaflet-engaging tabs 606 protrudes from its respective bridging element away from the first side of the panel in the direction that the first side of the panel faces.

Figure 13A:
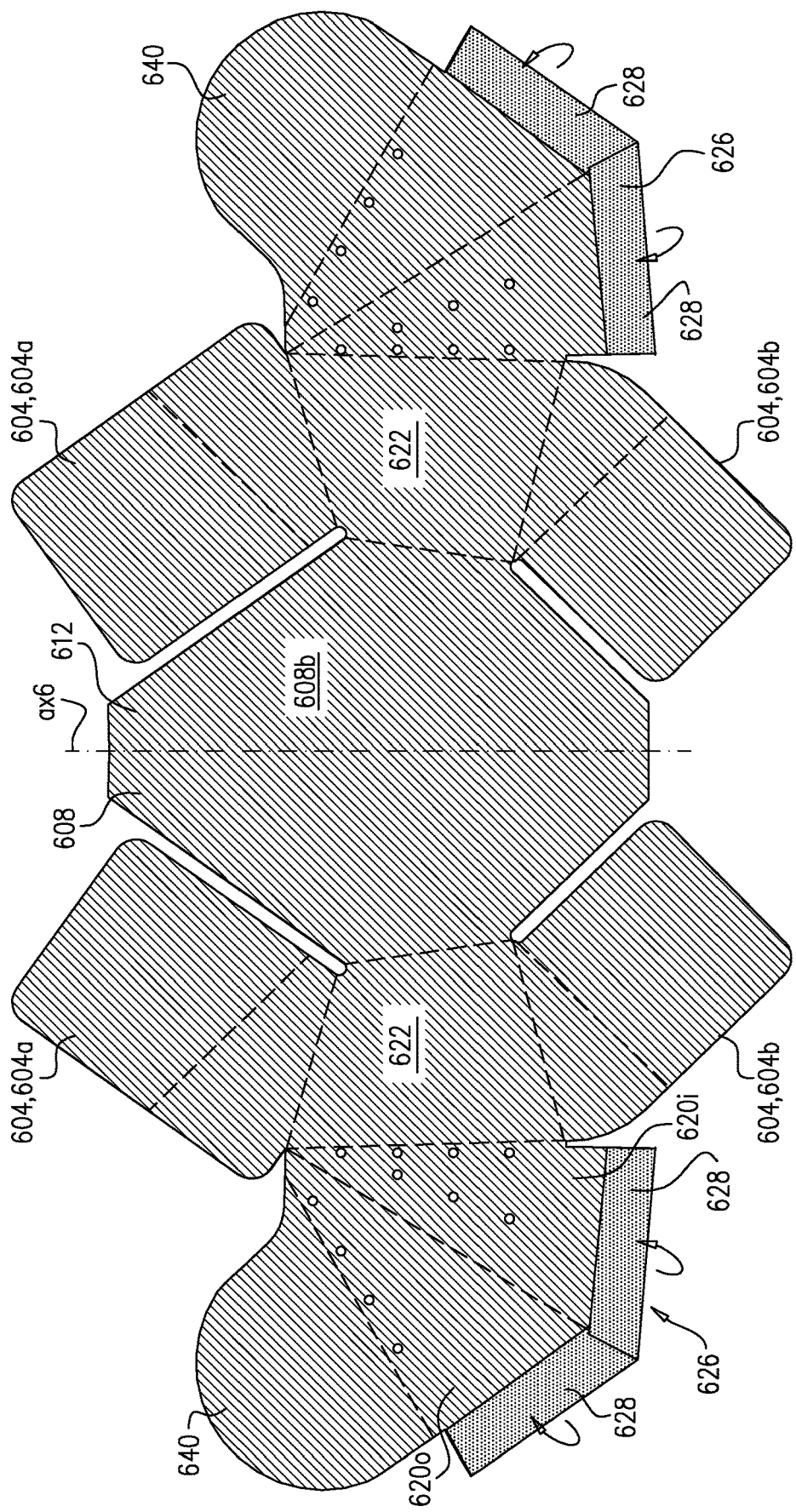
Figure 13B:
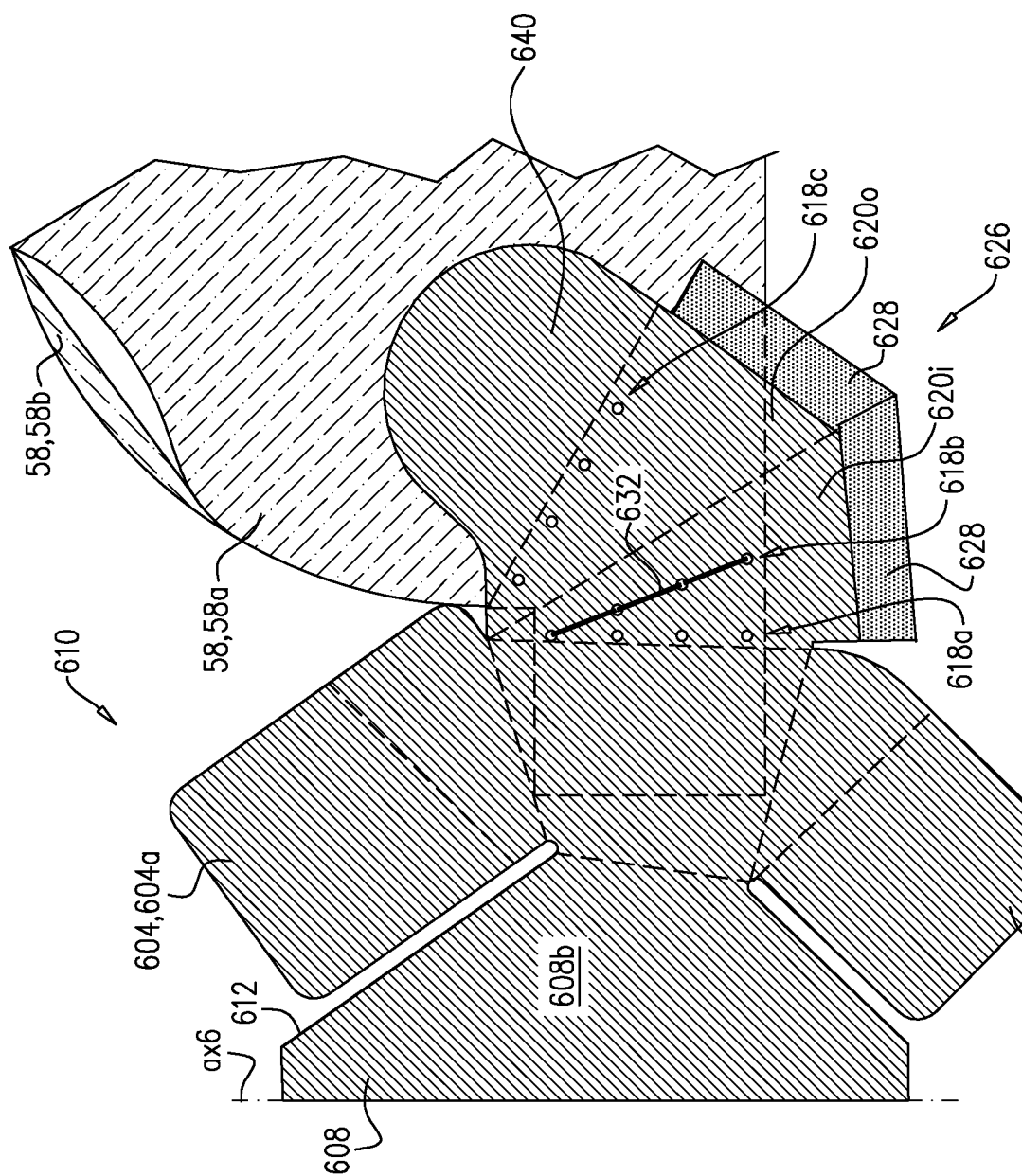
Figure 13F:
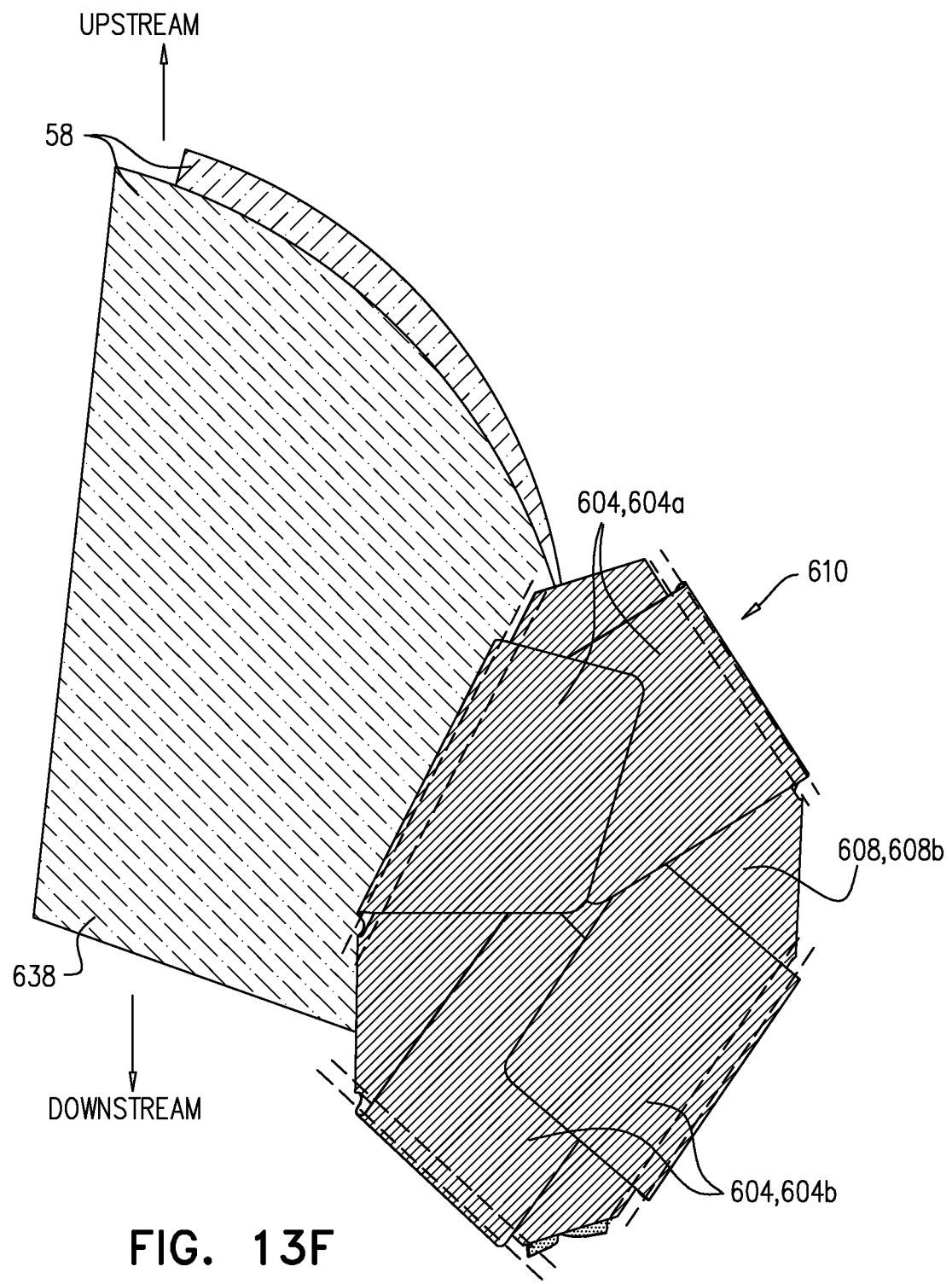

FIGS. 13A-F show steps in the folding of sheet 612 from the unfolded state to the folded state, in order to define connector 610, in accordance with some applications of the inventions. Folds are made in downstream regions of tab portions 626, e.g., the downstream edge of each layer 610o and each layer 610i is folded over to form respective folds 628 (FIG. 13A). This will provide each leaflet-engaging tab with a cushion 630, described hereinbelow. Folds 628 may be secured by stitching.

Sheet 612 is folded in half along its longitudinal axis ax6, bringing tab portions 626 together (FIG. 13B). Commissural portions of two leaflets 58 (e.g., a first leaflet 58a and a second leaflet 58b) are introduced, such that they are sandwiched together between portions 626. As shown, the positioning of the leaflets is typically such that they are disposed between the holes 616 of one portion 626, and those of the other portion 626. Holes 616 of row 618b of both portions 626 are stitched together, as indicated by reference numeral 632. The stitches therefore pass through leaflets 58a and 58b, thereby securing them to connector 610.

Subsequently, tab portions 626 are folded back against themselves, thereby defining inner layer 620i and outer layer 620o (FIG. 13C), and aligning rows 618c with rows 618a. Holes 616 of rows 618a and 618b are now hidden by outer layer 620o. Rows 618c and 618a of one tab portion 626, leaflets 58a and 58b, and rows 618a and 618c of the other tab portion are then stitched together, as indicated by reference numeral 634. This reinforces the connection of the leaflets to connector 610. Thus, tab portions 626 are formed into leaflet-engaging tabs 606.

Subsequent to the step shown in FIG. 13C, the folding in half of sheet 612 shown in step 13B is reversed, mutatis mutandis, moving bridging elements 622 away from each other and folding them against panel 608 (FIG. 13D). Typically, regions of each leaflet 58 that are disposed beyond row 618c become disposed between bridging elements 622 and panel 608.

Typically, the step shown in FIG. 13C brings lapels 640 into contact with bridging elements 622. The step shown in FIG. 13D typically causes each bridging element 622 to move with the bridging element 622 with which it is in contact, and folding with respect to outer layer 620i of leaflet-engaging tabs 606. For some applications, stitches are passed through lapel 640, bridging element 622, leaflet 58, and panel 608. This stitching may be an independent step, or may be achieved when securing flaps 604 to the frame of the prosthetic valve, e.g., as described hereinbelow.

FIG. 13E shows perspective views of the state shown in FIG. 13D. Each leaflet 58 has a downstream edge 638. It is to be noted that leaflet-engaging tabs 606 typically extend in a downstream direction beyond downstream edges 638. It is to be further noted that cushions 630 are typically positioned such that at least part of each cushion is disposed further downstream than downstream edges 638. Tabs 606 and/or cushions 630 are thereby configured to inhibit movement of the commissural portion of each leaflet 58 (and especially of downstream edges 638) toward the frame of the prosthetic valve. It is hypothesized by the inventors that this reduces a likelihood of leaflets 58 becoming damaged over time due to contact with the frame.

Subsequently, connector 610 is secured to the frame of the prosthetic valve (FIG. 13F). Flaps 604 are folded over components of the frame of the prosthetic valve (which are shown in phantom), and secured by stitching. For some applications, some of this stitching may pass through several elements, such as flaps 604, panel 608, leaflets 58, bridging elements 622, and/or lapels 640.

Although FIGS. 13A-F show a particular sequence, and although some of the steps are necessarily performed before others, it is to be understood that some of the steps may be performed in a different order to that shown. For example, folds 628 may be folded at a later stage to that shown.

Typically, three connectors 610 are used to connect three leaflets 58 at three commissures to the frame of the prosthetic valve, to form a tri-leaflet check-valve.

Reference is again made to FIGS. 1A-13F. Among the advantages provided by assembling a prosthetic valve from two (e.g., concentric) frames is the ability to divide the frame elements required between the two frames, in a manner that would not be possible in a single frame, or in a manner that, if a single frame were used, would increase the size (e.g., the diameter or the length) of the implant in its compressed state. Additionally, for some applications, the use of two frames allows different sizes of the implant to be compressed ("crimped") to the same or similar diameter, and for some such applications, to be delivered using the same delivery tool (e.g., delivery tool 89). For example, for implants comprising frame assembly 422, an implant of a larger size may have a lumen diameter that is at least 15 percent greater than the lumen diameter of an implant of a smaller size (in their respective expanded states), but in their compressed states, the diameter of the implant of the larger size may be no more than 2 percent greater than the diameter of the implant of the smaller size.

For some applications, a delivery tool is provided for use with different sizes of the implant, e.g., with the implants provided separately. For some such applications, a kit is provided containing a delivery tool and implants of different sizes.

Reference is again made to FIGS. 1A-13F. It is to be noted that unless specifically stated otherwise, the term "radially outward" (e.g., used to describe upstream support portion 40 and flanges 54) means portions of the element are disposed progressively further outward from a central point (such as longitudinal axis ax1 or tubular portion 32), but does not necessarily mean disposed at 90 degrees with respect to longitudinal axis ax1. For example, flanges 54 may extend radially outward at 90 degrees with respect to longitudinal axis ax1, but may alternatively extend radially outward at a shallower angle with respect to the longitudinal axis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a heart of a subject, the apparatus comprising an implant, the implant comprising:
    an inner stent frame that:
        defines a tubular portion and a plurality of inner-frame coupling elements, and
        has a relaxed expanded state in which the tubular portion defines an inner-stent-frame relaxed expanded diameter;
    a plurality of prosthetic leaflets, each prosthetic leaflet:
        secured to, and disposed within, the tubular portion, and
        defining a commissural portion;
    an outer stent frame, that:
        defines a ring and a plurality of outer-frame coupling elements, and
        has a relaxed expanded state in which the ring defines an outer-stent-frame relaxed expanded diameter that is smaller than the inner-stent-frame expanded diameter;
    a plurality of stitches, the stitches disposed at respective commissures defined by the implant; and
    a fabric connector, the fabric connector shaped to define (i) a panel having a first side and a second side, (ii) one or more leaflet-engaging tabs to which the commissural portions of the prosthetic leaflets are stitched, the tabs protruding from the first side of the panel, and (iii) a plurality of flaps, wrapped around elements of the inner stent frame and elements of the outer stent frame, and secured thus by the stitches;
wherein:
    the plurality of stitches secures the commissural portions of the two leaflets to the inner stent frame and the outer stent frame by being attached to the fabric connector; and
    the inner stent frame and the outer stent frame, together define at least part of a frame assembly in which:
        the outer-frame coupling elements are fixed to the inner-frame coupling elements,
        the ring circumscribes the tubular portion, and
        the frame assembly:
            has a compressed state in which the frame assembly is transluminally advanceable to the heart, and
            is expandable into an expanded state in which the tubular portion defines an inner-stent-frame constrained expanded diameter that is smaller than the inner-stent-frame relaxed expanded diameter.

2. The apparatus according to claim 1, wherein the outer frame is coupled to the inner frame such that:
    in the compressed state of the frame assembly, the outer frame is in circumferential contact with the tubular portion, and
    throughout expansion of the frame assembly into its expanded state, circumferential contact is maintained between the outer frame and the tubular portion.

3. The apparatus according to claim 1, wherein the outer-frame coupling elements are welded to the inner-frame coupling elements.

4. The apparatus according to claim 1, wherein, in the relaxed expanded state, the tubular portion is barrel-shaped.

* * * * *